US011291713B2

(12) United States Patent
van der Ley et al.

(10) Patent No.: US 11,291,713 B2
(45) Date of Patent: Apr. 5, 2022

(54) BORDETELLA VACCINES COMPRISING LPS WITH REDUCED REACTOGENICITY

(71) Applicant: De Staat der Nederlanden, vert. door de minister van VWS, Ministerie van Volksgezondheid, Welzijn en Sport, The Hague (NL)

(72) Inventors: Peter André van der Ley, Utrecht (NL); Jesús Andrés Arenas Busto, Ribadumia (ES); Elder Pupo Escalona, Amersfoort (NL); Johannes Petrus Maria Tommassen, Utrecht (NL)

(73) Assignee: Intravacc B.V., Bilthoven (NL)

( * ) Notice: Subject to any disclaimer, the term of this patent is extended or adjusted under 35 U.S.C. 154(b) by 11 days.

(21) Appl. No.: 16/493,309

(22) PCT Filed: Mar. 13, 2018

(86) PCT No.: PCT/EP2018/056241
§ 371 (c)(1),
(2) Date: Sep. 12, 2019

(87) PCT Pub. No.: WO2018/167061
PCT Pub. Date: Sep. 20, 2018

(65) Prior Publication Data

US 2020/0085933 A1 Mar. 19, 2020

(30) Foreign Application Priority Data

Mar. 13, 2017 (EP) .................................... 17160604

(51) Int. Cl.
*A61K 39/02* (2006.01)
*A61P 31/04* (2006.01)
*C12N 1/20* (2006.01)
*C12N 9/10* (2006.01)
*C12N 9/14* (2006.01)
*A61K 39/00* (2006.01)

(52) U.S. Cl.
CPC ............ *A61K 39/099* (2013.01); *A61P 31/04* (2018.01); *C12N 1/20* (2013.01); *C12N 9/1029* (2013.01); *C12N 9/14* (2013.01); *C12Y 306/01054* (2013.01); *A61K 2039/6087* (2013.01); *C12N 2510/00* (2013.01)

(58) Field of Classification Search
None
See application file for complete search history.

(56) References Cited

U.S. PATENT DOCUMENTS 8,048,433 B2 * 11/2011 Tommassen ......... A61K 39/099
424/234.1

FOREIGN PATENT DOCUMENTS

WO WO2006/065139 A2 6/2006
WO WO-2006065139 A2 * 6/2006 ........... C07K 14/235

OTHER PUBLICATIONS

Caroff et al. 1999 (Contribution of 252 Cf-plasma desorption mass spectrometry to structural analysis of lipids A: examples of non-conservatism in lipid A structure; Journal of Endotoxin Research, vol. 5, Nos. 1-2) (Year: 1999).*
Steeghs et al. 2002 (Expression of foreign LpxA acyltransferases in Neisseria meningitidis results in modified lipid A with reduced toxicity and retained adjuvant activity; Cellular Microbiology 4 (9), 599-611 (Year: 2002).*
Shah et al. 2013 (Minor Modifications to the Phosphate Groups and the C3' Acyl Chain Length of Lipid A in Two Bordetella pertussis Strains, BP338 and 18-323, Independently Affect Toll-like Receptor 4 Protein Activation; The Journal of Biological Chemistry vol. 288, No. 17, pp. 11751-11760). (Year: 2013).*
Greenspan et al. 1999 (Defining epitopes: It's not as easy as it seems; Nature Biotechnology, 17:936-937) (Year: 1999).*
J. Geurtsen et al: Expression of the Lipopolysaccharide-Moditying Enzymes PagP and PagL Modulates the Endotoxic Activity of Bordetella pertussis, Infection and Immunity, vol. 74, No. 10, (Oct. 1, 2006), pp. 5574-5585.
Geurtsen et al: Consequences of the expression of lipopolysaccharide-modifying enzymes for the efficacy and reactogenicity of whole-cell pertussis vaccines, Microbes and Infection, vol. 9, No. 9, (Aug. 23, 2007) , pp. 1096-1103.
Steeghs Liana et al: Expression of foreign LpxA acyl transferases in Neisseria meningitidis results in modified lipid A with reduced toxicity and retained adjuvant activity., Cellular Microbiology, vol. 4, No. 9, (Sep. 2002), pp. 599-611.
W Strittmatter et al: "Copyright 0 1983, American Society for Microbiology Nontoxic Lipopolysaccharide from Rhodopseudomonas sphaeroides ATCC 17023", Journal of Bacteriology, (Jul. 1, 1983), pp. 153-158.
J. Arenas et al: Coincorporation of LpxLI and PagL Mutant Lipopolysaccharides into Liposomes with Neisseria meningitidis Opacity Protein: Influence on Endotoxic and Adjuvant Activity, Clinical and Vaccine Immunology, vol. 17, No. 4, (Apr. 1, 2010), pp. 487-495.
Raetz C R H et al: Lipopolysaccharide Endotoxins, Annual Review of Biochemistry, Palto Alto, CA, US, vol. 71, Jan. 1, 2002 (Jan. 1, 2002), pp. 635-700.

* cited by examiner

*Primary Examiner* — Mary Maille Lyons
(74) *Attorney, Agent, or Firm* — N.V. Nederlandsch Octrooibureau

(57) ABSTRACT

The current invention lies in the field of medicine and more specifically in the field of vaccinology. The current invention concerns a novel *Bordetella* LPS and a modified bacterium of the genus *Bordetella* comprising such modified LPS. The LPS of the invention has a reduced endotoxicity in comparison to an unmodified *Bordetella* LPS. The modified LPS of the invention is therefore particularly suitable for use in inducing or stimulating an immune response in a subject, wherein the immune response is induced or stimulated against a *Bordetella* infection. The modified *Bordetella* LPS of the invention is obtainable by introducing in a *Bordetella* cell the expression of a heterologous acyl transferase. In particular, the modified *Bordetella* cell of the invention has an increased expression of an heterologous LpxA, LpxL or LpxD acyl transferase.

23 Claims, 9 Drawing Sheets

Specification includes a Sequence Listing.

Wild Type

+LpxA$_{(Nm)}$ Δ*lpxA*

C10 OH
C14
C14 OH
C10 OH
C14 OH

+LpxA$_{(Pa)}$ Δ*lpxA*

C14 OH
C12
C14 OH
C10 OH
C14 OH

+LpxL$_{(Nm)}$ Δ*lpxL*

+LpxL(Pg) Δ*lpxL*

Δ*lpxD* + LpxDPa

SEQUENCE LISTING

```
<160> NUMBER OF SEQ ID NOS: 32

<210> SEQ ID NO 1
<211> LENGTH: 258
<212> TYPE: PRT
<213> ORGANISM: Pseudomonas aeruginosa

<400> SEQUENCE: 1

Met Ser Leu Ile Asp Pro Arg Ala Ile Ile Asp Pro Ser Ala Arg Leu
1               5                   10                  15

Ala Ala Asp Val Gln Val Gly Pro Trp Ser Ile Val Gly Ala Glu Val
            20                  25                  30

Glu Ile Gly Glu Gly Thr Val Ile Gly Pro His Val Val Leu Lys Gly
        35                  40                  45

Pro Thr Lys Ile Gly Lys His Asn Arg Ile Tyr Gln Phe Ser Ser Val
    50                  55                  60

Gly Glu Asp Thr Pro Asp Leu Lys Tyr Lys Gly Glu Pro Thr Arg Leu
65                  70                  75                  80

Val Ile Gly Asp His Asn Val Ile Arg Glu Gly Val Thr Ile His Arg
                85                  90                  95

Gly Thr Val Gln Asp Arg Ala Glu Thr Thr Ile Gly Asp His Asn Leu
            100                 105                 110

Ile Met Ala Tyr Ala His Ile Gly His Asp Ser Val Ile Gly Asn His
        115                 120                 125

Cys Ile Leu Val Asn Asn Thr Ala Leu Ala Gly His Val His Val Asp
    130                 135                 140

Asp Trp Ala Ile Leu Ser Gly Tyr Thr Leu Val His Gln Tyr Cys Arg
145                 150                 155                 160
```

```
Ile Gly Ala His Ser Phe Ser Gly Met Gly Ser Ala Ile Gly Lys Asp
                165                 170                 175

Val Pro Ala Tyr Val Thr Val Phe Gly Asn Pro Ala Glu Ala Arg Ser
            180                 185                 190

Met Asn Phe Glu Gly Met Arg Arg Arg Gly Phe Ser Ser Glu Ala Ile
        195                 200                 205

His Ala Leu Arg Arg Ala Tyr Lys Val Val Tyr Arg Gln Gly His Thr
    210                 215                 220

Val Glu Glu Ala Leu Ala Glu Leu Ala Glu Ser Ala Ala Gln Phe Pro
225                 230                 235                 240

Glu Val Ala Val Phe Arg Asp Ser Ile Gln Ser Ala Thr Arg Gly Ile
                245                 250                 255

Thr Arg


<210> SEQ ID NO 2
<211> LENGTH: 289
<212> TYPE: PRT
<213> ORGANISM: Neisseria meningitidis

<400> SEQUENCE: 2

Met Lys Phe Ile Phe Phe Val Leu Tyr Val Leu Gln Phe Leu Pro Phe
1               5                   10                  15

Ala Leu Leu His Lys Ile Ala Asp Leu Thr Gly Leu Leu Ala Tyr Leu
            20                  25                  30

Leu Val Lys Pro Arg Arg Arg Ile Gly Glu Ile Asn Leu Ala Lys Cys
        35                  40                  45

Phe Ser Glu Trp Ser Glu Glu Lys Arg Lys Thr Val Leu Lys Gln His
    50                  55                  60

Phe Lys His Met Ala Lys Leu Met Leu Glu Tyr Gly Leu Tyr Trp Tyr
65                  70                  75                  80

Ala Pro Ala Gly Arg Leu Lys Ser Leu Val Arg Tyr Arg Asn Lys His
                85                  90                  95

Tyr Leu Asp Asp Ala Leu Ala Ala Gly Glu Lys Val Ile Ile Leu Tyr
            100                 105                 110

Pro His Phe Thr Ala Phe Glu Met Ala Val Tyr Ala Leu Asn Gln Asp
        115                 120                 125

Ile Pro Leu Ile Ser Met Tyr Ser His Gln Lys Asn Lys Ile Leu Asp
    130                 135                 140

Glu Gln Ile Leu Lys Gly Arg Asn Arg Tyr His Asn Val Phe Leu Ile
145                 150                 155                 160

Gly Arg Thr Glu Gly Leu Arg Ala Leu Val Lys Gln Phe Arg Lys Ser
                165                 170                 175

Ser Ala Pro Phe Leu Tyr Leu Pro Asp Gln Asp Phe Gly Arg Asn Asp
            180                 185                 190

Ser Val Phe Val Asp Phe Phe Gly Ile Gln Thr Ala Thr Ile Thr Gly
        195                 200                 205

Leu Ser Arg Ile Ala Ala Leu Ala Asn Ala Lys Val Ile Pro Ala Ile
    210                 215                 220

Pro Val Arg Glu Ala Asp Asn Thr Val Thr Leu His Phe Tyr Pro Ala
225                 230                 235                 240

Trp Lys Ser Phe Pro Gly Glu Asp Ala Lys Ala Asp Ala Gln Arg Met
                245                 250                 255

Asn Arg Phe Ile Glu Asp Arg Val Arg Glu His Pro Glu Gln Tyr Phe
            260                 265                 270
```

Trp Leu His Lys Arg Phe Lys Thr Arg Pro Glu Gly Ser Pro Asp Phe
275 280 285

Tyr

<210> SEQ ID NO 3
<211> LENGTH: 288
<212> TYPE: PRT
<213> ORGANISM: Porphyromonas gingivalis

<400> SEQUENCE: 3

Met Gln Ala Val Leu Pro Leu Trp Met Val Arg Leu Gln Ser Arg Ile
1 5 10 15

Leu Ala Gly Leu Leu His Thr Val Val Arg Tyr Arg Arg Lys Val Val
20 25 30

Arg Asp Asn Leu Thr Arg Cys Phe Pro Glu Lys Ser Leu Gln Glu Ile
35 40 45

Arg Arg Ile Glu Arg Arg Phe Tyr Tyr Asn Phe Thr Tyr Gln Ile Leu
50 55 60

Ser Ser Phe Lys Leu Leu Thr Tyr Ser Gln Thr Gln Leu Arg Arg His
65 70 75 80

Ile Ser Phe Glu Asn Leu Asp Val Leu Ile Arg Leu Arg Ala Glu Gly
85 90 95

His Pro Ala Ile Leu Leu Met Met Gly His Phe Gly Asn Trp Glu Tyr
100 105 110

Phe Ser Gly Ser Gln Ala Ile Ile Lys Asp Leu Gly Leu Gln Ile Tyr
115 120 125

Gln Ile Phe Arg Pro Leu Lys Ser Thr Ser Ser Asp Arg Leu Met His
130 135 140

Arg Ile Arg Glu Arg Phe Gly Ser Arg Gly Ile Ala Lys His Asp Val
145 150 155 160

Pro Arg Glu Leu Leu Arg Leu Val Arg Asn Pro Ile Pro Thr Glu Thr
165 170 175

Pro Leu Val Ile Phe Ile Ala Asp Gln Ser Pro Ala Tyr Ala Gly Ser
180 185 190

Tyr Trp Thr Thr Phe Phe Gly Arg Glu Thr Ala Phe Phe Asn Gly Thr
195 200 205

Glu Lys Leu Gly His Lys Phe Ser Leu Pro Val Val Tyr Met Asp Val
210 215 220

Glu Lys Thr Gly His Asp Val Phe Thr Gly Thr Ile Lys Leu Leu His
225 230 235 240

His Pro Gln Asp Asp Ser Pro Glu Gly Ser Ile Thr Glu Glu Tyr Val
245 250 255

Arg Leu Met Glu Ala Thr Ile Arg Arg Asp Pro Ser Gln Trp Leu Trp
260 265 270

Ser His Arg Arg Trp Lys Arg Pro Arg Leu His Asn Thr Arg Gln Pro
275 280 285

<210> SEQ ID NO 4
<211> LENGTH: 353
<212> TYPE: PRT
<213> ORGANISM: Pseudomonas aeruginosa

<400> SEQUENCE: 4

Met Met Ser Thr Leu Ser Tyr Thr Leu Gly Gln Leu Ala Ala His Val
1 5 10 15

Gly Ala Glu Val Arg Gly Asp Ala Asp Leu Pro Ile Gln Gly Leu Ala

```
            20                  25                  30

Thr Leu Gln Glu Ala Gly Pro Ala Gln Leu Ser Phe Leu Ala Asn Pro
        35                  40                  45

Gln Tyr Arg Lys Tyr Leu Pro Glu Ser Arg Ala Gly Ala Val Leu Leu
    50                  55                  60

Thr Ala Ala Asp Ala Asp Gly Phe Ala Gly Thr Ala Leu Val Val Ala
65                  70                  75                  80

Asn Pro Tyr Leu Ala Tyr Ala Ser Leu Ser His Leu Phe Asp Arg Lys
                85                  90                  95

Pro Lys Ala Ala Ala Gly Ile His Pro Thr Ala Ile Val Ala Ala Asp
            100                 105                 110

Ala Glu Val Asp Pro Ser Ala Ser Val Gly Ala Tyr Ala Val Ile Glu
        115                 120                 125

Ser Gly Ala Arg Ile Gly Ala Gly Val Ser Ile Gly Ala His Cys Val
    130                 135                 140

Ile Gly Ala Arg Ser Val Ile Gly Glu Gly Gly Trp Leu Ala Pro Arg
145                 150                 155                 160

Val Thr Leu Tyr His Asp Val Thr Ile Gly Ala Arg Val Ser Ile Gln
                165                 170                 175

Ser Gly Ala Val Ile Gly Gly Glu Gly Phe Gly Phe Ala Asn Glu Lys
            180                 185                 190

Gly Val Trp Gln Lys Ile Ala Gln Ile Gly Gly Val Thr Ile Gly Asp
        195                 200                 205

Asp Val Glu Ile Gly Ala Asn Thr Thr Ile Asp Arg Gly Ala Leu Ser
    210                 215                 220

Asp Thr Leu Ile Gly Asn Gly Val Lys Leu Asp Asn Gln Ile Met Ile
225                 230                 235                 240

Ala His Asn Val Gln Ile Gly Asp His Thr Ala Met Ala Ala Cys Val
                245                 250                 255

Gly Ile Ser Gly Ser Ala Lys Ile Gly Arg His Cys Met Leu Ala Gly
            260                 265                 270

Gly Val Gly Leu Val Gly His Ile Glu Ile Cys Asp Asn Val Phe Val
        275                 280                 285

Thr Gly Met Thr Met Val Thr Arg Ser Ile Thr Glu Pro Gly Ser Tyr
    290                 295                 300

Ser Ser Gly Thr Ala Met Gln Pro Ala Ala Glu Trp Lys Lys Ser Ala
305                 310                 315                 320

Ala Arg Ile Arg Gln Leu Asp Asp Met Ala Arg Arg Leu Gln Gln Leu
                325                 330                 335

Glu Lys Arg Leu Ala Ala Val Thr Ser Ser Gly Asp Ala Ser Ser Asp
            340                 345                 350

Ala


<210> SEQ ID NO 5
<211> LENGTH: 240
<212> TYPE: PRT
<213> ORGANISM: Neisseria meningitidis

<400> SEQUENCE: 5

Met Lys Pro Ala Tyr Phe Ile Ser Asp Leu His Leu Ser Glu Lys Gln
1               5                   10                  15

Pro Glu Leu Thr Ala Leu Leu Leu Arg Phe Leu Arg Ser Ser Ala Ala
            20                  25                  30

Arg Gln Ala Arg Ala Val Tyr Ile Leu Gly Asp Leu Phe Asp Phe Trp
```

```
        35                  40                  45

Val Gly Asp Asp Glu Val Ser Glu Leu Asn Thr Ser Val Ala Arg Glu
    50                  55                  60

Ile Arg Lys Leu Ser Asp Lys Gly Val Ala Val Phe Phe Val Arg Gly
65                  70                  75                  80

Asn Arg Asp Phe Leu Ile Gly Gln Asn Phe Cys Arg Gln Ala Gly Met
                85                  90                  95

Thr Leu Leu Pro Asp Tyr Ser Val Leu Asp Leu Phe Gly Cys Lys Thr
            100                 105                 110

Leu Ile Cys His Gly Asp Thr Leu Cys Thr Asp Asp Arg Ala Tyr Gln
        115                 120                 125

Arg Phe Arg Lys Ile Val His Arg Lys Arg Leu Gln Lys Leu Phe Leu
    130                 135                 140

Met Leu Pro Leu Lys Trp Arg Thr Arg Leu Ala Thr Lys Ile Arg Arg
145                 150                 155                 160

Val Ser Lys Met Glu Lys Gln Val Lys Pro Ala Asp Ile Met Asp Val
                165                 170                 175

Asn Ala Ala Phe Thr Ala Arg Gln Val Arg Ala Phe Gly Ala Glu Arg
            180                 185                 190

Leu Ile His Gly His Thr His Arg Glu His Ile His His Glu Asn Gly
        195                 200                 205

Phe Thr Arg Ile Val Leu Gly Asp Trp His Asn Asp Tyr Ala Ser Ile
    210                 215                 220

Leu Arg Val Asp Gly Asp Gly Ala Val Phe Val Pro Leu Glu Lys Tyr
225                 230                 235                 240


<210> SEQ ID NO 6
<211> LENGTH: 258
<212> TYPE: PRT
<213> ORGANISM: Neisseria meningitidis

<400> SEQUENCE: 6

Met Thr Leu Ile His Pro Thr Ala Val Ile Asp Pro Lys Ala Glu Leu
1               5                   10                  15

Asp Ser Gly Val Lys Val Gly Ala Tyr Thr Val Ile Gly Pro Asn Val
            20                  25                  30

Gln Ile Gly Ala Asn Thr Glu Ile Gly Pro His Ala Val Ile Asn Gly
        35                  40                  45

His Thr Ser Ile Gly Glu Asn Asn Arg Ile Phe Gln Phe Ala Ser Leu
    50                  55                  60

Gly Glu Ile Pro Gln Asp Lys Lys Tyr Arg Asp Glu Pro Thr Lys Leu
65                  70                  75                  80

Ile Ile Gly Asn Gly Asn Thr Ile Arg Glu Phe Thr Thr Phe Asn Leu
                85                  90                  95

Gly Thr Val Thr Gly Ile Gly Glu Thr Arg Ile Gly Asp Asp Asn Trp
            100                 105                 110

Ile Met Ala Tyr Cys His Leu Ala His Asp Cys Val Ile Gly Asn His
        115                 120                 125

Thr Ile Phe Ala Asn Asn Ala Ser Leu Ala Gly His Val Thr Ile Gly
    130                 135                 140

Asp Tyr Val Val Leu Gly Gly Tyr Thr Leu Val Phe Gln Phe Cys Arg
145                 150                 155                 160

Ile Gly Asp Tyr Ala Met Thr Ala Phe Ala Ala Gly Val His Lys Asp
                165                 170                 175
```

-continued

```
Val Pro Pro Tyr Phe Met Ala Ser Gly Tyr Arg Ala Glu Pro Ala Gly
            180                 185                 190

Leu Asn Ser Glu Gly Met Arg Arg Asn Gly Phe Thr Ala Glu Gln Ile
        195                 200                 205

Ser Ala Val Lys Asp Val Tyr Lys Thr Leu Tyr His Arg Gly Ile Pro
    210                 215                 220

Phe Glu Glu Ala Lys Ala Asp Ile Leu Arg Arg Ala Glu Thr Gln Ala
225                 230                 235                 240

Glu Leu Ala Val Phe Arg Asp Phe Phe Ala Gln Ser Ala Arg Gly Ile
                245                 250                 255

Ile Arg


<210> SEQ ID NO 7
<211> LENGTH: 33
<212> TYPE: DNA
<213> ORGANISM: artificial
<220> FEATURE:
<223> OTHER INFORMATION: primer

<400> SEQUENCE: 7

aagcgcgcca tatgaccctc atccacccga ccg                                33


<210> SEQ ID NO 8
<211> LENGTH: 41
<212> TYPE: DNA
<213> ORGANISM: artificial
<220> FEATURE:
<223> OTHER INFORMATION: primer

<400> SEQUENCE: 8

aagcgcgcaa gctttcagcg gatgatgccg cgtgccgatt g                       41


<210> SEQ ID NO 9
<211> LENGTH: 31
<212> TYPE: DNA
<213> ORGANISM: artificial
<220> FEATURE:
<223> OTHER INFORMATION: primer

<400> SEQUENCE: 9

aagcgcgcca tatgagtttg atcgatcctc g                                  31


<210> SEQ ID NO 10
<211> LENGTH: 41
<212> TYPE: DNA
<213> ORGANISM: artificial
<220> FEATURE:
<223> OTHER INFORMATION: primer

<400> SEQUENCE: 10

aagcgcgaag cttatcagcg ggtgatgccg cgggttgcgc t                       41


<210> SEQ ID NO 11
<211> LENGTH: 34
<212> TYPE: DNA
<213> ORGANISM: artificial
<220> FEATURE:
<223> OTHER INFORMATION: primer

<400> SEQUENCE: 11

aacgcgcgca tatgaaattt atattttttg tact                               34


<210> SEQ ID NO 12
```

<211> LENGTH: 40
<212> TYPE: DNA
<213> ORGANISM: artificial
<220> FEATURE:
<223> OTHER INFORMATION: primer

<400> SEQUENCE: 12
aagcgcgcaa gctttcagta aaaatcgggg ctgccttccg 40

<210> SEQ ID NO 13
<211> LENGTH: 31
<212> TYPE: DNA
<213> ORGANISM: artificial
<220> FEATURE:
<223> OTHER INFORMATION: primer

<400> SEQUENCE: 13
aagcgcgcca tatgaaagcg acactttccc t 31

<210> SEQ ID NO 14
<211> LENGTH: 37
<212> TYPE: DNA
<213> ORGANISM: artificial
<220> FEATURE:
<223> OTHER INFORMATION: primer

<400> SEQUENCE: 14
aagcgcgcaa gctttcatag ttgtcgggta ttatgca 37

<210> SEQ ID NO 15
<211> LENGTH: 20
<212> TYPE: DNA
<213> ORGANISM: artificial
<220> FEATURE:
<223> OTHER INFORMATION: primer

<400> SEQUENCE: 15
gtccaaatcg gcgcgaatac 20

<210> SEQ ID NO 16
<211> LENGTH: 20
<212> TYPE: DNA
<213> ORGANISM: artificial
<220> FEATURE:
<223> OTHER INFORMATION: primer

<400> SEQUENCE: 16
ctttgacggc ggaaatctgc 20

<210> SEQ ID NO 17
<211> LENGTH: 20
<212> TYPE: DNA
<213> ORGANISM: artificial
<220> FEATURE:
<223> OTHER INFORMATION: primer

<400> SEQUENCE: 17
ccattggcga ccacaacctg 20

<210> SEQ ID NO 18
<211> LENGTH: 20
<212> TYPE: DNA
<213> ORGANISM: artificial
<220> FEATURE:
<223> OTHER INFORMATION: primer

<400> SEQUENCE: 18
tgccgaagac cgtcacgtag 20

<210> SEQ ID NO 19
<211> LENGTH: 20
<212> TYPE: DNA
<213> ORGANISM: artificial
<220> FEATURE:
<223> OTHER INFORMATION: primer

<400> SEQUENCE: 19
tgaaatcgct ggtgcgctac 20

<210> SEQ ID NO 20
<211> LENGTH: 20
<212> TYPE: DNA
<213> ORGANISM: artificial
<220> FEATURE:
<223> OTHER INFORMATION: primer

<400> SEQUENCE: 20
atcgggcaga tacagaaacg 20

<210> SEQ ID NO 21
<211> LENGTH: 20
<212> TYPE: DNA
<213> ORGANISM: artificial
<220> FEATURE:
<223> OTHER INFORMATION: primer

<400> SEQUENCE: 21
gtgctaccgc tatggatggt 20

<210> SEQ ID NO 22
<211> LENGTH: 20
<212> TYPE: DNA
<213> ORGANISM: artificial
<220> FEATURE:
<223> OTHER INFORMATION: primer

<400> SEQUENCE: 22
ctataccacg cgaaccgaat 20

<210> SEQ ID NO 23
<211> LENGTH: 20
<212> TYPE: DNA
<213> ORGANISM: artificial
<220> FEATURE:
<223> OTHER INFORMATION: primer

<400> SEQUENCE: 23
ctatgtggcg cggtattatc 20

<210> SEQ ID NO 24
<211> LENGTH: 20
<212> TYPE: DNA
<213> ORGANISM: artificial
<220> FEATURE:
<223> OTHER INFORMATION: primer

<400> SEQUENCE: 24
caactttatc cgcctccatc 20

<210> SEQ ID NO 25
<211> LENGTH: 178
<212> TYPE: PRT

<213> ORGANISM: Bordetella parapertussis

<400> SEQUENCE: 25

```
Met Gln Phe Leu Lys Lys Asn Lys Pro Leu Phe Gly Ile Val Thr Leu
1               5                   10                  15

Ala Leu Ala Cys Ala Thr Ala Gln Ala Gln Pro Thr Gln Gly Gly Val
            20                  25                  30

Ser Leu His Tyr Gly Ile Gly Asp His Tyr Gln Arg Val Thr Leu Asn
        35                  40                  45

Tyr Glu Thr Pro Thr Leu Trp Ser His Gln Phe Gly Gly Asn Trp Gly
    50                  55                  60

Arg Leu Asp Leu Thr Pro Glu Leu Gly Ala Ser Tyr Trp Trp Ala Asp
65                  70                  75                  80

Gly Ser Arg Ser Pro Gly His Val Trp Gln Ala Ser Ala Ile Pro Met
                85                  90                  95

Phe Arg Trp Trp Thr Gly Glu Arg Phe Tyr Ile Glu Ala Gly Ile Gly
            100                 105                 110

Ala Thr Val Phe Ser Ser Thr Ser Phe Ala Asp Lys Arg Ile Gly Ser
        115                 120                 125

Ala Phe Gln Phe Gly Asp His Ile Gly Leu Gly Phe Leu Leu Thr Pro
    130                 135                 140

Ser Asn Arg Ile Gly Leu Arg Tyr Ser His Phe Ser Asn Ala Gly Ile
145                 150                 155                 160

Lys Glu Pro Asn Pro Gly Leu Asp Ile Val Gln Leu Thr Tyr Thr Tyr
                165                 170                 175

Gln Phe
```

<210> SEQ ID NO 26
<211> LENGTH: 29
<212> TYPE: DNA
<213> ORGANISM: artificial
<220> FEATURE:
<223> OTHER INFORMATION: primer

<400> SEQUENCE: 26

```
cgcgcgcata tgatgagtac cttgtccta                                         29
```

<210> SEQ ID NO 27
<211> LENGTH: 60
<212> TYPE: DNA
<213> ORGANISM: artificial
<220> FEATURE:
<223> OTHER INFORMATION: primer

<400> SEQUENCE: 27

```
gcgcgcaagc ttttaatgat gatgatgatg atgatgatgg ccgccgcccg catcagatga     60
```

<210> SEQ ID NO 28
<211> LENGTH: 264
<212> TYPE: PRT
<213> ORGANISM: Bordetella pertussis

<400> SEQUENCE: 28

```
Met Ser Gly Asn Ile His Pro Thr Ala Val Val Asp Pro Ala Ala Gln
1               5                   10                  15

Ile Asp Ser Ser Val Val Ile Gly Pro Tyr Ser Val Val Gly Pro Gly
            20                  25                  30

Val Ser Ile Ala Ala Gly Thr Glu Val Gly Ala His Cys Val Leu Asp
        35                  40                  45
```

-continued

```
Gly Val Thr Ser Ile Gly Arg Asp Asn Arg Phe Tyr Arg Phe Cys Ser
    50                  55                  60

Ile Gly Gly Met Pro Gln Asp Lys Lys Tyr Ser Gly Glu Pro Thr Arg
65                  70                  75                  80

Leu Val Ile Gly Asp Arg Asn Thr Val Arg Glu Phe Thr Thr Phe Asn
                85                  90                  95

Thr Gly Thr Val Gln Asp Gly Gly Val Thr Ser Ile Gly Asp Asp Asn
            100                 105                 110

Trp Ile Met Ala Tyr Val His Ile Ala His Asp Cys His Ile Gly Asn
        115                 120                 125

Asn Thr Ile Leu Ala Asn Ser Val Gln Leu Gly Gly His Val Gln Val
    130                 135                 140

Gly Asp Trp Ala Ile Val Gly Gly Leu Thr Gly Val His Gln Phe Ala
145                 150                 155                 160

Lys Ile Gly Ala His Ser Met Thr Gly Gly Asn Ser Ser Leu Met Gln
                165                 170                 175

Asp Ala Pro Pro Phe Val Leu Ala Ala Gly Asn Pro Cys Arg Pro Val
            180                 185                 190

Gly Val Asn Val Glu Gly Leu Lys Arg Arg Gly Phe Ser Ala Ala Ala
        195                 200                 205

Ile Ser Ala Leu Arg Asp Ala Tyr Lys Ser Ile Tyr Arg Arg Gly Leu
    210                 215                 220

Ser Leu Asp Glu Gly Arg Ala Glu Leu Arg Ala Arg Gln Gln Ala Glu
225                 230                 235                 240

Pro Asp Val Ala Glu His Leu Gln Thr Met Leu Asp Phe Leu Asp Ala
                245                 250                 255

Ser Thr Arg Gly Ile Ile Arg Pro
            260


<210> SEQ ID NO 29
<211> LENGTH: 363
<212> TYPE: PRT
<213> ORGANISM: Bordetella pertussis

<400> SEQUENCE: 29

Met Pro Val Leu Leu Asp Pro Glu Asn Ala Leu Ala Leu Asp Val Leu
1               5                   10                  15

Leu Ala Gly Ile Asp Ala Gln Gly Leu Asp Trp His Leu Ser Ala Pro
            20                  25                  30

Asp Ala Ala Asp Leu Pro Arg Ile Arg Gly Ile Gly Thr Leu Ser Ser
        35                  40                  45

Ala Gly Asn Glu Glu Ile Ser Phe Leu Ser Asn Pro Arg Tyr Gln Asn
    50                  55                  60

Gln Leu Ala Thr Thr Arg Ala Ala Ala Val Ile Val Thr Pro Asp Val
65                  70                  75                  80

Ala Gln Ala Arg Gln Glu Gln Gly Ala Ser Gly His Val Leu Val Val
                85                  90                  95

Cys Lys His Pro Tyr Leu Leu Tyr Ala Arg Leu Ala Gln Trp Phe Glu
            100                 105                 110

Arg Ala Ser Arg Pro Ala Gly Pro Ala Gly Val His Pro Ser Ala Val
        115                 120                 125

Val Asp Pro Ser Ala Glu Ile Asp Ala Asp Val Arg Val Gly Ala Gln
    130                 135                 140

Cys Val Ile Glu Ala Gly Ala Arg Ile Gly Arg Gly Ala Arg Leu Gly
```

145 150 155 160

Pro Gly Cys Val Ile Gly Ala Gly Ser Thr Val Gly Ala Asp Ser Leu
165 170 175

Leu His Pro Arg Val Thr Leu Tyr Ala Gly Val His Val Gly Glu Arg
180 185 190

Ala Ile Ile His Ser Gly Ala Val Leu Gly Ala Asp Gly Phe Gly Phe
195 200 205

Ala Pro Asp Pro Thr Leu Gly Arg Gly Ala Trp Gly Lys Ile Pro Gln
210 215 220

Leu Gly Glu Val Arg Val Gly Asn Asp Val Glu Ile Gly Ala Asn Thr
225 230 235 240

Thr Ile Asp Arg Gly Ala Leu Asp Asp Thr Ile Val Gly Asp Gly Val
245 250 255

Lys Leu Asp Asn Gln Ile Met Val Ala His Asn Val Arg Ile Gly Ala
260 265 270

His Thr Ala Ile Ala Ala Cys Val Gly Ile Ala Gly Ser Thr Thr Ile
275 280 285

Gly Glu Arg Cys Thr Ile Gly Gly Ala Ser Met Leu Ser Gly His Leu
290 295 300

Ala Ile Ala Asp Asp Val Asn Ile Ser Gly Gly Thr Ala Val Thr Ser
305 310 315 320

Asn Ile Ala Lys Ala Gly Arg Tyr Thr Gly Val Tyr Pro Tyr Ala Glu
325 330 335

His Ser Glu Trp Gln Arg Asn Ala Ala Val Ile Gln Gln Leu Ala Leu
340 345 350

Leu Arg Arg Arg Leu Arg Ala Leu Glu Arg Glu
355 360

<210> SEQ ID NO 30
<211> LENGTH: 249
<212> TYPE: PRT
<213> ORGANISM: Bordetella pertussis

<400> SEQUENCE: 30

Met Trp Leu Ala Ser Asp Leu His Leu Gly Pro Ala Thr Pro Ala Thr
1 5 10 15

Ala Glu Ala Phe Leu Gly Leu Leu Gln Ala Ala Ala Asp Glu Ala Ser
20 25 30

Ala Leu Leu Leu Pro Gly Asp Ile Phe Asp Ala Trp Ile Gly Asp Asp
35 40 45

Val Ile Arg Ala Ala Pro Pro Trp Leu Ala Ala Val Leu His Gly Ile
50 55 60

Arg Ala Ala Ala Gly Arg Ile Pro Val Tyr Leu Gly Arg Gly Asn Arg
65 70 75 80

Asp Phe Leu Ile Gly Gln Glu Leu Ala Asp Ala Leu Gly Ala His Leu
85 90 95

Leu Pro Glu Pro Val Leu Leu Glu Thr Asp Tyr Gly Arg Ile Leu Leu
100 105 110

Thr His Gly Asp Glu Tyr Cys Thr Asp Asp Ser Ala Tyr Gln Gln Phe
115 120 125

Arg Ala Met Val Arg Asn Pro Gln Trp Gln Ala Gln Phe Leu Ala Lys
130 135 140

Ser Ile Pro Glu Arg Leu Ala Met Ala Glu Gln Ala Arg Gly Glu Ser
145 150 155 160

-continued

```
Gln Ala Ala Asn Gln Ala Lys Ser Met Glu Ile Met Asp Val Asn Pro
                165                 170                 175

Ala Ala Val Glu Ala Ala Leu Arg Glu Ala Asp Val Asp Val Leu Val
            180                 185                 190

His Gly His Thr His Arg Pro Ala Arg His Val Leu Ser Val Asp Gly
        195                 200                 205

Arg Lys Arg Glu Arg Trp Val Leu Pro Asp Trp Asp Cys Asp His Ala
    210                 215                 220

Asp Pro Pro Arg Gly Gly Trp Leu Val Ile Asp Arg Asp Gly Leu Gln
225                 230                 235                 240

Cys Phe Asp Leu Val Glu Asp Glu Asp
                245
```

<210> SEQ ID NO 31
<211> LENGTH: 296
<212> TYPE: PRT
<213> ORGANISM: Bordetella pertussis

<400> SEQUENCE: 31

```
Met Ser Gln Phe Lys Thr Arg Ala Leu Thr Ala Met Leu Arg Gly Phe
1               5                   10                  15

Ala Arg Met Arg Pro Ala Thr Arg Gln Arg Ala Gly Ala Leu Val Gly
            20                  25                  30

Trp Leu Ser Tyr Arg Leu Ala Arg Ser Arg Val Arg Ile Val Arg Arg
        35                  40                  45

Asn Leu Glu Leu Cys Phe Pro Gly Gln Pro Glu Ala Val Arg Glu Arg
    50                  55                  60

Trp Thr Arg Glu His Phe Arg Ala Leu Gly Gln Ser Ile Val Asp Arg
65                  70                  75                  80

Gly Val Leu Trp Tyr Gly Ser Pro Glu Ala Val Arg Glu Met Val Thr
                85                  90                  95

Gln Thr Gly Ala Glu Arg Ile Asn Ala Leu Ile Ala Ala Gly Arg Pro
            100                 105                 110

Val Ile Leu Leu Ala Pro His Phe Val Ala Leu Asp Ala Ala Ala Thr
        115                 120                 125

Arg Leu Thr Met Glu Val Pro Ser Gly Ala Thr Met Tyr Thr Pro Gln
    130                 135                 140

Ser Asp Pro Ala Val Asp Ala Ile Val Arg Ala Gly Arg Ala Arg Phe
145                 150                 155                 160

Asn Glu Val Phe Leu Val Ser Arg Lys Asp Gly Val Arg Asp Leu Val
                165                 170                 175

Arg His Leu Arg Glu Pro Arg Pro Val Tyr Tyr Leu Pro Asp Met Asp
            180                 185                 190

Phe Gly Arg Ala Gly Ser Ile Phe Val Pro Phe Phe Gly Val Pro Ala
        195                 200                 205

Ala Thr Leu Leu Ala Thr Ala Gln Leu Ala Arg Lys Trp Asn Ala Ala
    210                 215                 220

Val Leu Pro Ile Leu Asp Phe Trp Asp Pro Arg Thr Gly Arg Tyr His
225                 230                 235                 240

Val Glu Val Leu Pro Glu Leu Pro Asp Phe Pro Gly Asp Gly Ser Leu
                245                 250                 255

Glu Asp Ala Thr Thr Arg Leu Asn Arg Glu Leu Glu Ser Trp Val Leu
            260                 265                 270

Arg Cys Pro Ser Gln Tyr Tyr Trp Val His Arg Arg Phe Lys Thr Arg
        275                 280                 285
```

```
Pro Leu Gly Lys Pro Lys Leu Tyr
    290                 295


<210> SEQ ID NO 32
<211> LENGTH: 468
<212> TYPE: PRT
<213> ORGANISM: Pseudomonas aeruginosa

<400> SEQUENCE: 32

Met Ser Ala Trp Arg His Leu Ser Leu Trp Met Asn Gln Leu Asp Asp
1               5                   10                  15

Pro Leu Glu Ala Arg Pro Ser Leu Glu Glu Ser Leu Glu Val Asp Val
            20                  25                  30

Ala Ile Val Gly Ala Gly Tyr Thr Gly Leu Trp Thr Ala Tyr Tyr Leu
        35                  40                  45

Lys Arg Arg Ala Pro Gln Leu Arg Val Ala Ile Val Glu Ala Glu Thr
    50                  55                  60

Ala Gly Phe Gly Ala Ser Gly Arg Asn Gly Gly Trp Leu Met Gly Asn
65                  70                  75                  80

Leu Leu Gly Glu Asp Gly Leu Leu Ala Gly Leu Pro Pro Glu Arg Arg
                85                  90                  95

Arg Ala Gly Tyr Asp Leu Leu His Gly Ile Pro Asp Glu Val Ala Arg
            100                 105                 110

Val Leu Gln Glu Glu Gly Ile Asp Cys Asp Tyr Arg Lys Gly Gly Val
        115                 120                 125

Leu Tyr Cys Ala Ala Arg Tyr Pro Glu Gln Glu Arg Arg Leu Arg Ala
    130                 135                 140

Tyr Leu His Asp Leu Tyr Ala Glu Gly Leu Asp Glu Ser Asp Tyr Arg
145                 150                 155                 160

Trp Leu Thr Pro Gln Glu Leu Asp Gln Gln Leu Arg Ile Pro Gly Ser
                165                 170                 175

Tyr Gly Ala Ile His Ser Pro His Cys Ala Thr Ile Gln Pro Ala Arg
            180                 185                 190

Leu Ala Arg Gly Leu Ala Arg Ala Val Glu Arg Leu Gly Val Arg Leu
        195                 200                 205

Phe Glu Lys Ser Arg Val Leu His Trp Gln Arg Gly Leu Leu Arg Thr
    210                 215                 220

Glu Arg Gly Glu Leu Arg Ala Glu Trp Ile Val Pro Ala Val Glu Gly
225                 230                 235                 240

Tyr Ala Ala Ser Leu Pro Pro Leu Gly His Tyr Gln Leu Pro Val Gln
                245                 250                 255

Ser Leu Leu Val Ala Thr Glu Pro Leu Pro Ser Ser Val Trp Ala Glu
            260                 265                 270

Ile Gly Leu Glu Arg Gly Gln Ala Phe Ser Glu Phe Ser Arg Gln Val
        275                 280                 285

Thr Tyr Gly Gln Arg Thr Ala Asp Asp Arg Leu Ala Phe Gly Ala Arg
    290                 295                 300

Gly Gly Tyr Arg Phe Gly Gly Lys Leu Arg Ser Asp Phe Ser Leu Asp
305                 310                 315                 320

Asp Glu Glu Val Gly Leu Arg Arg Tyr Leu Phe Gly Glu Leu Phe Pro
                325                 330                 335

Leu Leu Lys Asp Ala Arg Ile Ser His Thr Trp Gly Gly Asn Leu Gly
            340                 345                 350

Met Ala Arg Arg Phe Arg Pro His Met Leu Leu Asp Arg Ala Ser Gly
```

-continued

```
        355                 360                 365

Ile Ala Leu Ser Gly Gly Tyr Gly Gly Glu Gly Val Gly Ala Ser Asn
    370                 375                 380

Leu Gly Gly Arg Thr Leu Ala Ala Leu Ile Leu Gly Glu Asp Ser Glu
385                 390                 395                 400

Leu Leu Arg Gln Pro Trp Val Leu Gly Glu Arg Pro Leu Asp Ser Leu
                405                 410                 415

Ala Arg Trp Glu Pro Glu Pro Cys Arg Trp Leu Gly Tyr Asn Ala Ile
            420                 425                 430

Ile Arg Ser Phe Val His Glu Asp Arg Val Leu Ala Asp Pro His Ser
        435                 440                 445

Ala Pro Trp Arg Arg Ser Leu Ala Gln Thr Leu Ala Ala Gly Met Glu
    450                 455                 460

Ser Leu Met Arg
465
```

BORDETELLA VACCINES COMPRISING LPS WITH REDUCED REACTOGENICITY

FIELD OF THE INVENTION

The present invention lies in the field of vaccinology and in particular in the field of the prevention or treatment of a *Bordetella* infection.

The current invention pertains to a *Bordetella* LPS with a lowered endotoxicity, and a genetically modified bacterium of the genus *Bordetella* comprising such modified LPS. The invention further relates to an outer membrane vesicle (OMV) obtainable from said modified bacterium. The invention also concerns compositions comprising said LPS, genetically modified bacterium and/or OMV and the use of said composition as a medicament. The invention further concerns said composition for use in a treatment comprising inducing or stimulating an immune response in a subject.

BACKGROUND ART

*Bordetella pertussis* is a gram-negative bacterium and an obligate human pathogen that causes pertussis, an acute respiratory tract disease also known as whooping cough. Several vaccine formulations have been developed against pertussis. A whole cell pertussis vaccine that was introduced in the fifties of the previous century was effective but generated unacceptable side effects. Therefore, it is currently out of the market in the industrialized countries. Subunit-based vaccines replaced the whole cell vaccines as they were shown to be safe and to confer relative protection (55-95% of coverage) against the disease. However, the fast adaptation of the pathogen and the rapid waning of immunity, amongst others, are reducing the efficacy of these formulations. This became especially alarming in the industrialized countries in the last decades, which have witnessed a considerable increase in the number of cases including amongst vaccinees [1]. Thus, there is a strong medical need for a new, safe, and effective vaccine formula. A strategy to reach this goal could be the introduction of new whole cell vaccines with reduced toxicity. As toxicity is mainly determined by the lipid A moiety of lipopolysaccharides (LPS) [2], this approach requires lipid A engineering.

LPS is a major component of outer membrane of gram-negative bacteria. It consists of a lipid A moiety, a core oligosaccharide, and a long polysaccharide known as the O-antigen, which, however, is lacking in some species including *B. pertussis* [3-5]. The lipid A moiety is recognized by the mammalian LPS receptor, the TLR4/MD-2 complex, resulting in activation of a signaling cascade that ends in the production of pro-inflammatory cytokines and chemokines [6]. These mediators activate the immune defenses [7; 8], but overstimulation causes a variety of disorders with often fatal consequences [9]. Thus, LPS can act as adjuvant but also as a potent endotoxin. Lipid A of *Escherichia coli* consists of a glucosamine disaccharide that is phosphorylated at the 1 and 4' positions and contains four hydroxylated fatty acyl chains linked via an amide linkage to the 2 and 2' positions and via an ester bond to the 3 and 3' positions. Two secondary acyl chains are esterified to the hydroxyl groups of the fatty acids at the 2' and 3' positions [4]. The biosynthetic pathway of lipid A requires nine well-conserved enzymes [4]. In the first step, a 3-hydroxyl acyl chain is transferred from acyl carrier protein to the 3 position of N-acetylglucosamine (GlcNAc) in the activated sugar UDP-GlcNAc by LpxA [10; 11]. The resulting product is then de-acetylated by LpxC and subsequently acylated with a 3-hydroxyl acyl chain at the 2 position by LpxD. LpxH then removes a UMP molecule from a proportion of the resulting molecules and one modified molecule is linked with an unmodified one by LpxB. The resulting product is phosphorylated at 4' position by LpxK to create the tetra-acylated and bis-phosphorylated lipid IVA. Two 3-deoxy-D-manno-oct-2-ulosonic acid (KDO) residues are then added to the 6' position by WaaA after which the secondary acyl chains are added by the LpxL and LpxM acyl transferases.

Variations in the lipid A structure are found in different bacterial species. These variations affect the activation of the LPS receptor. Particularly, the number and length of the acyl chains as well as the number of phosphate groups could all determine the strength of activation [4; 12; 13].

Variation in the acyl-chain length is determined by molecular rulers in the acyl transferases LpxA, LpxD, LpxL and LpxM, which vary between these enzymes of different bacterial species [14]. Furthermore, after the conserved biosynthesis pathway, modifications can be introduced in the lipid A during or after its transport to the outer membrane by enzymes located in the inner or outer membrane. These modifications include acylation, de-acylation and de-phosphorylation and the presence of these enzymes differs between bacterial species [15].

Lipid A of *B. pertussis* (FIG. 1A) differs from that of *E. coli* in that it is penta-acylated: it misses a secondary acyl chain linked to the primary acyl chain at the 3' position. Furthermore, the remaining secondary acyl chain is a C14 instead of a C12 as found in *E. coli* and, curiously, the primary hydroxylated acyl chains at the 3 and 3' positions differ in length (FIG. 1A) even though they are added by the same LpxA enzyme.

It was reported previously that *Bordetella* 3-O-deacylated LPS reduces LPS toxicity (see e.g. WO 2006/065139). Nevertheless, the decreased toxicity of *B. pertussis* LPS that had lost the primary acyl chain at the 3 position was nullified in whole-cell preparations by its increased release from the membranes [2].

There is therefore still a strong need in the art for a *Bordetella* LPS having a reduced endotoxicity. In particular, there is a need for *Bordetella* species having such LPS with reduced endotoxicity. Preferably the endotoxicity of the LPS is sufficiently low to be suitable for use in the prevention or treatment of a *Bordetella* infection. More precisely, there is still a need in the art for a whole cell *Bordetella* vaccine comprising LPS with a lowered endotoxicity,

SUMMARY OF THE INVENTION

In a first aspect, the invention pertains to a *Bordetella* LPS having a lipid A moiety that is modified as compared to the lipid A moiety of a wild-type *Bordetella* LPS in that the length of at least one acyl chain is shorter.

Preferably, the length of the acyl chain at the 3 position of the modified lipid A moiety does not have a greater length than the acyl chain of the wild-type *Bordetella* lipid A moiety at the same 3 position, and preferably the length of the acyl chain at the 3 position of the modified lipid A moiety is not greater than $C_{10}$. Preferably, the length of the acyl chain at the 3 position of the modified lipid A moiety has the same length as the acyl chain of the wild-type *Bordetella* lipid A moiety at the same 3 position, and preferably the length of the acyl chain at the 3 position is $C_{10}$.

In a preferred embodiment of the invention, the length of the acyl chain at the 3 position of the modified lipid A moiety is the same as the length of the acyl chain at the 3' position.

Preferably, the shorter acyl chain is selected from the group consisting of: i) the acyl chain at the 3' position of the lipid A moiety; ii) the primary acyl chain at the 2' position of the lipid A moiety; iii) the secondary acyl chain at the 2' position of the lipid A moiety; and iv) the acyl chain at the 2 position of the Lipid A moiety. Preferably, the acyl chain is at least two, four or six C atoms shorter. In a further preferred embodiment, the invention concerns a *Bordetella* LPS as defined herein, wherein, except for the modified lipid A moiety, the LPS has the structure of *Bordetella pertussis, Bordetella parapertussis* or *Bordetella bronchiseptica*. Preferably the LPS, except for the modified lipid A moiety, has the structure of *Bordetella pertussis.*

In a further preferred embodiment, the invention relates to a *Bordetella* LPS as defined herein, wherein the modified lipid A moiety has the structure of formula (I):

General formula (I)

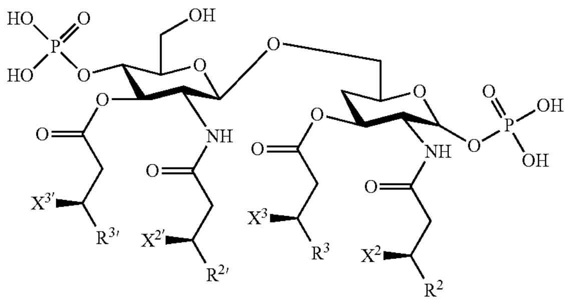

wherein $X^2$, $X^3$, $X^{2'}$, $X^{3'}$, $R^2$, $R^3$, $R^{2'}$, and $R^{3'}$ are each independently selected from the group consisting of —H, —OH, —Y, —O—(C═O)—CH(OH)—Y, and —O—(C═O)—Y, wherein Y is an alkyl moiety of general formula $-(CH_2)_n-H$, and n is an integer that for each instance of Y is independently chosen from 1, 2, 3, 4, 5, 6, 7, 8, 9, 10, 11, 12, 13, 14, or 15.

In a second aspect, the invention concerns a genetically modified bacterium of the genus *Bordetella*, wherein the bacterium comprises an LPS as defined herein. Preferably, the bacterium is modified compared to the wild-type *Bordetella bacterium* in that it has a genetic modification that introduces a heterologous acyl transferase activity. Preferably, the genetic modification that introduces heterologous acyl transferase activity confers to the cell at least one of a heterologous LpxA, LpxL and LpxD acyl transferase activity. Preferably, the genetic modification introduces the expression of at least one of a heterologous lpxA, a lpxL, and a lpxD gene, wherein i) the lpxA gene has a nucleotide sequence that encodes a LpxA acyl transferase that has at least 60% amino acid sequence identity with SEQ ID NO: 1; ii) the lpxL gene has a nucleotide sequence that encodes a LpxL acyl transferase that has at least 60% amino acid sequence identity with SEQ ID NO: 2; and/or iii) the lpxD gene has a nucleotide sequence that encodes a LpxD acyl transferase that has at least 60% amino acid sequence identity with SEQ ID NO: 4

Preferably, the modified bacterium further comprises a genetic mutation that reduces or eliminates the activity of LpxA and/or LpxD acyl transferase encoded by an endogenous lpxA gene and/or an endogenous lpxD gene.

In a further preferred embodiment, the bacterium as defined herein is modified compared to the wild-type *Bordetella bacterium* in that it has a genetic modification that introduces a heterologous UDP-2,3-diacylglucosamine pyrophosphatase activity, wherein preferably the genetic modification introduces the expression of a heterologous lpxH gene and wherein preferably the lpxH gene has a nucleotide sequence that encodes a LpxH that has at least 60% amino acid sequence identity with SEQ ID NO: 5.

Preferably, the bacterium as defined herein is a genetically modified *Bordetella pertussis, Bordetella parapertussis* or *Bordetella bronchiseptica*, wherein preferably the genetically modified bacterium is a genetically modified *Bordetella pertussis* and most preferably a *Bordetella pertussis* B213 strain. Preferably, the genetically modified bacterium as defined herein additionally has a genetic modification that increases lipid A 3-O-deacylase activity.

In a further preferred embodiment, the invention pertains to a *Bordetella* LPS as defined herein, wherein the LPS is obtainable from the genetically modified bacterium as defined herein.

In a third aspect, the invention concerns an OMV comprising the *Bordetella* LPS as defined herein. Preferably, the OMV is obtainable from the genetically modified bacterium as defined herein.

In a fourth aspect, the invention pertains to a composition comprising at least one of a *Bordetella* LPS, a genetically modified bacterium and an OMV as defined herein.

In a fifth aspect, the invention concerns a composition as defined herein for use as a medicament.

In a sixth aspect, the invention concerns a composition as defined herein for use in a treatment comprising inducing or stimulating an immune response in a subject. Preferably, the immune response is induced or stimulated against a *Bordetella* infection, preferably a *Bordetella pertussis* infection. In a preferred embodiment, the treatment is the prevention or treatment of whooping cough. Preferably, the composition for a use as specified herein is a pharmaceutical composition further comprising a pharmaceutically accepted excipient.

Preferably, the composition for a use as specified herein is a whole cell vaccine comprising a bacterium as defined herein, wherein preferably the bacterium is inactivated.

In a preferred embodiment, the composition for a use as defined herein is an acellular vaccine comprising a *Bordetella* LPS as specified herein or an OMV as defined herein.

In a preferred embodiment, the composition for a use as defined herein further comprises at least one non-*Bordetella* antigen.

DESCRIPTION OF THE INVENTION

Definitions

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithm (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blosum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to acyl transferase nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at http://www.ncbi.nlm.nih.gov/.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, aspartate-glutamate and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; arg to lys; asn to gin or his; asp to glu; cys to ser or ala; gin to asn; glu to asp; gly to pro; his to asn or gin; ile to leu or val; leu to ile or val; lys to arg; gin or glu; met to leu or ile; phe to met, leu or tyr; ser to thr; thr to ser; trp to tyr; tyr to trp or phe; and, val to ile or leu.

As used herein, the term "selectively hybridizing", "hybridizes selectively" and similar terms are intended to describe conditions for hybridization and washing under which nucleotide sequences at least 66%, at least 70%, at least 75%, at least 80%, more preferably at least 85%, even more preferably at least 90%, preferably at least 95%, more preferably at least 98% or more preferably at least 99% homologous to each other typically remain hybridized to each other. That is to say, such hybridizing sequences may share at least 45%, at least 50%, at least 55%, at least 60%, at least 65, at least 70%, at least 75%, at least 80%, more preferably at least 85%, even more preferably at least 90%, more preferably at least 95%, more preferably at least 98% or more preferably at least 99% sequence identity.

A preferred, non-limiting example of such hybridization conditions is hybridization in 6× sodium chloride/sodium citrate (SSC) at about 45° C., followed by one or more washes in 1×SSC, 0.1% SDS at about 50° C., preferably at about 55° C., preferably at about 60° C. and even more preferably at about 65° C.

Highly stringent conditions include, for example, hybridization at about 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), Sambrook and Russell (2001) "Molecular Cloning: A Laboratory Manual (3rd edition), Cold Spring Harbor Laboratory, Cold Spring Harbor Laboratory Press, New York 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A)

stretch or the complement thereof (e.g., practically any double-stranded cDNA clone).

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or "expression construct" refer to nucleotide sequences that are capable of effecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most cells, preferably bacterial cells, under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The term "peptide" as used herein is defined as a chain of amino acid residues, usually having a defined sequence. As used herein the term peptide is interchangeable with the terms "polypeptide" and "protein". In the context of the present invention, the term "peptide" is defined as being any peptide or protein comprising at least two amino acids linked by a modified or unmodified peptide bond. The term "peptide" refers to short-chain molecules such as oligopeptides or oligomers or to long-chain molecules such as proteins. A protein/peptide can be linear, branched or cyclic.

The peptide can include D amino acids, L amino acids, or a combination thereof. A peptide according to the present invention can comprise modified amino acids. Thus, the peptide of the present invention can also be modified by natural processes such as post-transcriptional modifications or by a chemical process. Some examples of these modifications are: acetylation, acylation, ADP-ribosylation, amidation, covalent bonding with flavine, covalent bonding with a heme, covalent bonding with a nucleotide or a nucleotide derivative, covalent bonding to a modified or unmodified carbohydrate moiety, bonding with a lipid or a lipid derivative, covalent bonding with a phosphotidylinositol, cross-linking, cyclization, disulfide bond formation, demethylation, cysteine molecule formation, pyroglutamate formation, formylation, gamma-carboxylation, hydroxylation, iodination, methylation, oxidation, phosphorylation, racemization, etc. Thus, any modification of the peptide which does not have the effect of eliminating the immunogenicity of the peptide, is covered within the scope of the present invention.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'-nontranslated sequence (3'-end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide. The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell.

The terms "heterologous" and "exogenous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous and exogenous nucleic acids or proteins are not endogenous to the cell into which it is introduced, but have been obtained from another cell or synthetically or recombinantly produced. Generally, though not necessarily, such nucleic acids encode proteins, i.e. exogenous proteins, that are not normally produced by the cell in which the DNA is transcribed or expressed. Similarly exogenous RNA encodes for proteins not normally expressed in the cell in which the exogenous RNA is present. Heterologous/exogenous nucleic acids and proteins may also be referred to as foreign nucleic acids or proteins. Any nucleic acid or protein that one of skill in the art would recognize as foreign to the cell in which it is expressed is herein encompassed by the term heterologous or exogenous nucleic acid or protein. The terms heterologous and exogenous also apply to non-natural combinations of nucleic acid or amino acid sequences, i.e. combinations where at least two of the combined sequences are foreign with respect to each other.

The term "immune response" as used herein refers to the production of antibodies and/or cells (such as T lymphocytes) that are directed against, and/or assist in the decomposition and/or inhibition of, a particular antigenic entity, carrying and/or expressing or presenting antigens and/or antigenic epitopes at its surface. The phrases "an effective immunoprotective response", "immunoprotection", and like terms, for purposes of the present invention, mean an immune response that is directed against one or more antigenic epitopes of a pathogen, a pathogen-infected cell or a cancer cell so as to protect against infection by the pathogen or against cancer in a vaccinated subject. For purposes of the present invention, protection against infection by a pathogen or protection against cancer includes not only the absolute prevention of infection or cancer, but also any detectable reduction in the degree or rate of infection by a pathogen or of the cancer, or any detectable reduction in the severity of the disease or any symptom or condition resulting from infection by the pathogen or cancer in the vaccinated subject, for example as compared to an unvaccinated infected subject. An effective immunoprotective response in the case of cancer also includes clearing up the cancer cells, thereby reducing the size of cancer or even abolishing the cancer. Vaccination in order to achieve this is also called therapeutic vaccination. Alternatively, an effective immunoprotective response can be induced in subjects that have not previously been infected with the pathogen and/or are not infected with the pathogen or do not yet suffer from cancer at the time of vaccination, such vaccination can be referred to as prophylactic vaccination.

According to the present invention, the general use herein of the term "antigen" refers to any molecule that binds specifically to an antibody. The term also refers to any molecule or molecular fragment that can be bound by an MHC molecule and presented to a T-cell receptor. Antigens can be e.g. proteinaceous molecules, i.e. polyaminoacid sequences, optionally comprising non-protein groups such as carbohydrate moieties and/or lipid moieties or antigens can be e.g. molecules that are not proteinaceous such as carbohydrates. An antigen can be e.g. any portion of a protein (peptide, partial protein, full-length protein), wherein the protein is naturally occurring or synthetically derived, a cellular composition (whole cell, cell lysate or disrupted cells), an organism (whole organism, lysate or disrupted cells) or a carbohydrate or other molecule, or a portion thereof, that is able to elicit an antigen-specific immune response (humoral and/or cellular immune response) in a particular subject, which immune response preferably is measurable via an assay or method.

The term "antigen" is herein understood as a structural substance which serves as a target for the receptors of an adaptive immune response. An antigen thus serves as target for a TCR (T-cell receptor) or a BCR (B-cell receptor) or the secreted form of a BCR, i.e. an antibody. The antigen can thus be a protein, peptide, carbohydrate or other hapten that is usually part of a larger structure, such as e.g. a cell or a virion. The antigen may originate from within the body ("self") or from the external environment ("non-self"). The immune system is usually non-reactive against "self" antigens under normal conditions due to negative selection of T cells in the thymus and is supposed to identify and attack only "non-self" invaders from the outside world or modified/harmful substances present in the body under e.g. disease conditions. Antigen structures that are the target of a cellular immune response are presented by antigen presenting cells (APC) in the form of processed antigenic peptides to the T cells of the adaptive immune system via a histocompatibility molecule. Depending on the antigen presented and the type of the histocompatibility molecule, several types of T cells can become activated. For T-Cell Receptor (TCR) recognition, the antigen is processed into small peptide fragments inside the cell and presented to a T-cell receptor by major histocompatibility complex (MHC).

The term "immunogen" is used herein to describe an entity that comprises or encodes at least one epitope of an antigen such that when administered to a subject, preferably together with an appropriate adjuvant, elicits a specific humoral and/or cellular immune response in the subject against the epitope and antigen comprising the epitope. An immunogen can be identical to the antigen or at least comprises a part of the antigen, e.g. a part comprising an epitope of the antigen. Therefore, to vaccinate a subject against a particular antigen means, in one embodiment, that an immune response is elicited against the antigen or immunogenic portion thereof, as a result of administration of an immunogen comprising at least one epitope of the antigen. Vaccination preferably results in a protective or therapeutic effect, wherein subsequent exposure to the antigen (or a source of the antigen) elicits an immune response against the antigen (or source) that reduces or prevents a disease or condition in the subject. The concept of vaccination is well-known in the art. The immune response that is elicited by administration of a prophylactic or therapeutic composition of the present invention can be any detectable change in any facet of the immune status (e.g., cellular response, humoral response, cytokine production), as compared to in the absence of the administration of the vaccine.

An "epitope" is defined herein as a single immunogenic site within a given antigen that is sufficient to elicit an immune response in a subject. Those of skill in the art will recognize that T cell epitopes are different in size and composition from B cell epitopes, and that T cell epitopes presented through the Class I MHC pathway differ from epitopes presented through the Class II MHC pathway. Epitopes can be linear sequences or conformational epitopes (conserved binding regions) depending on the type of immune response. An antigen can be as small as a single epitope, or larger, and can include multiple epitopes. As such, the size of an antigen can be as small as about 5-12 amino acids (e.g., a peptide) and as large as: a full length protein, including multimeric proteins, protein complexes, virions, particles, whole cells, whole microorganisms, or portions thereof (e.g., lysates of whole cells or extracts of microorganisms).

An adjuvant is herein understood to be an entity, that, when administered in combination with an antigen to a human or an animal subject to raise an immune response against the antigen in the subject, stimulates the immune system, thereby provoking, enhancing or facilitating the immune response against the antigen, preferably without necessarily generating a specific immune response to the adjuvant itself. A preferred adjuvant enhances the immune response against a given antigen by at least a factor of 1.5, 2, 2.5, 5, 10 or 20, as compared to the immune response generated against the antigen under the same conditions but in the absence of the adjuvant. Tests for determining the statistical average enhancement of the immune response against a given antigen as produced by an adjuvant in a group of animal or human subjects over a corresponding control group are available in the art. The adjuvant preferably is capable of enhancing the immune response against at least two different antigens.

OMV (also referred to as "blebs") are bi-layered membrane structures, usually spherical, with a diameter in the range of 20-250 nm (sometimes 10-500 nm), that are pinched off from the outer membrane of gram-negative bacteria. The OMV membrane contains phospholipids (PL) on the inside and lipopolysaccharides (LPS) and PL on the outside, mixed with membrane proteins in various positions, largely reflecting the structure of the bacterial outer membrane from which they pinched off. The lumen of the OMV may contain various compounds from the periplasm or cytoplasm, such as proteins, RNA/DNA, and peptidoglycan (PG), however, unlike bacterial cells, OMV lack the ability to self-replicate. In the context of the present invention three type of OMV can be distinguished depending on the method of their production. sOMV are spontaneous or natural OMV that are purified and concentrated from culture supernatant, by separating intact cells from the already formed OMVs. Detergent OMV, dOMV, are extracted from cells with detergent, such as deoxycholate, which also reduces the content of reactogenic LPS. After detergent extraction dOMV are separated from cells and cellular debris and further purified and concentrated. Finally, the term native nOMV is used herein for OMV that are generated from concentrated dead cells with non-detergent cell disruption techniques, or that are extracted from cells with other (non-disruptive) detergent-free methods (e.g. using chelating agents such EDTA), to be able to clearly distinguish them from the wild-type spontaneous OMVs and from the detergent-extracted dOMV.

Any reference to nucleotide or amino acid sequences accessible in public sequence databases herein refers to the version of the sequence entry as available on the filing date of this document.

The Acyl Chain Length of the Modified Lipid a Moiety of *Bordetella* LPS

The current invention relates to the surprising discovery that reducing the length of the acyl chains of *Bordetella* lipid A moiety reduces LPS endotoxicity. The invention further discloses the unexpected finding that increasing the length of the acyl chain at a 3 position of the lipid A moiety results in lethality of the *Bordetella* species. Hence, the invention discloses that a specific subset of acyl transferases may be used in *Bordetella* species to reduce the length of the acyl chains and as such reduce the endotoxicity of the *Bordetella* LPS.

In a first aspect, the invention therefore pertains to a *Bordetella* LPS having a lipid A moiety that is modified as compared to the lipid A moiety of a wild-type *Bordetella* LPS in that the length of at least one acyl chain is shorter. Without wishing to be bound by any theory, such modification of the acyl chain length could affect binding of the accessory molecules, e.g. CD14. Accessory molecules have significantly different binding affinities for LPS of different bacteria [23], which could potentially be influenced by the acyl chain length.

Wild-type *Bordetella* lipopolysaccharide (LPS) contains a lipid A moiety that is penta-acylated. The lipid A moiety of wild-type *Bordetella pertussis* LPS is shown in FIG. 1. As shown in FIG. 1, the lipid A moiety of *Bordetella pertussis* contains four primary acyl chains and one secondary acyl chain. The secondary acyl chain is linked to the primary acyl chain at the 2' (2 prime) position and the wild-type length of the secondary acyl chain is a C14. Furthermore in contrast to the secondary acyl chains, the primary acyl chains are always hydroxylated at their 3'-end (3-OH).

The primary acyl chains are respectively at the 2 and 3 positions and 2' (2 prime) and 3' (3 prime) positions of the lipid A moiety. The wild-type length of the acyl chains of the primary acyl chains is C14 at the 2, 2' and 3' position and the length of the wild-type acyl chain at the 3 position is C10.

In addition, it is understood that the terms "acyl chain at the 2, 3, 2' or 3' position" and "primary acyl chain at the 2, 3, 2' or 3' position" can be used interchangeable herein.

Furthermore, it is herein understood that when referring to the acyl chain at the "prime" position in the lipid A moiety, the position of the glucosamine on the non-reducing end is intended. For example, the acyl chain at the 3' position is the acyl chain that is attached to the 3 position of the glucosamine on the non-reducing end.

Also, it is herein understood that when referring to the acyl chain at a specific (i.e. not prime) position in the lipid A moiety, the position of the glucosamine on the reducing end is intended. For example, the acyl chain at the 3 position is the acyl chain that is attached to the 3 position of the glucosamine on the reducing end. Similarly, the phrases "an acyl chain greater than" and "an acyl chain longer than" can be used interchangeable herein.

The phrases "an acyl chain shorter than" and "an acyl chain smaller than" can herein be used interchangeable.

It is herein understood that a shorter acyl chain does not include the complete absence of an acyl chain. Hence, a shorter acyl chain denotes the presence of an acyl chain, albeit shorter than the length of the acyl chain at the same position of the wild-type lipid A moiety. Preferably, an acyl chain is not shorter than 3-hydroxypropionic acid, or than propionic acid ($C_3$).

When reference is made to wild-type lipid A moiety (or unmodified lipid A moiety) in the text, at minimum the lipid A moiety of the wild-type *Bordetella pertussis* LPS as exemplified in FIG. 1 is intended, unless otherwise indicated. Similarly, the wild-type lipid A moiety of other *Bordetella* species are part of the disclosed invention. *Bordetella* lipid A moieties are e.g. disclosed in FIG. 2 of Caroff et al (Microbes and Infection 4 (2002):915-926, incorporated herein by reference). The wild-type lipid A moiety may be penta- or hexa-acylated. In case the lipid A moiety of the wild-type LPS is hexa-acylated, there are two secondary acyl chains (one at the 2' position and one at the 3' position). In case the *Bordetella* wild-type acyl chain of the lipid A moiety is hexa-acylated, any reference in the text made to the secondary acyl chain should be interpreted as the secondary acyl chain at the 2' position and/or at the 3' position.

In a preferred embodiment, the length of only one acyl chain is shorter than the acyl chain of the wild-type lipid A moiety at the same position. Preferably, the length of one primary acyl chain is shorter. More preferably, only the length of the primary acyl chain at the 2, 3, 2' or 3' position is shorter than the length of the wild-type *Bordetella* acyl chain at respectively the 2, 3, 2' or 3' position. Alternatively, only the length of the secondary acyl chain is shorter than the length of the wild-type *Bordetella* secondary acyl chain.

In an alternative embodiment, the length of at least one acyl chain is shorter. In particular, the length of at least the acyl chain at the 2 position is shorter than the wild-type length at the 2 position, thus shorter than C14. Alternatively, at least the acyl chain at the 3 position or at the 2' position is shorter than the wild-type length at respectively the 3 or 2' position, thus shorter than respectively C10 or C14. In another embodiment, at least the length of the acyl chain at the 3' position is shorter than the wild-type length of the acyl chain at the 3' position, thus shorter than C14. Alternatively, the length of at least the acyl chain at the secondary acyl chain is shorter than the length of the wild-type secondary acyl chain, thus shorter than C14.

In a preferred embodiment, the invention thus pertains to a *Bordetella* LPS having a lipid A moiety that is modified as compared to the lipid A moiety of a wild-type *Bordetella* LPS in that the length of at least one acyl chain is shorter, wherein the shorter acyl chain is selected from the group consisting of:

i) the acyl chain at the 3' position of the lipid A moiety;

ii) the primary acyl chain at the 2' position of the lipid A moiety;

iii) the secondary acyl chain at the 2' position of the lipid A moiety; and iv) the acyl chain at the 2 position of the Lipid A moiety.

In a further preferred embodiment, the length of at least 2, 3, 4 or (all) 5 acyl chains in the lipid A moiety is shorter than the wild-type length at the same position. Preferably the length of (at least) the acyl chain at the 2 and 2' position is shorter than the length of the acyl chain of the wild-type acyl chains at respectively the 2 and 2' position.

In a preferred embodiment, the invention thus pertains to a *Bordetella* LPS having a lipid A moiety that is modified as compared to the lipid A moiety of a wild-type *Bordetella* LPS in that the length of at least one acyl chain is shorter, wherein the acyl chain is at least two, four or six C atoms shorter. The at least one shorter acyl chain can be any of the acyl chains as specified above. The at least one shorter acyl chain is preferably at least 12, 10, 8, 6, 4 or 2 C atoms shorter in comparison to the length of the acyl chain at the same position of the lipid A moiety of the wild-type *Bordetella. Alternatively, the shorter acyl chain is preferably at most* 2, 4, 6, 8, 10 or 12 C atoms shorter. More preferably, the acyl chain is at least 8, 6, 4 or 2 C atoms shorter, more preferably at least 4 or 2 C atoms shorter and even more preferably at least 2 C atoms shorter. In the most preferred embodiment, the modified acyl chain is 2 C atoms shorter as comparted to the length of the acyl chain at the same position of the lipid A moiety of the wild-type *Bordetella.*

In a preferred embodiment, the length of the acyl chain at the 2 position is preferably at least 12, 10, 8, 6, 4, or 2 C atoms shorter in comparison to the length of the acyl chain at the 2 position of the lipid A moiety of the wild-type *Bordetella*. Alternatively, the shorter acyl chain is preferably at most 2, 4, 6, 8, 10 or 12 C atoms shorter. Hence, the length of the acyl chain at the 2 position of the modified lipid A moiety is preferably $C_2$, $C_4$, $C_6$, $C_8$, $C_{10}$ or $C_{12}$.

Alternatively or in addition, the length of the acyl chain at the 3 position is preferably at least 14, 12, 10, 8, 6, 4, or 2 C atoms shorter in comparison to the length of the acyl chain at the 3 position of the lipid A moiety of the wild-type *Bordetella*. Alternatively, the shorter acyl chain is preferably at most 2, 4, 6, 8, 10, 12 or 14 C atoms shorter. Hence, the length of the acyl chain at the 3 position of the modified lipid A moiety is preferably $C_2$, $C_4$, $C_6$, $C_8$, $C_{10}$, $C_{12}$ or $C_{14}$, and more preferably $C_2$, $C_4$, $C_6$ or $C_8$.

Alternatively or in addition, the length of the acyl chain at the 2' position is preferably at least 12, 10, 8, 6, 4, or 2 C atoms shorter in comparison to the length of the acyl chain at the 2' position of the lipid A moiety of the wild-type *Bordetella*. Alternatively, the shorter acyl chain is preferably at most 2, 4, 6, 8, 10 or 12 C atoms shorter. Hence, the length of the acyl chain at the 2' position of the modified lipid A moiety is preferably $C_2$, $C_4$, $C_6$, $C_8$, $C_{10}$ or $C_{12}$.

Alternatively or in addition, the length of the acyl chain at the 3' position is preferably at least 12, 10, 8, 6, 4, or 2 C atoms shorter in comparison to the length of the acyl chain at the 3' position of the lipid A moiety of the wild-type *Bordetella*. Alternatively, the shorter acyl chain is preferably at most 2, 4, 6, 8, 10 or 12 C atoms shorter. Hence, the length of the acyl chain at the 3' position of the modified lipid A moiety is preferably $C_2$, $C_4$, $C_6$, $C_8$, $C_{10}$ or $C_{12}$.

Finally, alternatively or in addition, the length of the acyl chain of the secondary acyl chain is preferably at least 12, 10, 8, 6, 4, or 2 C atoms shorter in comparison to the length of the secondary acyl chain of the lipid A moiety of the wild-type *Bordetella*. Alternatively, the shorter acyl chain is preferably at most 2, 4, 6, 8, 10 or 12 C atoms shorter. Hence, the length of the secondary acyl chain of the modified lipid A moiety is preferably $C_2$, $C_4$, $C_6$, $C_8$, $C_{10}$ or $C_{12}$.

In addition, the length of 1, 2, 3 or 4 acyl chains of the modified lipid A moiety that are not shorter than the length of the wild-type acyl chain, may have a greater length than the acyl chain at the same position of the wild-type lipid A moiety. Thus in a further embodiment, the length of at least one acyl chain of the modified lipid A moiety is greater than the length of the wild-type acyl chain at the same position in the lipid A moiety, preferably in addition to another acyl chain in the same modified lipid A moiety that is shorter in length as specified above. Preferably, the length of the primary acyl chain at least at the 2, 3, 2' and/or 3' position, more preferably at the 2, 2' and/or 3' position, is greater than the length of the wild-type acyl chain at the same position in the lipid A moiety. Alternatively, or in addition, the length of the secondary acyl chain is greater than the length of the secondary acyl chain of the wild-type *Bordetella* lipid A moiety.

However in a preferred embodiment, the invention relates to a *Bordetella* LPS having a lipid A moiety that is modified as compared to the lipid A moiety of a wild-type *Bordetella* LPS in that the length of at least one acyl chain is shorter, and wherein the length of the acyl chain at the 3 position of the modified lipid A moiety does not have a greater length than the acyl chain of the wild-type *Bordetella* lipid A moiety at the same 3 position.

Hence, the acyl chain at the 3 position is preferably $C_{16}$ or less (in case the lipid A moiety of the wild-type *Bordetella* is e.g. *B. parapertussis*), $C_{12}$ or less (in case the lipid A moiety of the wild-type *Bordetella* is e.g. *B. bronchiseptica* or *B. hinzii*) or $C_{10}$ or less (in case the lipid A moiety of the wild-type *Bordetella* is e.g. *B. pertussis*), as specified above. In particular, the invention as exemplified below teaches that increasing the length of the acyl chain at the 3 position beyond the length of the wild-type acyl chain at the same 3 position may result in lethality of the *Bordetella* species. Hence, in a most preferred embodiment the length of the acyl chain at the 3 position of the modified lipid A moiety does not exceed $C_{10}$.

Similarly, in a preferred embodiment the length of the primary acyl chain at the 2, 2' or 3' position of the modified lipid A moiety does not exceed $C_{14}$ and/or the length of the secondary acyl chain does not exceed $C_{14}$.

Alternatively or in addition, the length of the acyl chain at the 3 position of the modified lipid A moiety is the same as the length of the acyl chain at the 3' position. Hence both the acyl chain at the 3 position as well as the acyl chain at the 3' position is $C_2$, $C_4$, $C_6$, $C_{10}$, $C_{12}$, $C_{14}$ or $C_{16}$. Preferably, both acyl chains are $C_{10}$ or $C_{12}$, and most preferably both acyl chains are $C_{10}$.

As outlined above, the length of one or several acyl chains in the modified lipid A moiety is shorter than the length of the wild-type acyl chain at the same position in the lipid A moiety. The acyl chains that are not shorter as compared to the wild-type length, may have the same length as the length of the wild-type acyl chains or may be longer. Preferably the acyl chains that are not shorter as compared to the wild-type length remain of the same length as the acyl chain of the wild-type *Bordetella* lipid A moiety, e.g. remain unaltered.

In a particularly preferred embodiment, the invention pertains to a *Bordetella* LPS having a lipid A moiety that is modified as compared to the lipid A moiety of a wild-type *Bordetella* LPS in that the length of at least one acyl chain is shorter, wherein the length of the acyl chain at the 3 position of the modified lipid A moiety has the same length as the acyl chain of the wild-type *Bordetella* lipid A moiety at the same 3 position. Hence, the length of the acyl chain at the 3 position of the modified *Bordetella* lipid A moiety is preferably $C_{10}$. In addition or alternatively, the acyl chain of at least one of the 2, 2' and 3' position in the modified lipid A moiety may have the same length as the acyl chain at respectively the 2, 2' or 3' position of the wild-type *Bordetella* lipid A moiety. Hence, in a preferred embodiment the length of the acyl chain of at least one of the 2, 2' or 3' position of the modified lipid A moiety is $C_{14}$. Similarly, the length of the secondary acyl chain at the 2' position is the same length as the wild-type secondary acyl chain, i.e. is $C_{14}$.

Thus, the modified *Bordetella* lipid A moiety of the invention may have one or more acyl chains that are shorter than the acyl chain(s) at the same position(s) in the wild-type *Bordetella* lipid A moiety and/or one or more acyl chains that are longer than the acyl chain(s) at the same position(s) in the wild-type *Bordetella* lipid A moiety and/or one or more acyl chains that have the same length as the acyl chain(s) at the same position(s) in the wild-type *Bordetella* lipid A moiety. Most preferably, the modified lipid A moiety has at least one acyl chain that is shorter than the length of the acyl chain at the same position of the wild-type *Bordetella* lipid A moiety.

In another embodiment, the total number of C-atoms in the acyl chains of the modified lipid A moiety is the same as the total number of C-atoms in the acyl chains of the wild-type *Bordetella* lipid A moiety as described above. The total number of C-atoms in the acyl chains of the Lipid A moiety of wild-type *Bordetella* is: $C_{14}$ (2 position)+$C_{10}$ (3 position)+$C_{14}$ (2' position)+$C_{14}$ (secondary acyl chain)+$C_{14}$ (3' position) in total 66 C atoms. In a preferred embodiment, the total number of C atoms in the acyl chains of the modified lipid A moiety is therefore 66 C atoms.

Alternatively, the total number of C atoms in the acyl chains of the modified lipid A moiety is higher than the total number of C atoms in the acyl chains of the wild-type *Bordetella* lipid A moiety, thus is higher than 66 C atoms, preferably higher than 68, 70, 72 or 74 C atoms.

However, preferably the total number of C atoms in the acyl chains of the modified lipid A moiety is lower than the total number of C atoms in the acyl chains of the wild-type *Bordetella* lipid A moiety, thus is lower than 66 C atoms, preferably in total 64, 62, 60, 58, 56, 54, 52, 50, 48, 46, 44, 42 or 40 C atoms.

In particular, the invention as exemplified below shows that the effect on toxicity is obtained independent of the position of the shorter acyl chain. Hence, the total volume of the hydrophobic moiety of the lipid A molecule is apparently important for the proper binding to and activation of the hTLR4 complex. Presumably, the shorter acyl chains affect the interaction of LPS with its receptor. On the membrane, TLR4 forms a complex with MD-2 [21]. MD-2 binds LPS and accommodates five of the six acyl chains of a hexa-acylated lipid A in a hydrophobic pocket, while one chain lies outside and stimulates TLR4 dimerization through its binding of a second TLR4-MD-2 complex. Also the phosphate groups of lipid A contribute to receptor dimerization by interacting with positively charged residues on the second TLR4 molecule. In tetra-acylated lipid A species, the acyl chains are buried in the MD-2 ligand-binding pocket and can't stimulate receptor dimerization, while exposition of an acyl chain is variable in penta-acylated LPS [22]. Hence the total acyl-chain volume of the ligand, as determined by the number, length and position of acyl chains, may determine the exposition of an acyl chain that triggers TLR4 dimerization. Without wishing to be bound by any theory, decreasing the length of the acyl chains in *Bordetella* lipid A reduces the volume of the acyl chains, which may allow their total accommodation within the MD-2 binding pocket and thereby preventing the exposure of an acyl chain required for receptor dimerization.

In a further preferred embodiment, the *Bordetella* LPS of the invention has a modified lipid A moiety as defined above. Except for the modified lipid A moiety, the *Bordetella* LPS of the invention otherwise has the structure of a lipopolysaccharide that is obtained or obtainable from a bacterium of the genus *Bordetella*. The genus *Bordetella* comprises nine species of gram-negative bacteria. The most extensively studied of these are the respiratory pathogens *Bordetella pertussis, Bordetella parapertussis*, and *Bordetella bronchiseptica. B. pertussis* infects only humans and is the causative agent of whooping cough in infants and persistent respiratory infections in adults. *B. parapertussis* exists as two separate lineages. One is adapted to the human host and causes whooping cough; the other is adapted to the ovine host in which it can cause chronic pneumonia. In contrast, *B. bronchiseptica* colonizes the respiratory tract of a large number of animals, and although it causes respiratory infections in some farm, companion, and wild animals, most *B. bronchiseptica* infections are asymptomatic and chronic. *B. bronchiseptica* is occasionally isolated from the respiratory tract of humans and is likely acquired through contact with infected animals (Preston et al, J. of Biol. Chem, 2006, 281(26):18135-18144).

The lipid A moiety of e.g. *B. pertussis, B. parapertussis, B. hinzii* and *B. bronchiseptica* is disclosed in FIG. 2 of Caroff et al (Microbes and Infection 4 (2002):915-926, incorporated herein by reference). In contrast to the LPS of *B. bronchiseptica* and *B. parapertussis*, the LPS of *B. pertussis* never contains an O-antigen domain (Peppler, 1984; Di Fabio et al., 1992). Therefore, *B. pertussis* LPS is often referred to as lipooligosaccharide (LOS). In the context of the invention, the terms "LOS" and "LPS" are used interchangeable herein. For reasons of consistency, we shall further refer to LPS. *B. pertussis* produces two dominant LPS forms, band A and band B LPS (Peppler, 1984). Band B LPS is composed of lipid A and a core oligosaccharide consisting of 9 carbohydrates (Caroff et al., 2000). Addition of a terminal trisaccharide, consisting of N-acetyl glucosamine, 2,3-diacetamido-2,3-dideoxy-mannuronic acid, and 2-acetamido-4-N-methyl-2,4-dideoxy-fucose, to band B LPS forms the LPS referred to as band A.

Preferably therefore, the invention relates to a *Bordetella* LPS having a lipid A moiety that is modified as compared to the lipid A moiety of a wild-type *Bordetella* LPS in that the length of at least one acyl chain is shorter and wherein, except for the modified lipid A moiety as defined herein, the LPS has the structure of *Bordetella pertussis, Bordetella parapertussis* or *Bordetella bronchiseptica*, or a strain of these species having a genetic modification, e.g. as described herein below. Preferably the *Bordetella* LPS has, except for the modified lipid A moiety, the structure of *Bordetella pertussis* or *Bordetella parapertussis*, of which *Bordetella pertussis* is the most preferred.

In a further preferred embodiment in invention concerns a *Bordetella* LPS having a lipid A moiety that is modified as compared to the lipid A moiety of a wild-type *Bordetella* LPS in that the length of at least one acyl chain is shorter, and wherein the modified lipid A moiety has the structure of formula (I):

General formula (I)

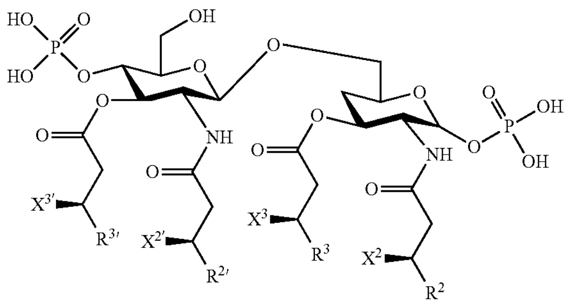

wherein $X^2$, $X^3$, $X^{2'}$, $X^{3'}$, $R^2$, $R^3$, $R^{2'}$, and $R^{3'}$ are each independently selected from the group consisting of —H, —OH, —Y, —O—(C═O)—CH(OH)—Y, and —O—(C═O)—Y, wherein Y is an alkyl moiety of general formula $—(CH_2)_n—H$, and n is an integer that for each instance of Y is independently chosen from 1, 2, 3, 4, 5, 6, 7, 8, 9, 10, 11, 12, 13, 14, or 15.

Preferably, $X^2$, $X^3$, $X^{2'}$, $X^{3'}$, $R^2$, $R^3$, $R^{2'}$, and $R^{3'}$ are each independently selected from the group consisting of —H, —OH, —Y, and —O—(C═O)—Y, wherein Y is an alkyl moiety of general formula $—(CH_2)_n—H$, and n is an integer that for each instance of Y is independently chosen from 1, 2, 3, 4, 5, 6, 7, 8, 9, 10, 11, 12, 13, 14, or 15.

In preferred compounds of general formula (I), $X_2$, $X_3$, $X_2'$, and $X_3'$ are each independently selected from the group consisting of —H, —OH, —O—(C═O)—CH(OH)—Y, and —O—(C═O)—Y wherein Y is an alkyl moiety of general formula $—(CH_2)_n—H$, and n is an integer that for each instance of Y is independently chosen from 1, 2, 3, 4, 5, 6, 7, 8, 9, 10, 11, 12, 13, 14 or 15, and more preferably independently chosen from 1, 3, 5, 7, 9, 11, 13 or 15.

In preferred compounds of general formula (I), $R_2$, $R_3$, $R_2'$, and $R_3'$ are each —Y, wherein Y is an alkyl moiety of general formula $—(CH_2)_n—H$, and n is an integer that for each instance of Y is independently chosen from 1, 2, 3, 4, 5, 6, 7, 8, 9, 10, 11, 12, 13, 14, or 15, and more preferably independently chosen from 1, 3, 5, 7, 9, 11, 13 or 15.

As is clear to a skilled reader, Y can be different for each of $X^2$, $X^3$, $X^{2'}$, $X^{3'}$, $R^2$, $R^3$, $R^{2'}$, and $R^{3'}$, and thus multiple different instances of Y can occur within a single compound of general formula (I). Accordingly, in preferred compounds of general formula (I), $X^2$ is selected from the group consisting of —H, —OH, —$Y^{X2}$, —O—$Y^{X2}$, —O—(C═O)—CH(OH)—$Y^{X2}$, and —O—(C═O)—$Y^{X2}$, wherein $Y^{X2}$ is an alkyl moiety of general formula $—(CH_2)_n—H$, and n is an integer chosen from 1, 2, 3, 4, 5, 6, 7, 8, 9, 10, 11, 12, 13, 14, or 15; preferably, $X^2$ is —OH or —O—(C═O)—$Y^{X2}$, most preferably $X^2$ is —OH;

$X^3$ is selected from the group consisting of —H, —OH, —$Y^{X3}$, —O—$Y^{X3}$, —O—(C═O)—CH(OH)—$Y^{X3}$, and —O—(C═O)—$Y^{X3}$, wherein $Y^{X3}$ is an alkyl moiety of general formula $—(CH_2)_n—H$, and n is an integer chosen from 1, 2, 3, 4, 5, 6, 7, 8, 9, 10, 11, 12, 13, 14, or 15; preferably, $X^3$ is —OH or —H, most preferably $X^3$ is —OH;

$X^{2'}$ is selected from the group consisting of —H, —OH, —$Y^{X2'}$, —O—$Y^{X2'}$, —O—(C═O)—CH(OH)—$Y^{X2}$, and —O—(C═O)—$Y^{X2'}$, wherein $Y^{X2'}$ is an alkyl moiety of general formula $—(CH_2)_n—H$, and n is an integer chosen from 1, 2, 3, 4, 5, 6, 7, 8, 9, 10, 11, 12, 13, 14, or 15; preferably, $X^{2'}$ is —OH, —O—(C═O)—CH(OH)—$Y^{X2'}$, or —O—(C═O)—$Y^{X2'}$, wherein when $X^{2'}$ is —O—(C═O)—$Y^{X2'}$, n is preferably an integer chosen from 1, 3, 5, 7, 9, 11, or 13, more preferably n is 11 or 13 and most preferably n is 13, and wherein when $X^{2'}$ is —O—(C═O)—CH(OH)—$Y^{X2'}$ n is preferably an integer chosen from 2, 4, 6, 8, 10, or 12, more preferably n is 10 or 12, and most preferably n is 12; most preferably, $X^{2'}$ is —O—(C═O)—$Y^{X2'}$ wherein n is 13;

$X^{3'}$ is selected from the group consisting of —H, —OH, —$Y^{X3'}$, O—$Y^{X3'}$, —O—(C═O)—CH(OH)—$Y^{X3}$, and —O—(C═O)—$Y^{X3'}$, wherein $Y^{X3'}$ is an alkyl moiety of general formula $—(CH_2)_n—H$, and n is an integer chosen from 1, 2, 3, 4, 5, 6, 7, 8, 9, 10, 11, 12, 13, 14, or 15; preferably, $X^{3'}$ is —OH or —O—(C═O)—$Y^{X3'}$, wherein when $X^{3'}$ is —O—(C═O)—$Y^{X3'}$ n is preferably an integer chosen from 1, 3, 5, 7, 9, 11, 13 or 15, more preferably n is 13 or 15 and most preferably n is 15; most preferably, $X^{3'}$ is —OH;

$R^2$ is selected from the group consisting of —H, —OH, —$Y^{R2}$, —O—$Y^{R2}$, —O—(C═O)—CH(OH)—$Y^{R2}$, and —O—(C═O)—$Y^{R2}$, wherein $Y^{R2}$ is an alkyl moiety of general formula $—(CH_2)_n—H$, and n is an integer chosen from 1, 2, 3, 4, 5, 6, 7, 8, 9, 10, 11, 12, 13, 14, or 15; preferably, $R^2$ is $Y^{R2}$; wherein n is preferably an integer chosen from 1, 3, 5, 7, 9, or 11, more preferably n is 9 or 11, and most preferably n is 11; most preferably, $R^2$ is $Y^{R2}$ wherein n is 11;

$R^3$ is selected from the group consisting of —H, —OH, —$Y^{R3}$, —O—$Y^{R3}$, —O—(C═O)—CH(OH)—$Y^{R3}$, and —O—(C═O)—$Y^{R3}$, wherein $Y^{R3}$ is an alkyl moiety of general formula $—(CH_2)_n—H$, and n is an integer chosen from 1, 2, 3, 4, 5, 6, 7, 8, 9, 10, 11, 12, 13, 14, or 15; preferably, $R^3$ is $Y^{R3}$ wherein n is preferably an integer chosen from 1, 3, 5, 7, 9, 11, or 13, more preferably n is an integer chosen from 7, 9, or 13, most preferably n is 7; most preferably, $R^3$ is $Y^{R3}$ wherein n is 7;

$R^{2'}$ is selected from the group consisting of —H, —OH, —$Y^{R2}$, —O—$Y^{R2'}$, —O—(C═O)—CH(OH)—$Y^{R2}$, and —O—(C═O)—$Y^{R2'}$, wherein $Y^{R2'}$ is an alkyl moiety of general formula $—(CH_2)_n—H$, and n is an integer chosen from 1, 2, 3, 4, 5, 6, 7, 8, 9, 10, 11, 12, 13, 14, or 15; preferably, $R^{2'}$ is $Y^{R2'}$ wherein n is preferably an integer chosen from 1, 3, 5, 7, 9, or 11 and more preferably n is 9 or 11 and most preferably n is 11; most preferably, $R^{2'}$ is $Y^{R2'}$ wherein n is 11;

$R^{3'}$ is selected from the group consisting of —H, —OH, —$Y^{R3'}$, —O—$Y^{R3'}$, —O—(C═O)—CH(OH)—$Y^{R3}$, and —O—(C═O)—$Y^{R3'}$, wherein $Y^{R3'}$ is an alkyl moiety of general formula $—(CH_2)_n—H$, and n is an integer chosen from 1, 2, 3, 4, 5, 6, 7, 8, 9, 10, 11, 12, 13, 14, or 15; preferably, $R^{3'}$ is $Y^{R3'}$ wherein n is preferably an integer chosen from 1, 3, 5, 7, 9, or 11, more preferably n is 7 or 11, most preferably n is 11; most preferably, $R^{3'}$ is $Y^{R3'}$ wherein n is 11;

When a compound of general formula (I) comprises $—Y^{X2}$, $—Y^{X3}$, $—Y^{X2'}$, or $—Y^{X3'}$, n is preferably an odd number, more preferably 5, 7, 9, 11, 13, or 15, most preferably 11 or 13. When a compound of general formula (I) comprises $—Y^{R2}$, $—Y^{R3}$, $—Y^{R2'}$, or $—Y^{R3'}$, n is preferably an odd number, more preferably 3, 5, 7, 9, 11, or 13, most preferably 7 or 11.

In preferred compounds of general formula (I), $R^2$ is $Y^{R2}$ where n is 9 or 11. Accordingly, in preferred compounds of general formula (I), $R^2$ is $—(CH_2)_9—H$ or $R^2$ is $—(CH_2)_{11}—H$. In further preferred compounds of general formula (I), $X^2$ is —OH. In more preferred compounds of general formula (I), $R^2$ is $—(CH_2)_9—H$ or $—(CH_2)_{11}—H$ and $X^2$ is —OH. In most preferred compounds of general formula (I), $R^2$ is $—(CH_2)_{11}—H$ and $X^2$ is —OH.

In preferred compounds of general formula (I), $R^{2'}$ is $Y^{R2'}$ where n is 9 or 11. Accordingly, in preferred compounds of general formula (I), $R^{2'}$ is $—(CH_2)_9—H$ or $R^{2'}$ is $—(CH_2)_{11}—H$. In further preferred compounds of general formula (I), $X^{2'}$ is $—O—(C{=}O)—Y^{X2'}$. In more preferred compounds of general formula (I), $R^{2'}$ is $—(CH_2)_9—H$ or $R^{2'}$ is $—(CH_2)_{11}—H$ and $X^{2'}$ is $—O—(C{=}O)—Y^{X2'}$. In most preferred compounds of general formula (I), $R^{2'}$ is $—(CH_2)_{11}—H$ and $X^{2'}$ is $—O—(C{=}O)—Y^{X2}$.

In more preferred compounds of general formula (I), $R^2$ is $Y^{R2}$ where n is 9 or 11 and $R^{2'}$ is $Y^{R2'}$ where n is 9 or 11. Accordingly, in preferred compounds of general formula (I), $R^2$ and $R^{2'}$ are $—(CH_2)_9—H$ or $—(CH_2)_{11}—H$. In further more preferred compounds of general formula (I), $X^2$ is —OH and $X^{2'}$ is $—O—(C{=}O)—Y^{X2'}$. In even more preferred compounds of general formula (I), $R^2$ and $R^{2'}$ are $—(CH_2)_9—H$ or $—(CH_2)_{11}—H$, $X^2$ is —OH, and $X^{2'}$ is $—O—(C{=}O)—Y^{X2'}$. More preferably, $R^2$ and $R^{2'}$ are both $—(CH_2)_9—H$ or are both $—(CH_2)_{11}—H$, and even more preferably $R^2$ and $R^{2'}$ are $—(CH_2)_{11}—H$. In most preferred compounds of general formula (I), $R^2$ and $R^{2'}$ are $—(CH_2)_{11}—H$, $X^2$ is —OH, and $X^{2'}$ is $—O—(C{=}O)—Y^{X2'}$.

In preferred compounds of general formula (I), $R^3$ is $Y^{R3}$. In further preferred compounds of general formula (I), $R^{3'}$ is $Y^{R3'}$. In more preferred compounds of general formula (I), $R^3$ is $Y^{R3}$ and $R^{3'}$ is $Y^{R3'}$. In even more preferred compounds of general formula (I), $R^3$ is $Y^{R3}$, $R^{3'}$ is $Y^{R3'}$, and $X^3$ is —H or —OH.

In one set of most preferred compounds of general formula (I), $R^2$ and $R^{2'}$ are $—(CH_2)_9—H$, $X^2$ is —OH, $X^{2'}$ is $—O—(C{=}O)—Y^{X2'}$, $R^3$ is $Y^{R3}$, $R^{3'}$ is $Y^{R3'}$ and $X^3$ is —H or —OH. Such compounds are of general formula ($II_{12}$). General formula ($II_2$) is depicted below.

In another set of most preferred compounds of general formula (I), $R^2$ and $R^{2'}$ are $—(CH_2)_{11}—H$, $X^2$ is —OH, $X^{2'}$ is $—O—(C{=}O)—Y^{X2'}$, $R^3$ is $Y^{R3}$, $R^{3'}$ is $Y^{R3'}$ and $X^3$ is —H or —OH. Such compounds are of general formula ($II_{14}$). General formula ($II_{14}$) is depicted below. Compounds of general formula ($II_{12}$) or ($II_{14}$) can be referred to as compounds of general formula (II). In such a case, independent reference is made to both general formula ($II_{12}$) and general formula ($II_{14}$).

General formula ($II_{12}$)

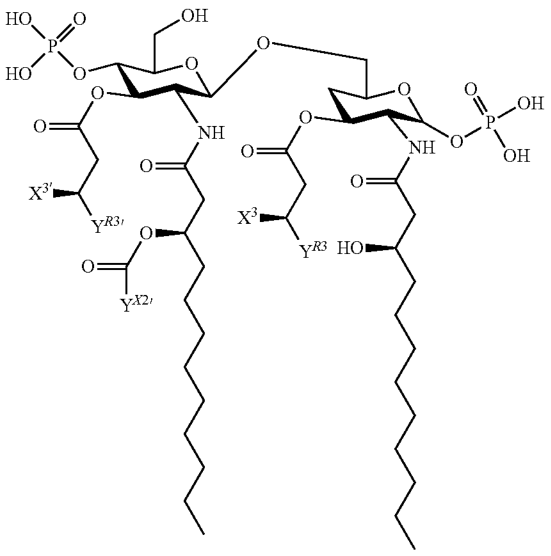

General formula ($II_{14}$)

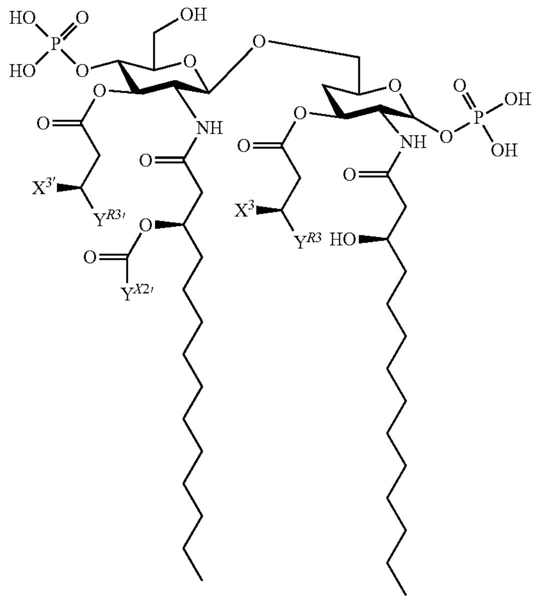

In preferred compounds of general formula (II), $X^3$ is —OH. In other preferred compounds of general formula (II), $X^{3'}$ is —OH. In more preferred compounds of general formula (II), $X^3$ and $X^{3'}$ are —OH.

In preferred compounds of general formula (II), $Y^{R3}$ is $—(CH_2)_7—H$. In more preferred compounds of general formula (II) $Y^{R3}$ is $—(CH_2)_7—H$, and $X^3$ and $X^{3'}$ are —OH. Such compounds are of general formula ($III_{12}$) or of general formula ($III_{14}$). General formulae ($III_{12}$) and ($III_{14}$) are depicted below. Compounds of general formula ($III_{12}$) or ($III_{14}$) can be referred to as compounds of general formula (III). In such a case, independent reference is made to both general formula ($III_{12}$) and general formula ($III_{14}$).

General formula ($III_{12}$)

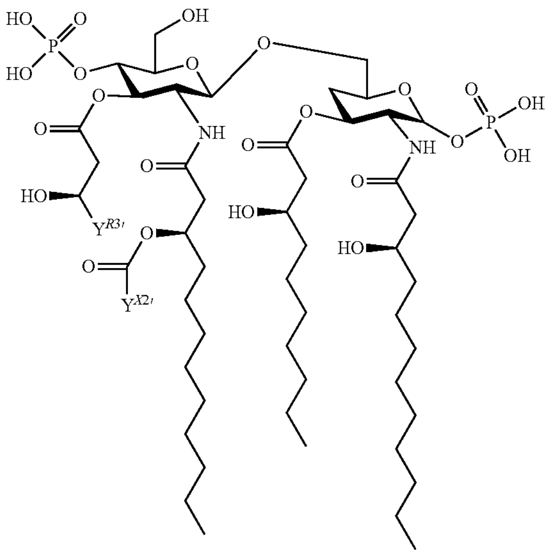

General formula ($III_{14}$)

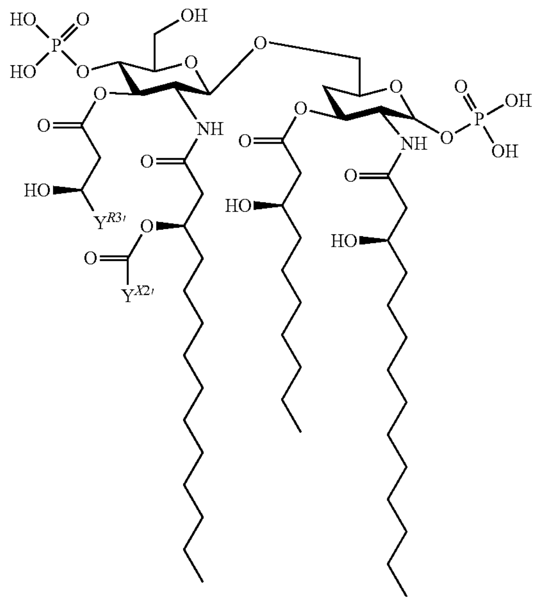

In preferred compounds of general formula (II), n is 1, 2, 3, 4, 5, 6, 7, 8, 9, 10, or 11 for $Y^{R3'}$; more preferably, n is 5, 7, or 9 for $Y^{R3'}$; even more preferably, n is 7 or 9 for $Y^{R3'}$; most preferably, n is 7 for $Y^{R3'}$. In preferred compounds of general formula (III), n is 1, 2, 3, 4, 5, 6, 7, 8, 9, 10, or 11 for $Y^{R3'}$; more preferably, n is 5, 7, or 9 for $Y^{R3'}$; even more preferably, n is 7 or 9 for $Y^{R3'}$; most preferably, n is 7 for $Y^{R3}$.

In preferred compounds of general formula (II), n is 3, 4, 5, 6, 7, 8, 9, 10, 11, 12, or 13 for $Y^{X2'}$; more preferably, n is 7, 9, 11, or 13 for $Y^{X2'}$; even more preferably, n is 9, 11, or 13 for $Y^{X2'}$; most preferably, n is 11 or 13 for $Y^{X2'}$. In preferred compounds of general formula (III), n is 3, 4, 5, 6, 7, 8, 9, 10, 11, 12, or 13 for $Y^{X2'}$; more preferably, n is 7, 9, 11, or 13 for $Y^{X2'}$; even more preferably, n is 9, 11, or 13 for $Y^{X2'}$; most preferably, n is 11 or 13 for $Y^{X2}$.

In more preferred compounds of general formula (II), n is 5, 7, 9, or 11 for $Y^{R3'}$ and n is 7, 9, 11, or 13 for $Y^{X2'}$; even more preferably, n is 7 or 9 for $Y^{R3'}$ and n is 9, 11, or 13 for $Y^{X2'}$; most preferably, n is 7 for $Y^{R3'}$ and n is 11 or 13 for $Y^{X2'}$. In a highly preferred compound of general formula (II), n is 7 for $Y^{R3'}$ and n is 11 for $Y^{X2'}$. In another highly preferred compound of general formula (II), n is 7 for $Y^{R3'}$ and n is 13 for $Y^{X2'}$. In more preferred compounds of general formula (III), n is 5, 7, 9, or 11 for $Y^{R3'}$ and n is 7, 9, 11, or 13 for $Y^{X2'}$; even more preferably, n is 7 or 9 for $Y^{R3}$, and n is 9, 11, or 13 for $Y^{X2'}$; most preferably, n is 7 for $Y^{R3'}$ and n is 11 or 13 for $Y^{X2}$.

In a highly preferred compound of general formula (III), the compound is of general formula ($III_{14}$) and n is 7 for $Y^{R3'}$ and n is 11 for $Y^{X2'}$. In another highly preferred compound of general formula (III), the compound is of general formula ($III_{14}$) and n is 7 for $Y^{R3'}$ and n is 13 for $Y^{X2'}$. In a highly preferred compound of general formula (III), the compound is of general formula ($III_{12}$) and n is 7 for $Y^{R3'}$ and n is 11 for $Y^{X2'}$. In another highly preferred compound of general formula (III), the compound is of general formula ($III_{12}$) and n is 7 for $Y^{R3'}$ and n is 13 for $Y^{X2'}$.

In a further embodiment, the LPS as defined above is obtained or obtainable from the genetically modified bacterium as defined herein below.

Genetically Modified Bacterium

In a second aspect, the invention pertains to a genetically modified bacterium of the genus *Bordetella*. The bacterium preferably comprises an LPS having a modified lipid A moiety as defined above. The genetically modified bacterium may comprise LPS wherein at least 10, 20, 30, 40, 50, 60, 70, 80 or 90% of its total LPS has a modified lipid A moiety as defined herein. Alternatively, 100% of its total LPS has a modified lipid A moiety as defined herein.

In a preferred embodiment, the bacterium is modified compared to the wild-type *Bordetella* bacterium in that it has a genetic modification that introduces a heterologous acyl transferase activity. Preferably, the genetic modification that introduces a heterologous acyl transferase activity confers to the cell at least one of a heterologous LpxA, LpxL, and LpxD acyl transferase activity.

The introduction of heterologous acyl transferase activity may be accomplished using any method known in the art. For example, the heterologous acyl transferase activity may be introduced by modifying an endogenous wild-type *Bordetella* acyl transferase gene, preferably by modifying at least one of an endogenous lpxA, lpxL, and lpxD acyl transferase gene.

In a preferred embodiment, the structure of the molecular ruler of the endogenous acyl transferase is modified. To this end, it is known in the art that acyl transferases have strict molecular (hydrocarbon) rulers which determine the specificity for the acyl chain length. Modifying the structure of such hydrocarbon ruler will thus change the specificity for the acyl chain length. The amino acid sequences of acyl transferase hydrocarbon rulers are known in the art (see e.g. Wyckoff T J et al, *J Biol Chem*. 1998 273(49):32369-72 and Williams A H et al, *Proc Natl Acad Sci USA*. 2007; 104 (34):13543-50) or can be straightforwardly retrieved using e.g. in silico alignments with acyl transferases having known hydrocarbon rulers.

The endogenous acyl transferases can be modified using any method commonly known in the art, including the replacement, addition or deletion of specific nucleotides or codons in order to change the specificity of the acyl chain length.

The acyl transferase activity is preferably introduced by the expression of at least one heterologous gene into the bacterium of the genus *Bordetella*, e.g. by expressing a heterologous acyl transferase. To this end, a single or a variety of heterologous acyl transferases may be introduced into the bacterium to obtain the modified LPS as disclosed herein. Such acyl transferases for use according to the invention are capable of transferring acyl chains of a certain (shorter) length to the lipid A moiety of the *Bordetella* LPS, thereby obtaining a lipid A moiety that is modified as compared to the lipid A moiety of a wild-type *Bordetella* LPS in that the length of at least one acyl chain is shorter. The expression of a heterologous acyl transferase may be achieved by any method known in the art.

In a particularly preferred embodiment, the introduction of a heterologous acyl transferase activity is accomplished by introducing a heterologous acyl transferase that is at least one of LpxA, LpxD, and LpxL. Alternatively or in addition, the introduced heterologous acyl transferase is LpxM. Such acyl transferases are known in the art and may be obtained or obtainable from any gram-negative bacterium that is not the wild-type *Bordetella bacterium* as defined herein. Furthermore, it is also contemplated that the heterologous acyl transferase may be obtained or obtainable from a *Bordetella* that is from a different species than the wild-type *Bordetella bacterium.*

The variation in the acyl chain length is determined by molecular rulers in the acyl transferases, which may vary between these enzymes of different bacterial species. Therefore in a preferred embodiment of the invention, the heterologous LpxA acyl transferase may transfer an acyl chain having a length of $C_2$, $C_4$, $C_6$, $C_8$, $C_{10}$ or $C_{12}$. Similarly, the heterologous LpxD acyl transferase may transfer an acyl chain having a length of $C_2$, $C_4$, $C_6$, $C_8$, $C_{10}$ or $C_{12}$, the heterologous LpxL acyl transferase may transfer an acyl chain having a length of $C_2$, $C_4$, $C_6$, $C_8$, $C_{10}$ or $C_{12}$ and/or the heterologous LpxM acyl transferase may transfer an acyl chain having a length of $C_2$, $C_4$, $C_6$, $C_8$, $C_{10}$ or $C_{12}$.

In a further preferred embodiment, the acyl transferase is obtained or obtainable from the genus *Neisseria*, the genus *Porphyromonas* or the genus *Pseudomonas*. Thus, the acyl transferase LpxA may be obtained or obtainable from the genus *Neisseria*, the genus *Porphyromonas* or the genus *Pseudomonas*, the acyl transferase LpxD may be obtained or obtainable from the genus *Neisseria*, the genus *Porphyromonas* or the genus *Pseudomonas*, and/or the acyl transferase LpxL may be obtained or obtainable from the genus *Neisseria*, the genus *Porphyromonas* or the genus *Pseudomonas*. However, it is clear for the skilled person that other acyl transferases may be equally suitable for use in the invention.

Preferred species of the genus *Neisseria* include *Neisseria meningitidis, Neisseria gonorrhoeae* and *Neisseria lactamica*, whereby the species *Neisseria meningitidis* is the most preferred.

Preferred species of the genus *Porphyromonas* include *Porphyromonas gingivalis, Porphyromonas asaccharolytica, Porphyromonas cangingivalis, Porphyromonas canoris, Porphyromonas cansulci, Porphyromonas catoniae, Porphyromonas circumdentaria, Porphyromonas crevioricanis, Porphyromonas endodontalis, Porphyromonas gingivicanis, Porphyromonas gulae, Porphyromonas levii, Porphyromonas macacae* and *Porphyromonas salivosa*, wherein the species *Porphyromonas gingivalis* is the most preferred.

Preferred species of the genus *Pesudomonas* include *Pesudomonas aeruginosa, Pesudomonas putida, Pesudomonas fluorescens* and *Pesudomonas syringae*, whereby the species *Pesudomonas aeruginosa* is the most preferred.

In a particularly preferred embodiment, the bacterium of the genus *Bordetella* has a genetic modification that introduces a heterologous acyl transferase activity, wherein the genetic modification introduces the expression of an lpxA gene, and wherein at least one of i) the lpxA gene is obtained or obtainable from the species *Pseudomonas aeruginosa*, ii) the lpxD gene is obtained or obtainable from the species *Pseudomonas aeruginosa* and iii) the lpxL gene is obtained or obtainable from the species *Neisseria meningitidis.*

In another embodiment, the invention pertains to a genetically modified bacterium of the genus *Bordetella*, wherein the bacterium is modified compared to the wild-type *Bordetella bacterium* in that it has a genetic modification that introduces a heterologous acyl transferase activity, and wherein the genetic modification introduces the expression of at least one heterologous lpxA gene, wherein the lpxA gene has a nucleotide sequence that encodes a LpxA acyl transferase having the sequence of SEQ ID NO: 1 or SEQ ID NO:6, or the nucleotide sequence that encodes the LpxA acyl transferase has at least 40, 50, 60, 65, 70, 75, 80, 85, 90, 95, 98, 99 or 100% amino acid sequence identity with SEQ ID NO: 1 or SEQ ID NO:6, wherein preferably the genetic modification introduces the expression of at least one heterologous lpxA gene, wherein the lpxA gene has a nucleotide sequence that encodes a LpxA acyl transferase having the sequence of SEQ ID NO: 1, or the nucleotide sequence that encodes the LpxA acyl transferase has at least 40, 50, 60, 65, 70, 75, 80, 85, 90, 95, 98, 99 or 100% amino acid sequence identity with SEQ ID NO: 1.

Alternatively or in addition, the invention relates to a genetically modified bacterium of the genus *Bordetella*, wherein the bacterium is modified compared to the wild-type *Bordetella bacterium* in that it has a genetic modification that introduces a heterologous acyl transferase activity, and wherein the genetic modification introduces the expression of at least one heterologous lpxL gene, wherein the lpxL gene has a nucleotide sequence that encodes a LpxL acyl transferase having the sequence of SEQ ID NO: 2, SEQ ID NO: 3 or SEQ ID NO: 32, or the nucleotide sequence that encodes the LpxL acyl transferase has at least 40, 50, 60, 65, 70, 75, 80, 85, 90, 95, 98, 99 or 100% amino acid sequence identity with SEQ ID NO: 2, SEQ ID NO: 3 or SEQ ID NO: 32, wherein preferably the lpxL gene has a nucleotide sequence that encodes a LpxL acyl transferase having the sequence of SEQ ID NO: 2, or the nucleotide sequence that encodes the LpxL acyl transferase has at least 40, 50, 60, 65, 70, 75, 80, 85, 90, 95, 98, 99 or 100% amino acid sequence identity with SEQ ID NO: 2.

Alternatively or in addition the invention concerns a genetically modified bacterium of the genus *Bordetella*, wherein the bacterium is modified compared to the wild-type *Bordetella bacterium* in that it has a genetic modification that introduces a heterologous acyl transferase activity, and wherein the genetic modification introduces the expression of at least one heterologous lpxD gene, wherein the lpxD gene has a nucleotide sequence that encodes a LpxD acyl transferase having the sequence of SEQ ID NO: 4, or the nucleotide sequence that encodes the LpxD acyl transferase has at least 40, 50, 60, 65, 70, 75, 80, 85, 90, 95, 98, 99 or 100% amino acid sequence identity with SEQ ID NO: 4.

In a further preferred embodiment, the sequence having a specific degree of sequence identity with SEQ ID NO: 1, 6, 2, 3, 32 or 4 as defined herein above retains respectively $LxpA_{(Pa)}$, $LpxA_{(Nm)}$, $LpxL_{(Nm)}$, $LpxL_{(Pg)}$, $LpxL_{(Pa)}$ or $LpxD_{(Pa)}$ acyl transferase activity.

In a further embodiment, the invention pertains to a genetically modified bacterium of the genus *Bordetella*, wherein the bacterium is modified compared to the wildtype *Bordetella bacterium* in that it has a genetic modification that introduces a heterologous acyl transferase activity, and wherein the genetic modification introduces the expression of at least one heterologous lpxA gene, wherein the lpxA gene has a nucleotide sequence that encodes a LpxA acyl transferase having the sequence as defined in GenBank WP_003092373.1, or the nucleotide sequence that encodes the LpxA acyl transferase has at least 40, 50, 60, 65, 70, 75, 80, 85, 90, 95, 98, 99 or 100% amino acid sequence identity with the sequence as defined in GenBank WP_003092373.1.

Alternatively or in addition, the invention relates to a genetically modified bacterium of the genus *Bordetella*, wherein the bacterium is modified compared to the wild-type *Bordetella bacterium* in that it has a genetic modification that introduces a heterologous acyl transferase activity, and wherein the genetic modification introduces the expression of at least one heterologous lpxL gene, wherein the lpxL gene has a nucleotide sequence that encodes a LpxL acyl transferase having the sequence as defined in GenBank WP_002222305.1 or as defined in GenBank WP_043876343.1, or the nucleotide sequence that encodes the LpxL acyl transferase has at least 40, 50, 60, 65, 70, 75, 80, 85, 90, 95, 98, 99 or 100% amino acid sequence identity with the sequence defined in GenBank WP 002222305.1 or as defined in GenBank WP 043876343.1 Alternatively or in addition the invention concerns a genetically modified bacterium of the genus *Bordetella*, wherein the bacterium is modified compared to the wild-type *Bordetella bacterium* in that it has a genetic modification that introduces a heterologous acyl transferase activity, and wherein the genetic modification introduces the expression of at least one heterologous lpxD gene, wherein the lpxD gene has a nucleotide sequence that encodes a LpxD acyl transferase having the sequence as defined in GenBank WP_003098585.1, or the nucleotide sequence that encodes the LpxD acyl transferase has at least 40, 50, 60, 65, 70, 75, 80, 85, 90, 95, 98, 99 or 100% amino acid sequence identity with the sequence as defined in GenBank WP_003098585.1.

In a further preferred embodiment, the invention pertains to a genetically modified bacterium of the genus *Bordetella*, wherein the modified bacterium comprises an LPS having a lipid A moiety that is modified as compared to the lipid A moiety of a wild-type *Bordetella* LPS in that the length of at least one acyl chain is shorter and wherein the bacterium is modified compared to the wild-type *Bordetella bacterium* in that it has a genetic modification that introduces at least one of a heterologous acyl transferase activity and heterologous UDP-2,3-diacylglucosamine pyrophosphatase activity. Preferably, the genetically modified bacterium has a genetic modification that introduces a heterologous acyl transferase activity and heterologous UDP-2,3-diacylglucosamine pyrophosphatase activity Preferably, such genetically modified bacterium has a lipid A moiety that is modified as compared to the lipid A moiety of a wild-type *Bordetella* LPS in that the length of the acyl chain at the 3 position of the modified lipid A moiety has a greater length than the acyl chain of the wild-type *Bordetella* lipid A moiety at the same 3 position.

The introduction of a heterologous UDP-2,3-diacylglucosamine pyrophosphatase activity is preferably accomplished by introducing a heterologous UDP-2,3-diacylglucosamine pyrophosphatase. Such UDP-2,3-diacylglucosamine pyrophosphatases are known in the art and may be obtained or obtainable from any gram-negative bacterium that is not the wild-type *Bordetella bacterium* as defined herein. Furthermore, it is also contemplated that the heterologous UDP-2,3-diacylglucosamine pyrophosphatases may be obtained or obtainable from a *Bordetella* that is from a different species than the wild-type *Bordetella bacterium*.

A preferred UDP-2,3-diacylglucosamine pyrophosphatase is LpxH. Hence, in a preferred embodiment, the genetic modification introduces the expression of a heterologous lpxH gene. Expression of the heterologous lpxH gene thus introduces heterologous UDP-2,3-diacylglucosamine pyrophosphatase activity in the cell.

The lpxH gene is preferably obtained or obtainable from the genus *Neisseria*, the genus *Porphyromonas* or the genus *Pseudomonas* as defined herein above. In a more preferred embodiment, the lpxH gene is obtained or obtainable from *Neisseria*, and more preferably the lpxH gene is obtained or obtainable from the species *Neisseria meningitidis*. Most preferably, the lpxH gene has a nucleotide sequence that encodes a LpxH that has at least 40, 50, 60, 65, 70, 75, 80, 85, 90, 95, 98, 99 or 100% amino acid sequence identity with SEQ ID NO:5.

In a further preferred embodiment, the sequence having a specific degree of sequence identity with SEQ ID NO:5 as defined herein above retains UDP-2,3-diacylglucosamine pyrophosphatase activity.

In a further preferred embodiment, the lpxH gene has a nucleotide sequence that encodes a LpxH that has at least 40, 50, 60, 65, 70, 75, 80, 85, 90, 95, 98, 99 or 100% amino acid sequence identity with a sequence as defined in GenBank WP_002222897.1.

The genetically modified bacterium of the genus *Bordetella* as defined herein may further comprise an endogenous lpxH gene, i.e. a gene expressing an endogenous LpxH (UDP-2,3-diacylglucosamine pyrophosphatase) or the genetically modified bacterium comprises solely the heterologous LpxH activity, e.g. does have endogenous LpxH activity. In a most preferred embodiment, the genetically modified bacterium does not express an endogenous LpxH having at least 40, 50, 60, 65, 70, 75, 80, 85, 90, 95, 98, 99 or 100% amino acid sequence identity with SEQ ID NO: 30.

In an alternative embodiment with respect to LpxH, the genetically modified bacterium comprises only the endogenous lpxH gene, i.e. expresses only the endogenous LpxH. In particular, the genetically modified bacterium thus does not comprise a gene that expresses a heterologous LpxH. More preferably, the genetically modified bacterium as defined herein does not express heterologous Neisserial LpxH and most preferably does not express heterologous *Neisseria meningitidis* LpxH. In a further preferred embodiment, the genetically modified bacterium only comprises a genetic modification that introduces the expression of at least one of a heterologous lpxA, a lpxL and a lpxD gene.

The genetically modified bacterium of the invention may contain a mixture of the different types of LPS. In particular, the modified bacterium may contain wild-type LPS in addition to LPS having a lipid A moiety having at least one shorter acyl chain as described herein. Alternatively, the genetically modified bacterium of the genus *Bordetella* predominantly or solely contains LPS with a shorter acyl chain as defined herein. Thus the modified bacterium may not contain, or only contains traces, of the wild-type LPS. To obtain a bacterium of the genus *Bordetella* that does not comprise, or only comprises traces, of wild-type LPS, the genetically modified bacterium as defined above may be further modified. To this end, in a preferred embodiment the genetically modified bacterium of the genus *Bordetella* as defined above further comprises a genetic mutation that reduces or eliminates the activity of at least one of LpxA, LpxD and LpxL acyl transferase encoded by respectively the endogenous lpxA, lpxD or endogenous lpxL gene.

Hence, such genetically modified bacterium may have a mutation that introduces a heterologous acyl transferase activity and a further mutation that decreases the corresponding endogenous LpxA and/or LpxD acyl transferase activity. Thus the overall LpxA and/or LpxD acyl transferase activity of the genetically modified bacterium may be increased, similar or decreased compared to the wild-type *Bordetella bacterium.*

The genetically modified bacterium of the genus *Bordetella* as defined herein may comprise a genetic mutation in an endogenous gene having the sequence of SEQ ID NO: 28, or a sequence having 60, 70, 75, 80, 85, 90, 95, 98, 99 or 100% sequence identity with SEQ ID NO: 28.

Alternatively or in addition, the genetically modified bacterium of the genus *Bordetella* as defined herein may comprise a genetic mutation in an endogenous gene having the sequence of SEQ ID NO: 29, or a sequence having 60, 70, 75, 80, 85, 90, 95, 98, 99 or 100% sequence identity with SEQ ID NO: 29.

Alternatively or in addition, the genetically modified bacterium of the genus *Bordetella* as defined herein may comprise a genetic mutation in an endogenous gene having the sequence of SEQ ID NO: 31, or a sequence having 60, 70, 75, 80, 85, 90, 95, 98, 99 or 100% sequence identity with SEQ ID NO: 31.

In a preferred embodiment, the expression of the endogenous lpxA gene, the endogenous lpxD gene and/or the expression of the endogenous lpxL gene is eliminated by inactivation of said gene, e.g. by disruption or deletion of the gene by methods known in the art per se.

In a further embodiment of the invention, the genetically modified bacterium of the genus *Bordetella* as defined herein is a genetically modified *Bordetella pertussis, Bordetella parapertussis* or *Bordetella bronchiseptica*. Preferably, the genetically modified bacterium is a genetically modified *Bordetella pertussis*. In a further preferred embodiment, the genetically modified bacterium is a *B. pertussis* Tohama I strain or a derivative thereof. Preferably, the derivative Tohama I strain is a streptomycin-resistant derivative of the Tohama I strain and most preferably the genetically modified bacterium is derived from the strain B213 or a derivative thereof. Alternatively, the genetically modified bacterium is a *B. pertussis* B1917 or B1920 strain or a derivative thereof.

In addition, the genetically modified bacterium of the invention may have one or several further modifications e.g. mutations that reduce LPS endotoxicity. For example, the *Bordetella* LPS of the invention may have a modified oligosaccharide structure so as to remove possible epitopes that are suspected to provoke autoimmune responses, and/or to increase binding to dendritic cells and adjuvant activity. Furthermore, the genetically modified bacterium of the invention as defined herein may further comprise a genetic modification that increases lipid A 3-O-deacylase activity.

As indicated above, it is herein understood that a shorter acyl chain does not include the complete absence of an acyl chain. Hence, a shorter acyl chain denotes the presence of an acyl chain. Nevertheless the modified lipid A moiety may, in addition to a shorter acyl chain, also have less acyl chains in comparison to the number of acyl chains of the wild-type *Bordetella* lipid A moiety. For example, the presence of at least partially 3-O-deacylated LPS and/or lipid A may further reduce LPS toxicity and may reduce the number and severity of side effects in the subject.

Hence, the genetically modified bacterium of the genus *Bordetella* may comprise a mixture of LPS molecules, wherein the LPS molecules may be a mix of i) wild-type LPS and/or ii) LPS having a lipid A moiety that is modified as compared to the lipid A moiety of a wild-type *Bordetella* LPS in that the length of at least one acyl chain is shorter and/or iii) LPS that is deacylated, e.g. 3-O-deacylated. Alternatively or in addition, the genetically modified bacterium of the invention may comprise a LPS molecule having a lipid A moiety that has at least one shorter acyl chain and is also 3-O-deacylated. The invention further relates to LPS obtained from such genetically modified bacterium.

Preferably, the genetically modified bacterium of the genus *Bordetella* as defined herein further comprises a nucleic acid encoding a polypeptide having SEQ ID NO: 25 (the PagL protein of *Bordetella bronchiseptica* and *Bordetella parapertussis*, GenBank WP_003813842.1), or a nucleic acid encoding a polypeptide having at least 25, 30, 40, 50, 60, 70, 80, 90, 95, 98 or 99% amino acid identity with SEQ ID NO. 25 and the polypeptide exhibits lipid A 3-O-deacylase activity.

OMV Comprising LPS of the Invention

In a third aspect, the invention pertains to an OMV comprising the *Bordetella* LPS as defined herein. OMV (also known as "blebs"), e.g. for use in vaccines, have traditionally been prepared by detergent extraction (a dOMV purification process), wherein detergents such as deoxycholate are used to remove LPS and increase vesicle release. An OMV preparation, prepared by sonication of cells and treatment with DOC, combined with alum adjuvant provided protection against pertussis challenge in a mouse model [Roberts, R., Vaccine 2008, 26, 4639-4646], which was comparable to the effect of a whole-cell vaccine. Another version of OMVs containing a PagL-deacylated modified LPS showed both protection and a lower reactogenicity, the latter determined in vivo by both weight gain and cytokine induction [Asensio, C. J., Vaccine 2011, 29, 1649-1656]. Another interesting finding with *B. parapertussis* OMVs was their cross-protection against both pertussis and *parapertussis* [Bottero, D. Vaccine 2013, 31, 5262-5268].

The LPS of most gram-negative bacteria, such as *Bordetella* is toxic. However, the *Bordetella* LPS of the invention may remain present in the OMV to a much larger degree than the toxic wild-type LPS. The detergent extraction process may therefore be replaced by a process that does not need the presence of a detergent. An OMV comprising a *Bordetella* LPS according to the invention therefore does not have to be a detergent-extracted OMV. It is understood however, that a process for preparing an OMV that is not a detergent-extracted OMV does not exclude the use of any detergents. The use of low concentration of detergent and/or the use of mild detergents are not excluded as long as most of the modified *Bordetella* LPS according to the invention, i.e. at least 5, 10, 20, 50, 60, 70, 80, 90, 95 or 99% of the modified *Bordetella* LPS, is maintained, e.g. as compared the amount of *Bordetella* LPS present in spontaneous or supernatant OMV from an equal amount of the same culture.

A preferred OMV comprising the *Bordetella* LPS of the invention is a supernatant or spontaneous OMV, i.e. sOMV as herein defined above, or a native OMV, i.e. nOMV as herein defined above. Alternatively the OMV comprising the *Bordetella* LPS of the invention is a detergent-extracted OMV. Methods for preparing dOMV, sOMV and nOMV are described in van de Waterbeemd et al (2010) and van de Waterbeemd et al (2013) (van de Waterbeemd B et al, Vaccine. 2010; 28(30):4810-6 and van de Waterbeemd B, *PLoS One*. 2013 31; 8(5):e65157) and WO2013/006055, all of which are incorporated herein by reference.

In a preferred embodiment, the OMV comprising the modified *Bordetella* LPS is obtainable or obtained from the genetically modified bacterium as defined above.

Compositions

In a fourth aspect, the invention relates to a composition comprising at least one of a *Bordetella* LPS, a genetically modified bacterium and an OMV as herein defined above. Preferably, the composition is a pharmaceutical composition. More preferably, the pharmaceutical composition further comprises a pharmaceutically acceptable excipient, carrier, medium or delivery vehicle as are conventionally known in the art (see e.g. "Handbook of Pharmaceutical Excipients", Rowe et al eds. 7th edition, 2012, www.pharmpress.com). Pharmaceutically acceptable stabilizing agents, osmotic agents, buffering agents, dispersing agents, and the like may also be incorporated into the pharmaceutical compositions. The preferred form depends on the intended mode of administration and therapeutic application. The pharmaceutical carrier can be any compatible, non-toxic substance suitable to deliver to the patient. The "active ingredients of the invention" are herein understood to be one or more of a *Bordetella* LPS, a genetically modified bacterium or an OMV as defined herein above.

Pharmaceutically acceptable carriers for parenteral delivery are exemplified by sterile buffered 0.9% NaCl or 5% glucose optionally supplemented with a 20% albumin. Alternatively, the active ingredients of the invention can be suspended in Phosphate buffered saline (PBS). Preparations for parenteral administration must be sterile. The parenteral route for administration of the active ingredients of the invention is in accord with known methods, e.g. injection or infusion by intravenous, intraperitoneal, intramuscular, and intra-arterial or intralesional routes. Alternatively, the composition maybe administrated by inhalation. The composition may be administrated continuously by infusion or by bolus injection. Preferably, the composition is administrated by bolus injection. A typical pharmaceutical composition for intramuscular injection would be made up to contain, for example, 1-10 ml of phosphate buffered saline comprising the effective dosages of the active ingredients of the invention. Methods for preparing parenterally administrable compositions are well known in the art and described in more detail in various sources, including, for example, "Remington: The Science and Practice of Pharmacy" (Ed. Allen, L. V. 22nd edition, 2012, www.pharmpress.com).

Medical Uses

In a fifth aspect, the invention pertains to a composition comprising at least one of the *Bordetella* LPS, a genetically modified bacterium and an OMV as defined herein above for use as a medicament. Put differently, the invention thus pertains to the use as medicament of at least one of a *Bordetella* LPS of the invention, a genetically modified bacterium of the invention, an OMV of the invention, and a pharmaceutical composition of the invention. The invention further concerns a method of treatment using at least one of the *Bordetella* LPS, a genetically modified bacterium and an OMV as defined herein above.

In a sixth aspect, the invention relates to a composition comprising at least one of the *Bordetella* LPS, a genetically modified bacterium and an OMV as herein defined above for use in a treatment comprising inducing an immune response in a subject. Alternatively, the invention relates to a composition comprising at least one of the *Bordetella* LPS, a genetically modified bacterium and an OMV as herein defined above for use in a treatment comprising stimulating an immune response in a subject. In particular, the invention thus relates to a method for vaccination.

In a preferred embodiment, the immune response is induced or stimulated against a *Bordetella* infection. To this end, three *Bordetella* species are known human pathogens (*B. pertussis, B. parapertussis* and *B. bronchiseptica*. In a particularly preferred embodiment, the immune response is therefore induced or stimulated against a *B. pertussis, B. parapertussis* or *B. bronchiseptica* infection.

*B. pertussis* and occasionally *B. parapertussis* cause pertussis or whooping cough in humans, and some *B. parapertussis* strains can colonise sheep. *B. bronchiseptica* rarely infects healthy humans, though disease in immunocompromised patients has been reported. *B. bronchiseptica* causes several diseases in other mammals, including kennel cough and atrophic rhinitis in dogs and pigs, respectively. Other members of the genus cause similar diseases in other mammals, and in birds (*B. hinzii, B. avium*).

Most preferably, the immune response is induced or stimulated against a *Bordetella pertussis* infection. In a further preferred embodiment, the invention pertains to a composition as defined herein above for use in a treatment comprising inducing or stimulating an immune response in a subject, wherein the treatment is the treatment of whooping cough. To this end, the subject is unvaccinated or may have been previously vaccinated against *Bordetella*. In addition or alternatively, the treatment is the prevention of whooping cough. It is further noted that the terms "whooping cough", "pertussis" and "100-day cough" may be used interchangeable herein.

In a preferred embodiment, the pharmaceutical composition of the invention is a vaccine. The vaccine can be an acellular vaccine preferably comprising at least one of a *Bordetella* LPS and an OMV as defined herein above. More preferably, the vaccine is a whole cell vaccine comprising at least a bacterium as herein defined above.

Hence the invention pertains to a (pharmaceutical) composition for use as a medicament, and preferably for use in a treatment comprising inducing or stimulating an immune response in a subject, wherein the composition is a whole cell vaccine comprising a genetically modified bacterium as defined above. The genetically modified bacterium of the invention may be a live or live attenuated bacterium or non-viable bacterium. Preferably, the bacterium is inactivated or killed using means known in the art per se. For example, the genetically modified bacterium may have been inactivated by freezing, heat treatment, mechanical disruption, chemical treatment or other methods known in the art of pharmacy and vaccination (see e.g. J. L. Pace, H. A. Rossi, V. M. Esposito, S. M. Frey, K. D. Tucker, R. I. Walker. Inactivated whole-cell bacterial vaccines: current status and novel strategies. Vaccine 16: 1563-1574 (1998)). Preferably the bacterium is a *Bordetella pertussis, Bordetella parapertussis* or *Bordetella bronchiseptica* and most preferably a *Bordetella pertussis.*

In an alternatively preferred embodiment, the (pharmaceutical) composition according to the invention is an acellular vaccine comprising a *Bordetella* LPS as defined herein above or an OMV as defined herein above.

The (acellular) vaccine of the invention may further comprise 1, 2, 3 or more immunogenic components of the bacterium of the genus *Bordetella*. Preferably, the (acellular) vaccine further comprises inactivated *Bordetella* toxin either alone or in combination with other *Bordetella* components such as filamentous haemagglutinin, fimbrial antigens and pertactin.

The modified LPS or OMV as defined herein may be used for eliciting a protective immune response against the *Bordetella bacterium* producing it, but alternatively may also be used and admixed to other compositions. In another embodiment, the invention therefore pertains to a compositions as defined above for use as a medicament, or for use in a treatment comprising inducing or stimulating an immune response in a subject, wherein the composition further comprises at least one non-*Bordetella* antigen. The antigen is any antigen as defined above. In particular, a *Bordetella* vaccine may be combined with other vaccines known in the art. In a preferred embodiment the *Bordetella* vaccine, and most preferably the whole cell *Bordetella* vaccine, is combined with at least one of a diphtheria and tetanus vaccine. In a most preferred embodiment, the (whole cell) *Bordetella* vaccine is combined with a diphtheria as well as a tetanus vaccine.

In seventh aspect, the LPS of the invention is for use as a suitable adjuvant substance. LPS is known in the art to be a suitable adjuvant for vaccination purposes, activating Toll like receptors and stimulating an innate immune response. Partially detoxified LPS and/or lipid A according to the invention may retain this immune stimulating (adjuvant) activity, while causing less toxicity related adverse side effects, such as local swelling, redness, pain and fever.

Pharmaceutically acceptable composition and vaccines according to the invention may be used in methods of treatment of subjects suffering from or at risk of acquiring a pathogenic, gram-negative bacterial infection, preferably a *Bordetella* infection, comprising administering the pharmaceutical composition, a whole cell or an a-cellular vaccine according to the invention. The use of specific adjuvants, the relative and absolute amounts of substances in the compositions and the doses regimen for the administration are known or may be determined by the skilled person and may be adapted for the circumstances such as the particular pathogenic infection or the status of the particular subject to be treated. The doses regimen may comprise a single dose but may also comprise multiple doses, for instance booster doses and may be administered orally, intranasally or parenterally. Various doses regimens for vaccination purposes are known in the art and may be suitably adapted by the skilled person.

In an eighth aspect, the invention relates to a modified *Bordetella* LPS of the invention for use as a Toll-like receptor 4 (TLR4) antagonist. Preferably, such antagonist may be used in the treatment or reduction of sepsis or against a massive immune reaction, such a cytokine storm. More preferably, the modified LPS of the invention be used for the treatment of a cytokine storm occurring during an influenza infection.

In a ninth aspect, the invention pertains to a process for producing a genetically modified bacterium of the genus *Bordetella*, the *Bordetella* LPS or an OMV of the invention. The process preferably comprises the steps of a) cultivating a genetically modified bacterium as herein defined above; and optionally b) at least one of purifying and inactivating the genetically modified bacterium. In addition, or instead of step b), the LPS or OMV may be extracted and/or purified. Methods for purifying and inactivating *Bordetella* are well-known in the art. Similarly, the purifying/extraction of LPS or OMV can be performed using any suitable method known in the art.

In a tenth aspect, the invention relates to producing a vaccine formulation comprising at least one of an inactivated modified *Bordetella bacterium*, OMV and LPS as defined herein. The process preferably comprises the steps of a)) cultivating a genetically modified bacterium as herein defined above; b) at least one of purifying and inactivating the genetically modified bacterium and c) formulating at least one of the *Bordetella bacterium*, OMV and LPS, optionally with further vaccine components, into a vaccine formulation. In addition, or instead of step b), the LPS or OMV may be extracted and/or purified.

It is further understood that the use of the composition in treatments of medical conditions as specified above also includes the use of the compositions for the manufacture of a medicament for the corresponding medical treatments, as well as, methods for treating a subject suffering from such medical conditions by administering an effective amount of the compositions to the subject.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Example 1

Material and Methods

Plasmids, Strains and Growth Conditions

Figure 1A:
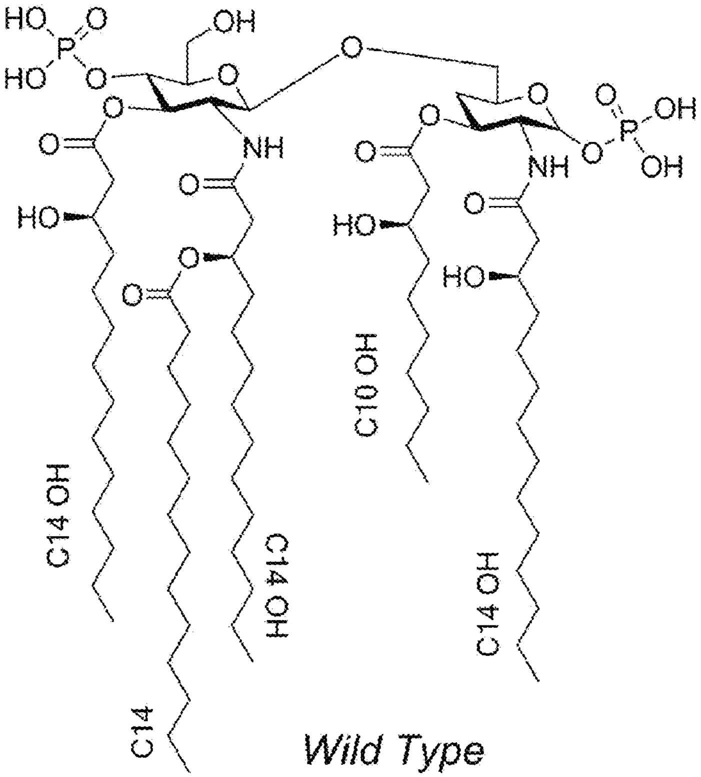
FIG. 1. Lipid A structure of wild-type and genetically modified *B. pertussis*. (A) Lipid A structure of wild-type *B. pertussis*. B) predicted lipid A structure of *B. pertussis* expressing $LpxA_{(Nm)}$ ΔlpxA. C) Lipid A structure of *B. pertussis* expressing $LpxA_{(Pa)}$ΔlpxA. D) Lipid A structure of *B. pertussis* expressing $LpxL_{(Nm)}$ΔlpxL and E) Lipid A structure of *B. pertussis* expressing $LpxL_{(Pg)}$ΔlpxL and F) Lipid A structure of *B. pertussis* expressing $LpxD_{(Pa)}$ΔlpxD and ΔlpxA, ΔlpxL and ΔlpxD indicate inactivation of the chromosomal lpxA, lpxL and ΔlpxD genes, respectively.

Table 1 lists all plasmids and strains used in this study. *B. pertussis* strains were cultured on Bordet-Gengou agar (Difco) supplemented with 15% defibrinated sheep blood (Biotrading) for 48 h at 35° C. To grow the bacteria in liquid cultures, bacteria were collected from solid medium and diluted in Verweij medium [16] to an $OD_{590}$ of 0.05 and incubated in 125-ml square media bottles with constant shaking at 175 rpm. In some assays, the bacteria were inactivated by incubation for 1 h at 60° C., resuspended in PBS and adjusted to an $OD_{590}$ of 0.5. *E. coli* strains were grown in lysogeny broth (LB) or LB agar at 37° C.

For all strains, media were supplemented with kanamycin (100 μg $ml^{-1}$), gentamicin (10 μg $ml^{-1}$), ampicillin (100 μg $ml^{-1}$), nalidixic acid (50 μg $ml^{-1}$), or streptomycin (300 μg $ml^{-1}$) when required, and with 0.1 or 1 mM isopropyl-β-D-1-thiogalactopyranoside (IPTG) for *E. coli* or *B. pertussis*, respectively, to induce protein expression.

TABLE 1

Used plasmids and strains

| Plasmids/Strains | Characteristics |
|---|---|
| | Plasmids |
| pMMB67EH | Broad host-range vector, Ptac, lacI$^q$, Amp$^R$ |
| pKAS32 | Allelic exchange suicide vector, Amp$^R$ |
| pMMB67EH-PagL$_{(Pa)}$ | pMMB67EH harboring pagL from *P. aeruginosa* PAO1 |
| pMMB67EH-LpxA$_{(Nm)}$ | pMMB67EH harboring lpxA from *N. meningitidis* H44/76 |
| pMMB67EH-LpxA$_{(Pa)}$ | pMMB67EH harboring lpxA from *P. aeruginosa* PAO1 |
| pMMB67EH-LpxL$_{(Nm)}$ | pMMB67EH harboring lpxL from *N. meningitidis* H44/76 |
| pMMB67EH-LpxL$_{(Pg)}$ | pMMB67EH harboring lpxL from *Po. gingivalis* ATCC33277 |
| pMMB67EH-LpxD$_{(Pa)}$ | pMMB67EH harboring lpxD from *P. aeruginosa* PAO1 |
| pKA32-ABGH LpxL::gm | pKAS32 derivative harboring lpxL$_1$-lpxL$_2$ knockout construct, Amp$^R$, Gm$^R$ |
| pRTP113368K2a | lpxL2 knockout construct, Amp$^R$, Kan$^R$ (kan in similar orientation as the operon) |
| pRTP113368 k1a | lpxL2 knockout construct, Amp$^R$, Kan$^R$ (kan in opposite orientation as the operon) |
| pRT669 | lpxA knockout construct, Amp$^R$, Kan$^R$ (kan in opposite orientation as the lpxA gene) |
| | Strains |
| | *Escherichia coli* |
| DH5α | F$^-$, Δ(lacZYA-argF)U169 thi-1 hsdR17 gyrA96 recA 1 endA 1 supE44 relA1 phoA ϕ80 dlacZΔM15 |
| SM10λpir | thi thr leu fhuA lacY supE recA::RP4-2-Tc::Mu λpir R6K Kan$^R$ |
| BL21(DE3) | Contains gene for T7 DNA polymerase |
| BL21-pLpxA$_{(Nm)}$ | BL21(DE3) carrying pMMB67EH-LpxA$_{(Nm)}$ |
| BL21-pLpxA$_{(Pa)}$ | BL21(DE3) carrying pMMB67EH-LpxA$_{(Pa)}$ |
| BL21-pLpxL$_{(Nm)}$ | BL21(DE3) carrying pMMB67EH-LpxL$_{(Nm)}$ |
| BL21-pLpxL$_{(Pg)}$ | BL21(DE3) carrying pMMB67EH-LpxL$_{(Pg)}$ |
| BL21-pLpxD$_{(Pa)}$ | BL21(DE3) carrying pMMB67EH-LpxD$_{(Pa)}$ |
| | *Bordetella pertussis* |
| B213 | Nal$^R$ Str$^R$ derivative of strain Tohama I |
| B213-pLpxA$_{(Pa)}$ | B213 carrying pMMB67EH-LpxA$_{(Pa)}$ |
| B213 ΔlpxA-pLpxA$_{(Pa)}$ | B213 carrying pMMB67EH-LpxA$_{(Pa)}$ with an inactivated lpxA gene |
| B213-pLpxL$_{(Nm)}$ | B213 carrying pMMB67EH-LpxL$_{(Nm)}$ |
| B213-pLpxL$_{(Pg)}$ | B213 carrying pMMB67EH-LpxL$_{(Pg)}$ |
| B213-pLpxD$_{(Pa)}$ | B213 carrying pMMB67EH-LpxD$_{(Pa)}$ |

AmpR, ampicilin resistance;
GmR, gentamicin resistance,
KanR, kanamycin resistance;
StrR, streptomycin resistance Genetic Manipulations PCRs were performed using High Fidelity Polymerase (Roche Diagnostics GmbH, Germany). PCR mixes consisted of 1 μl of template DNA, 200 μM dNTPs (Fermentas), 0.25 μM of different primer combinations (SEQ ID NO: 7-24, see Table 2), 0.5 U DNA polymerase, and PCR buffer. The mixtures were incubated for 10 min at 95° C. for DNA denaturation, followed by 30 cycles of 1 min at 95° C., 0.5 min at 58° C. and elongation at 72° C. for 1 min per kbp of expected amplicon size. The reaction was terminated with an extended elongation step for 10 min at 72° C. The resulting products were separated on 1% agarose gels by electrophoresis and visualized using ethidium bromide.

Genes encoding LPS biosynthesis enzymes of different bacteria were amplified by PCR from bacterial stocks and cloned into broad host-range expression vector pMMB67EH. To this end, PCR products and plasmid pMMB67EH-Pag$L_{(Pa)}$ were purified using the Clean-Up System and Plasmid Extraction kit, respectively, both provided by Promega. Purified plasmid and PCR products were digested with the restriction enzymes (Fermentas, The Netherlands) for which sites were included in the primers (SEQ ID NOs: 7-24, 26 and 27 see Table 2) and subsequently ligated together. To knock out the chromosomal lpxA and lpxL genes, the plasmids were used.

*E. coli* DH5a was transformed with ligation products or plasmids following standard protocols. Correct clones were elected by PCR, and plasmids were purified and sequenced at the Macrogen sequencing service (Amsterdam). Then, plasmids were transferred to *E. coli* strain SM10λpir by transformation and subsequently to *B. pertussis* strain B213 by conjugation using ampicillin and nalidixic acid for selection and counter selection, respectively. To generate chromosomal mutations, the knockout plasmids, which contained a rpsL gene conferring streptomycin sensititvity (Skorupsky and Taylor, 1996) were integrated into the chromosome by single crossover by selecting for kanamycin- or gentamicin-resistant transconjugants; the resulting bacteria had lost streptomycin resistance. Subsequently, to select for plasmid loss by a second crossover, bacteria were cultured in liquid medium and mutants were selected on plates with streptomycin and kanamycin or gentamicin. The presence of the plasmids in *B. pertussis* transconjugants and the proper generation of knockout mutants were verified by PCR.

To express the target enzyme Lpx$D_{Pa}$ in *B. pertussis*, vector pMMB67EH was used lpxD was amplified by PCR from *P. aeruginosa* strain PAO1 using a proof—reading enzyme (High Fidelity Polymerase, Roche Diagnostics GmbH) with primers LpxD-Fw Pa Ndel (having SEQ ID NO:26) and LpxD-rev-His Pa HindIII (having SEQ ID NO:27). The primers both contain sequences for restriction enzymes to facilitate cloning and the reverse primer also contains a sequence encoding a Hiss-tag to facilitate the detection of the recombinant protein via western blotting. After cloning the PCR product behind the tac promoter on pMMB67EH, the correct sequence of the insert was confirmed.

RNA Extraction and RT-PCR

To obtain RNA, cells from exponentially growing cultures were collected by centrifugation for 10 min at 5000 rpm in an Eppendorf Centrifuge 5424, adjusted to an $OD_{550}$ of 4, and resuspended in trizol (Invitrogen, U.K.). Then, 200 μl of chloroform were added per ml of trizol, followed by centrifugation at 5000 rpm for 30 min. The resulting upper layer was mixed with an equal amount of ice-cold 75% ethanol. Next, RNA was isolated using the Nucleospin RNA II kit (Macherey-Nagel, U.S.A.) according to the manufacturer's instructions. The resulting solution was treated with Turbo DNA free (Ambion, Germany) for 1 h at 37° C. to remove genomic DNA followed by DNase inactivation according to recommendations of the manufacturer to generate pure RNA. This was used immediately to generate cDNA using the Transcriptor High Fidelity cDNA Synthesis Kit (Roche, The Netherlands). RNA, cDNA and chromosomal DNA were used as templates in PCRs with primers (see Table 2, SEQ ID NOs: 7-24, 26 and 27) to determine the generation of specific transcripts.

Electrophoretic Techniques

Whole cell lysates were adjusted to an $OD_{600}$ of 5.0 solubilized in 1:1 in double-strength sample buffer and heated for 10 min at 100° C. For LPS visualization, after boiling, whole cell lysates were treated with proteinase K during 1 h at 37° C. Proteins and LPS were separated on 14% and 16% acrylamide gels, respectively, after which they were stained with Coomassie brilliant blue G250 or silver stain, respectively.

LPS Purification and Analysis

LPS were extracted from bacteria with hot phenol-water (Westphal, 1965) and purified further by solid phase extraction (SPE) on C8 reversed-phase cartridges. Briefly, bacteria were collected from culture suspensions by centrifugation, suspended with water at 70° C. and mixed with 0.8 volumes of phenol at the same temperature. After separating the aqueous and phenolic phase by centrifugation, the aqueous phase was prepared for SPE by adding one volume of 0.356 M triethylammonium acetate (TEAA) pH 7 (solvent A) and ⅓ volume of 2-propanol:water:triethylamine:acetic acid (70:30:0.03:0.01, v/v) pH 8.9 (solvent B). LPS extracts were purified simultaneously by SPE on reversed-phase Sep-Pak C8 cartridges (3 ml syringe-barrel-type Vac cartridge, 200 mg of C8 resin, Waters) using a 20-position vacuum manifold (Waters). Cartridges were conditioned for SPE by applying consecutively 3×1 ml of solvent B, 2-propanol: water:triethylamine:acetic acid (10:90:0.03:0.01, v/v) pH 8.9 (solvent C), 0.07 mM TEAA pH 7 (solvent D) and solvent A under vacuum. Then, samples were loaded into the cartridges and each cartridge was washed with 3×1 ml of solvents A, D and C, in this order. LPS were eluted from the columns by applying 2×0.3 ml of solvent B. Eluates were dried in a centrifugal vacuum concentrator and suspended in water. The purity and integrity of purified samples were judged by Tricine-SDS-PAGE combined with LPS silver and Coomassie staining. For analysis of lipid A structure, negative-ion nano-electrospray ionization—Fourier transform-mass spectrometry (nano-ESI-FT-MS) of purified LPS was performed on an LTQ Orbitrap XL instrument (Thermo Scientific). LPS samples were dissolved in a mixture of 2-propanol, water and triethylamine (50:50:0.001, vol/vol/vol) pH 8.5 and infused into the mass spectrometer by nano-ESI using gold-coated pulled glass capillaries, as described previously (Pupo et al, 2014) (Kondakov, A., and Lindner, B. (2005) Structural characterization of complex bacterial glycolipids by Fourier transform mass spectrometry. Eur J Mass Spectrom (Chichester, Eng) 11, 535-546). The spray voltage was set to −1.2 kV and the temperature of the heated capillary to 250° C. Under these ionization conditions no appreciable fragmentation of LPS was produced. To record lipid A mass spectra, nano-ESI-FT-MS of LPS was performed with in-source collision-induced dissociation (CID) at a potential difference of 100 V. In-source CID under this setting produced intense fragment ions corresponding to intact lipid A domains, which originate from the rupture of the labile linkage between the non-reducing lipid A glucosamine and Kdo, with minimal lipid A fragmentation, as shown in the mass spectra of the lipid A of the wild-type B213 strain (FIG. 3*a*).

Eukaryotic Cell Lines Culture and Stimulation

Human NF-κB/SEAP reporter HEK293 cells transfected either with human or mouse TLR4 in combination with MD-2 and CD14 were purchased from InvivoGen. Both cell lines contain an NF-κB-inducible secreted embryonic alkaline phosphatase (SEAP) reporter gene, which is expressed after TLR signaling. The cells were grown in HEK-Blue culture medium as described before [19]. SEAP was detected in culture supernatants after adding the substrate Quanti-Blue (InvivoGen). The human monocytic cell line MonoMac6 (MM6; DSMZ) was grown in Iscove's modified Dulbecco's medium (IMDM; Gibco) supplemented with 10% heat-inactivated FCS, 50 U/ml penicillin, and 50 μg/ml streptomycin. All cell lines were cultured at 37° C. in a 5% saturated $CO_2$ atmosphere.

For TLR4 signaling, HEK-Blue cell lines ($2.5\times10^4$) were incubated with serial dilutions of purified LPS or heat-inactivated whole cell preparations in a 96-well plate. After 2, 4 or 6 h of incubation at 37° C., supernatants were collected and incubated for 2 h with Quanti-Blue substrate and the $OD_{630}$ was measured using an enzyme-linked immunosorbent assay (ELISA) reader.

Results

Expression of Heterologous LpxLs and LpxAs in *B. pertussis*

To modify the length of the primary acyl chains at the 3 and 3' positions and of the only secondary acyl chain in *B. pertussis* lipid A, we made use of LpxA and LpxL acyl transferases from other bacteria. *B. pertussis* lipid A contains 3OH—C10 and 3OH—C14 chains at the 3 and 3' positions, respectively (FIG. 1*a*). We investigated whether the replacement of LpxA by the corresponding enzymes from *Neisseria meningitidis* ($LpxA_{(Nm)}$) or *Pseudomonas aeruginosa* ($LpxA_{(Pa)}$) would result in modifications of the acyl chains. Similarly, we investigated whether substitution of LpxL of *B. pertussis* by the corresponding enzymes from *Porphyromonas gingivalis* ($LpxL_{(Pg)}$) or *N. meningitidis* ($LpxL_{(Nm)}$) would result in a modification of the acyl chains.

The genes for the heterologous enzymes were cloned into the broad host-range expression vector pMMB67EH under the control of the tac promoter. The expression of the recombinant enzymes LpxA and LpxL was first evaluated in the cloning host *E. coli* BL21(DE3) by RT-PCR (data not shown). These assays confirmed the presence of transcripts of the genes of interest when the bacteria were grown with IPTG whilst these transcripts were much less abundant or undetectable when the bacteria were grown in the absence of IPTG. Protein expression was also detected by SDS-PAGE; LpxA proteins were expressed in higher abundance than LpxL proteins (data not shown).

Figure 1B:
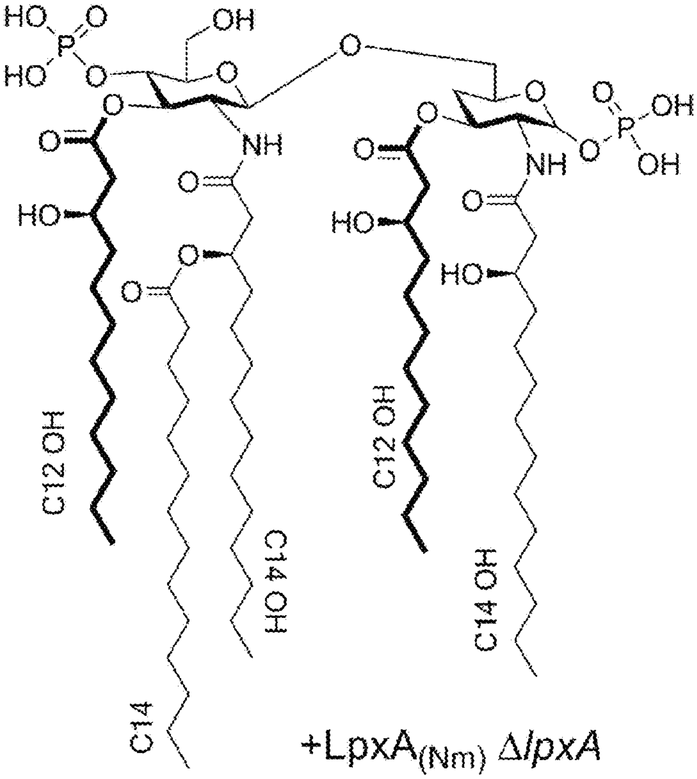

The plasmids were then transferred to *B. pertussis* strain B213, a derivative of strain Tohama I (Table 1). Surprisingly, although pMMB67EH-$LpxA_{(Nm)}$ was successfully introduced in *B. pertussis* as evidenced by PCR, the transconjugants failed to grow after being replated on plates containing ampicillin for plasmid maintenance and no IPTG. Thus, apparently, even uninduced expression levels of LpxA from *N. meningitidis* are lethal in *B. pertussis*, although this is not the case in *E. coli*. The LPS predicted to be produced by the introduction of the $Lpx_{(Nm)}$ enzyme is depicted in FIG. 1B. We noticed also that expression of $LpxL_{(Nm)}$ impaired growth (Fig S1C). All other recombinant strains grew as the wild-type (FIG. 2 (S1C)).

Expression of the recombinant protein $LpxD_{(Pa)}$ was first tested in *Escherichia coli* strain BL21(DE3), to which the plasmid was transferred. The resulting strain is called BL21-$pLpxD_{Pa}$. Addition of IPTG to the culture did not affect growth (data not shown). Expression of the protein was not detected on regular Coomassie blue-stained gels on which whole cell lysates of BL21(DE3) and BL21-$pLpxD_{Pa}$ were analyzed. However, Western blotting assays showed a reaction of an anti-Hiss-tag antibody with a band of the expected size of $LpxD_{Pa}$ (36.4 kDa) in BL21-$pLpxD_{Pa}$ (data not shown), which was not present in the sample of BL21(DE3). Next, the plasmid was transferred to *B. pertussis* B213 by conjugation using *E. coli* strain SM10λpir as donor, and two transconjugants were saved. In the presence of 1 mM IPTG, both clones showed a growth defect as compared with the parent (FIG. 2B), which was more pronounced for clone 5. Western blotting assays confirmed the expression of the enzyme in both clones (data not shown), while no differences in expression levels were observed.

Analysis of Recombinant Lipid a Structures

Figure 1C:
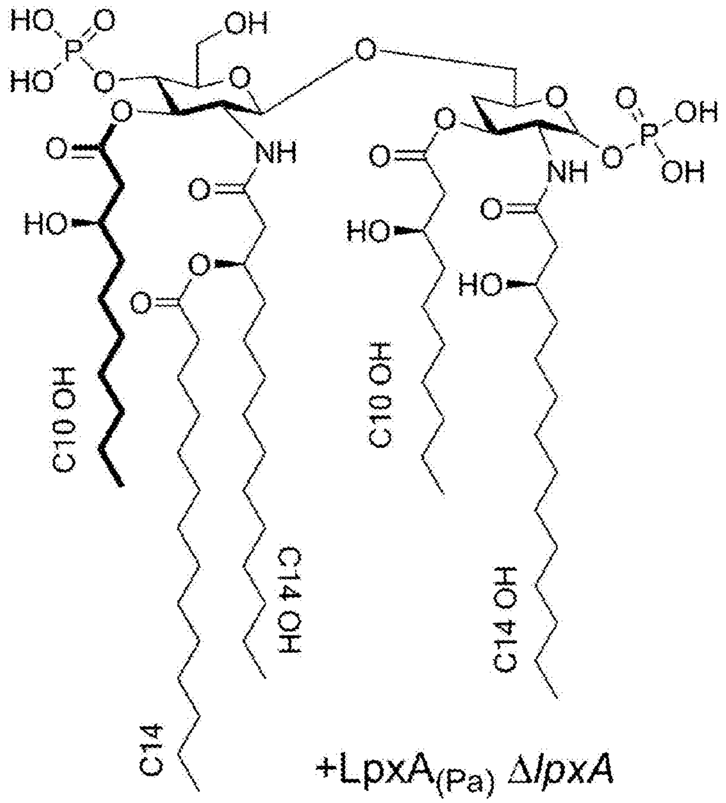

The lipid A structures were then analyzed by nano-ESI-MS using purified LPS extracted from whole cells grown in the presence of 1 mM IPTG for 12 h (logarithmic growth). For the wild-type strain, a major peak was observed at m/z 1557.97 that corresponds with the expected bis-phosphorylated penta-acetylated lipid A (FIG. 3A). In the strain expressing $LpxA_{(Pa)}$, the spectrum revealed, besides the ion at m/z 1557.97, two additional ions at m/z 1501.91 and 1529.94 (FIG. 3B). The ion at m/z 1501.91 corresponds with a substitution of the primary 3OH—C14 acyl chain at the 3' position by 3OH—C10 (FIG. 1C), whilst the m/z 1529.94 ion indicates the presence of a hydroxylated fatty acid with an intermediary C12 chain length. The relative abundance of the two new species was only 48 and 75% relative to the wild-type structure at m/z 1557.97, which could be due to the expression of the endogenic lpxA on the chromosome. Therefore, we decided to knock out the chromosomal lpxA copy. MS analysis of the resulting strain evidenced the complete loss of the m/z 1557.97 ion and a drastic decrease of the abundance of the m/z 1529.94 ion leaving a major peak of m/z 1501.91 corresponding to the substitution (FIG. 1C and FIG. 3C).

Figure 1D:
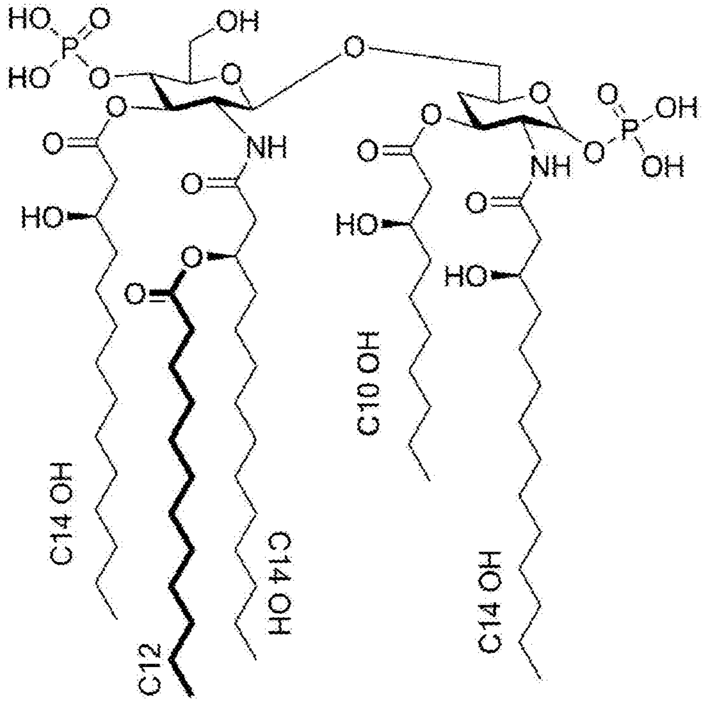

MS analysis of B213-$LpxL_{(Nm)}$ detected the wild-type m/z 1557.97 ion as a minor species, whilst a major peak of m/z 1529.94 corresponded with a substitution of the secondary C14 acyl chain by C12 (FIG. 1D and FIG. 3D). Attempts to delete the chromosomal lpxL failed. *B. pertussis* contains two adjacent lpxL homologues on the chromosome, but only one, called lpxL2, is active under laboratory growth conditions [20]. Different constructs were used to delete the lpxL2 gene partially or completely; however, in spite of considerable efforts, we could not obtain the desired knock-out.

Figure 1E:
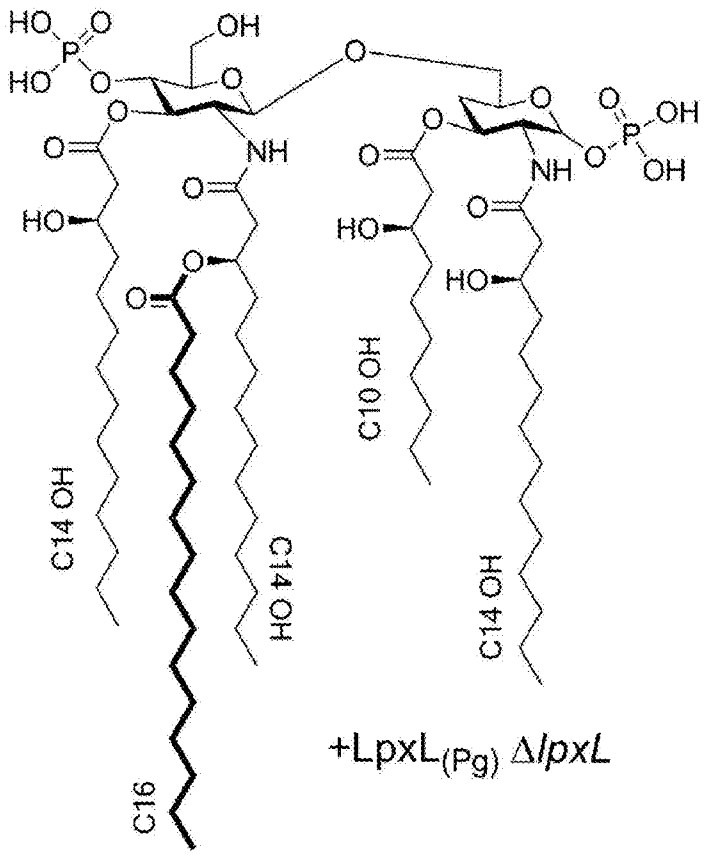
Figure 1F:
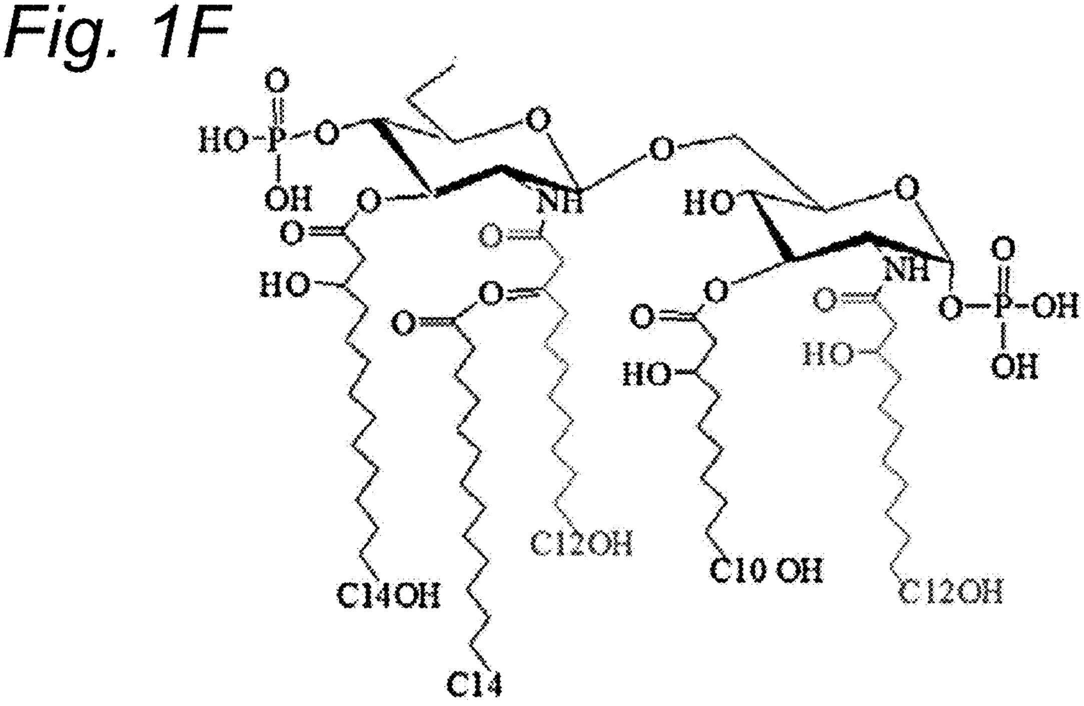
Figure 2A:
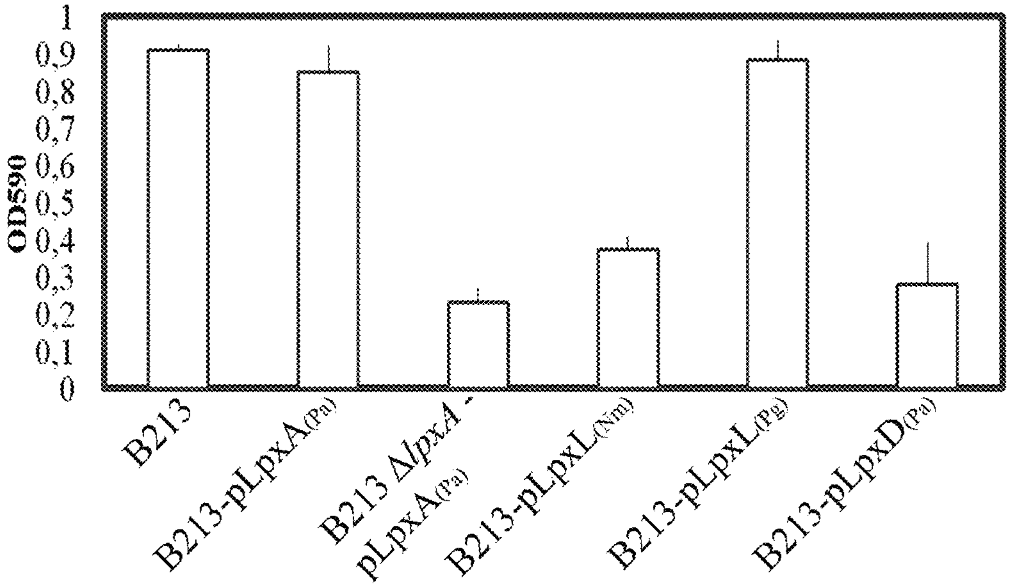
FIG. 2. Implication of the expression of heterologous enzymes on growth. A) The $OD_{590}$ of cultures of B213 and derivatives expressing $LpxL_{(Nm)}$, $LpxA_{(Pa)}$, or $LpxL_{(Pg)}$ from pMMB67EH plasmids, after 18 h of growth in Verweij medium in the presence of 1 mM IPTG is shown. The starting $OD_{590}$ was 0.05. Data are from one representative experiment performed in duplicate of which average and standard variation are given. The growth defect of the strain expressing $LpxL_{(Nm)}$ was reproduced in two additional experiments. B) $LpxD_{(Pa)}$ The OD at 590 nm ($OD_{590}$) of cultures of B213 and B213-pLpx$D_{Pa}$ clone 4 (cl4) and clone 5 (cl5) after 12 and 24 h of growth in liquid Verweij medium in the presence of 1 mM of IPTG is shown. The starting $OD_{590}$ was 0.05.
Figure 2B:
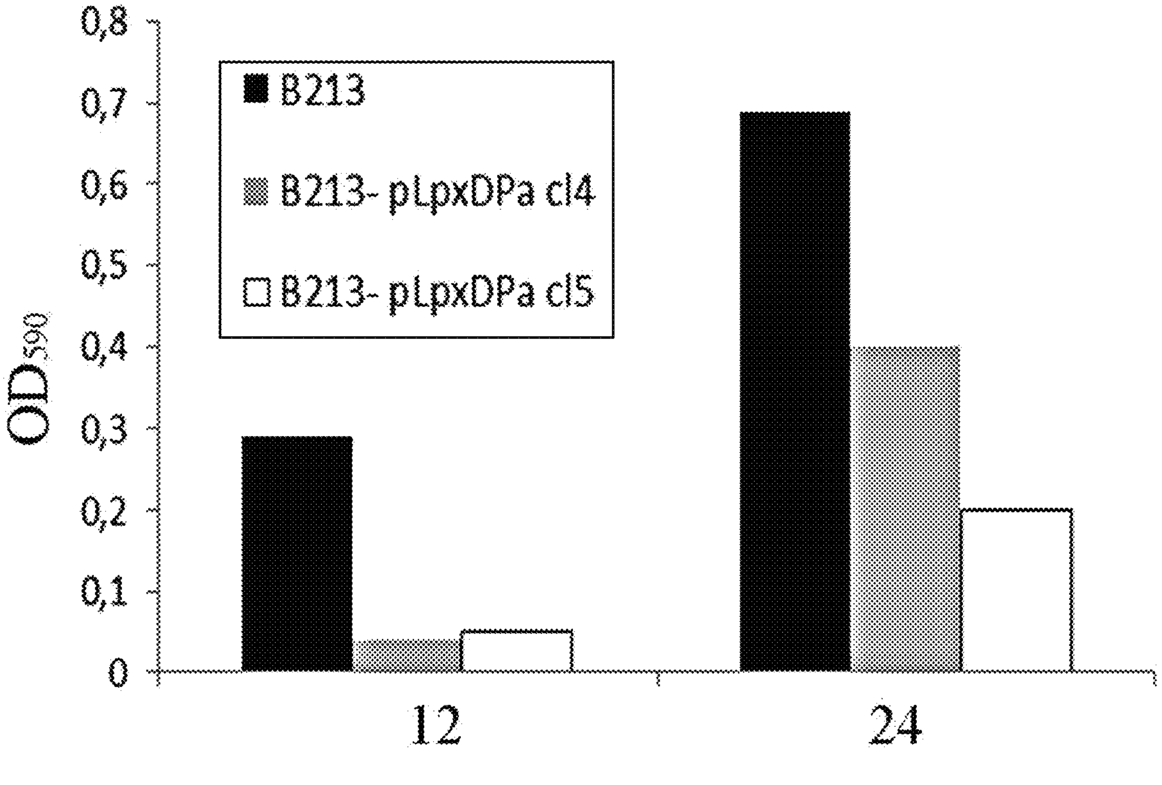

Apparently, the lpxL2 gene sequence rather than the enzyme is essential for *B. pertussis* considering that expression of $LpxL_{(Nm)}$ in the wild-type strain already altered about 65% of the lipid A structure. This could be due to a polar effect of lpxL2 disruption on expression of the downstream gene dapF, which encodes for L,L-DAP epimerase that catalyzes L,L-diaminopimelate (DAP) into meso-DAP Meso-DAP is vital for cell wall synthesis and lysine biosynthesis. However, also attempts to inactivate the $lpxL_2$ gene in the presence of meso-DAP failed. MS analysis of B213-$LpxL_{(Pg)}$ evidenced a drastic reduction in the abundance of the m/z 1557.98 ion and the appearance of a new peak of m/z 1586.01 that corresponds with a substitution of the C14 by a C16 chain (FIG. 1E and FIG. 2*e*). In summary, heterologous expression of $LpxA_{(Pa)}$, $LpxL_{(Nm)}$, and $LpxL_{(Pg)}$ in *B. pertussis* resulted in LPS alterations as depicted in FIG. 1.

Analysis of B213-$pLpxD_{(Pa)}$ clones 4 and 5 revealed that in both mutants, ions at m/z 1557.97 were found corresponding with the standard penta-acylated lipid A as found in the wild-type (FIGS. 3F and 3G). In addition, abundant ions at m/z 1529.94 and 1501.91 were found corresponding with the reduction of the length of one or two acyl chains from 3OH—C14 to 3OH—C12, respectively (FIGS. 3F and 3G). The abundance of these additional major ions varied between both clones; the relative abundance of the peak at m/z 1529.94 was lower in clone 5 than in clone 4, and vice versa for the peak at m/z 1501.91. Thus, clone 5 had a higher amount of lipid A molecules with an entire modification of the length of both acyl chains in the lipid A than clone 4, but considerable amounts of unaltered lipid A remained in both cases. These results show that the expression of $LpxD_{Pa}$ modified the structure of lipid A as shown in FIG. 1.

Differential Activation of TLR4 by the LPS Variants

Figure 4A:
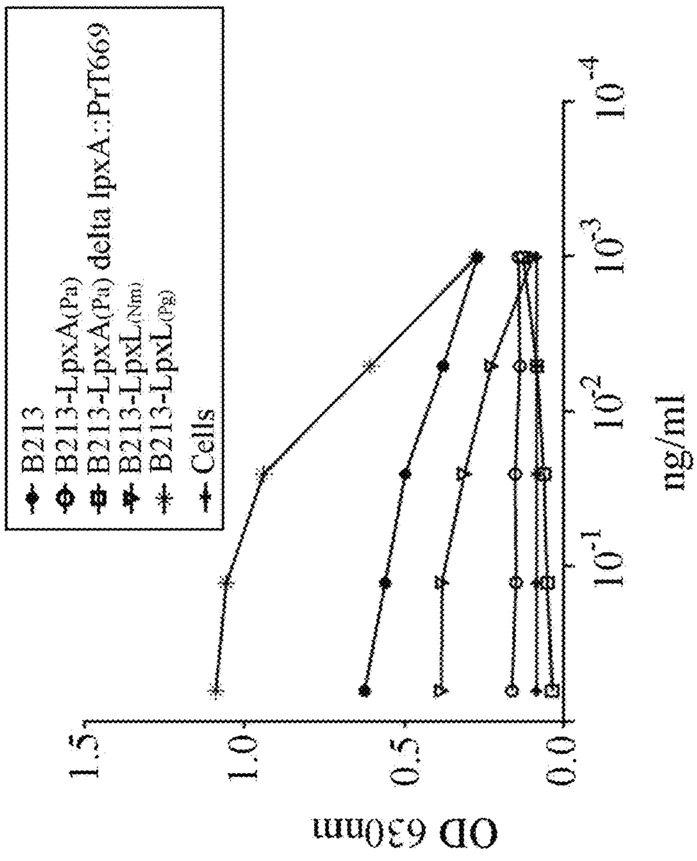
FIG. 4. Stimulation of HEK293 cells expressing hTLR4 (A, C) or mTLR4 (B, D) with purified LPS (A, B) or whole-cell preparations of B213 and LPS mutant derivatives (C, D). LPS preparations and bacterial suspensions, adjusted to an $OD_{590}$ of 0.1, were serially diluted. After incubation for 2 h with HEK293 cells expressing mTLR4 or 4 h with HEK293 cells expressing hTLR4, alkaline phosphatase activity was determined by adding substrate and measuring the OD at 630 nm. One representative experiment is shown.

We next investigated whether the altered structure affects the toxicity of the LPS. To this end, purified LPS preparations were added to cultures of HEK293 cells expressing the human or mouse TLR4 complex (hTLR4 and mTLR4, respectively). After exposure, the activation of the receptor was evaluated by the expression of a reporter gene (FIG. 4). Interestingly, LPS from B213-$pLpxA_{(Pa)}$ stimulated hTLR4 much less than LPS from the wild-type strain (FIG. 4A). The residual activation still detected was due to the expression of the chromosomal lpxA gene, since it was totally eliminated after inactivation of this gene (FIG. 4A). Thus, the length of the primary acyl chain at the 3' position is relevant for the activation of hTLR4 by pertussis LPS. LPS from B213-$pLpxL_{(Nm)}$ and B213-$pLpxL_{(Pg)}$ reduced and increased hTLR4 activation, respectively (FIG. 4A). Hence, stimulation of hTLR4 correlates with the length of the secondary acyl chain in the order C16>C14>C12.

Figure 3:
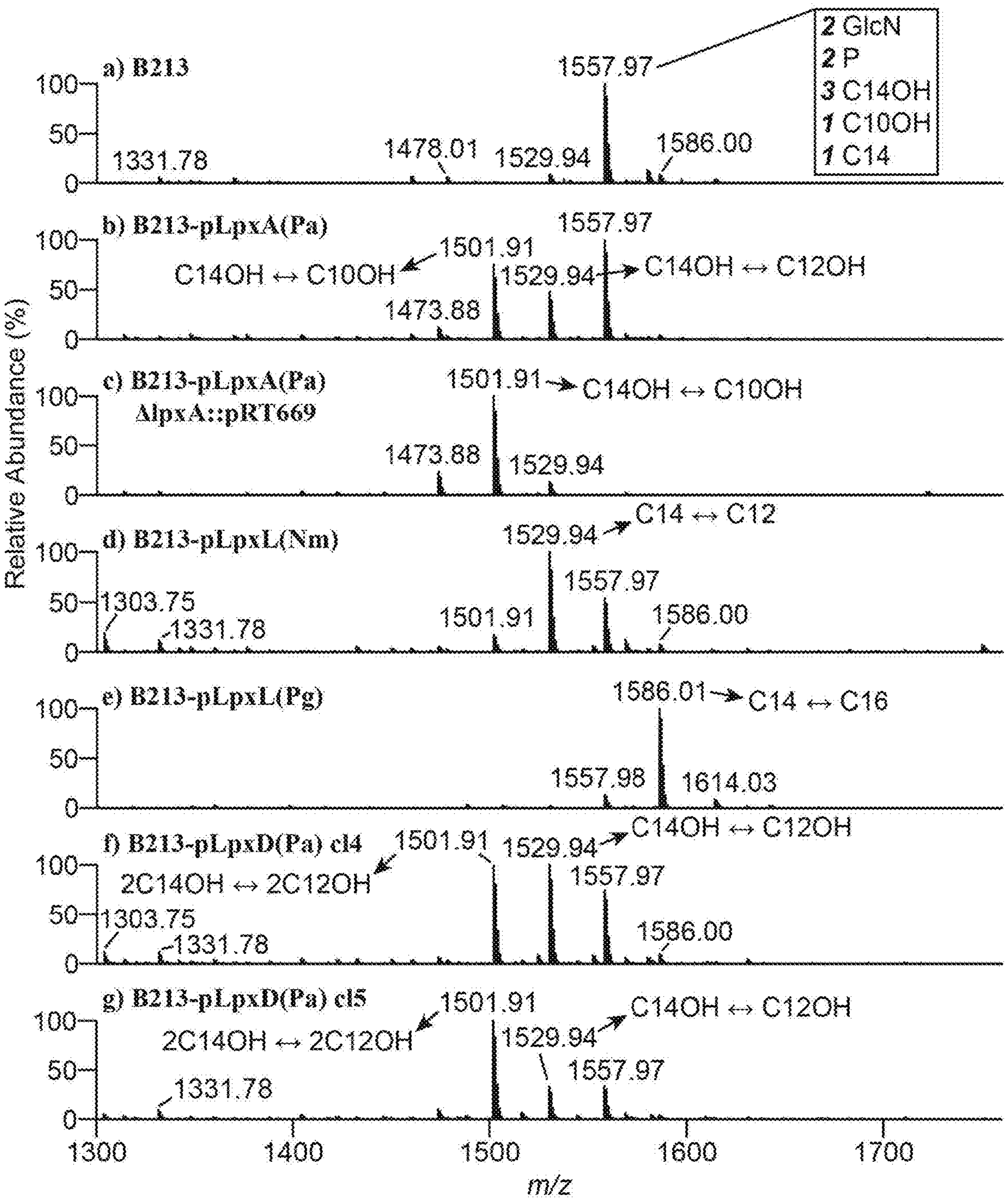
FIG. 3. Structural analysis by ESI-MS of lipid A. Negative-ion lipid A mass spectra were obtained by in-source collision-induced dissociation nano-ESI-FT-MS of intact LPS isolated from cells of B213, B213 expressing $LpxA_{(Pa)}$ (B213-p$LpxA_{(Pa)}$), ΔlpxA mutant of B213 expressing $LpxA_{(Pa)}$ (B213ΔlpxA-p$LpxA_{(Pa)}$) backgrounds, B213 expressing $LpxL_{(Nm)}$ (B213-p$LpxL_{(Nm)}$), B213 expressing $LpxL_{(Pg)}$ (B213-p$LpxL_{(Pg)}$) and B213 expressing $LpxD_{(Pa)}$ (B213-p$LpxD_{(Pa)}$) (clones 4 and 5). Bacteria were grown for 12 h in liquid Verweij medium in the presence of 1 mM of IPTG. A major singly-deprotonated ion at m/z 1557.97 was interpreted as the typical *B. pertussis* lipid A structure: a diglucosamine (2 GlcN) penta-acylated (three 3OH—C14, one 3OH—C10 and one C14) with two phosphates residues (2 P) as illustrated in FIG. 1. Additional singly-deprotonated lipid A ions were detected in different derivatives and their interpretations are also indicated. Only the m/z range covering lipid A ions is shown.
Figure 5:
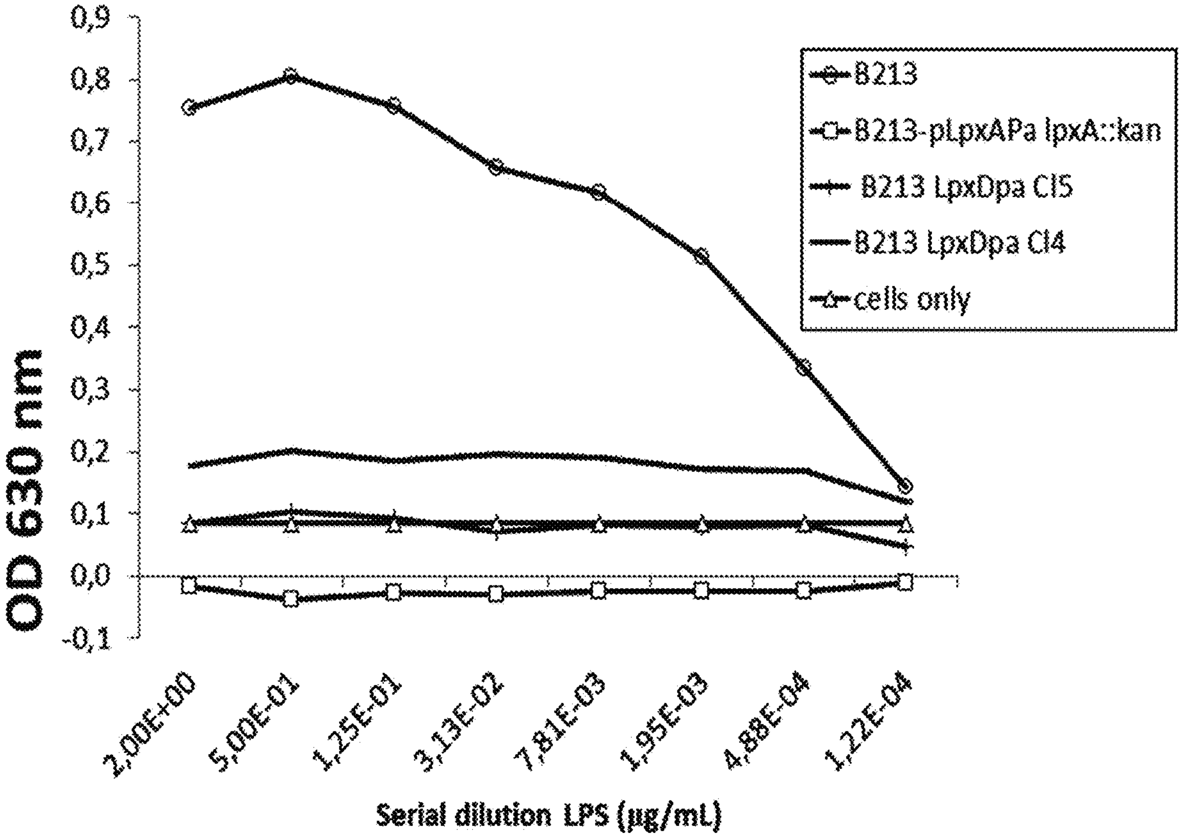
FIG. 5. Stimulation of HEK293 cells expressing hTLR4 with LPS purified from B213, B213ΔlpxA-pLpxA$_{(Pa)}$, and B213-pLpxD$_{(Pa)}$ cl4 and cl5. Purified LPS at a concentration of 2 μg/ml was serially diluted, added to the cultured cells and incubated for 4 h. The OD at 630 nm resulting of SEAP activity is provided.

To evaluate the toxicity of the altered LPS of the strains expressing $LpxD_{(Pa)}$, preparations of purified LPS from both mutants and the wild-type were added to cultures of HEK-Blue cells expressing the human TLR4 receptor (hTLR4) (InvivoGen). As a negative control, we used purified LPS from strain B213ΔlpxA-$pLpxA_{(Pa)}$, which contains a 3OH—C10 acyl chain instead of 3OH—C14 at the 3' position and did not activate hTLR4. The activation of the receptor was evaluated by the expression of a SEAP reporter gene after 4 h of exposure, and the results are presented in FIG. 5. LPS from B213-$pLpxD_{(Pa)}$ clone 4 and clone 5 showed considerably lower activity than wild-type LPS. The SEAP activity of cells stimulated with LPS from clone 5 was as low as that of non-stimulated cells, while cells stimulated with LPS from clone 4 showed low residual activity, perhaps in agreement with a somewhat less efficient modification of the acyl chains in this clone (FIG. 3). Cells stimulated with LPS from B213ΔlpxA-$pLpxA_{(Pa)}$ showed even lower SEAP activity than non-stimulated cells.

Figure 4B:
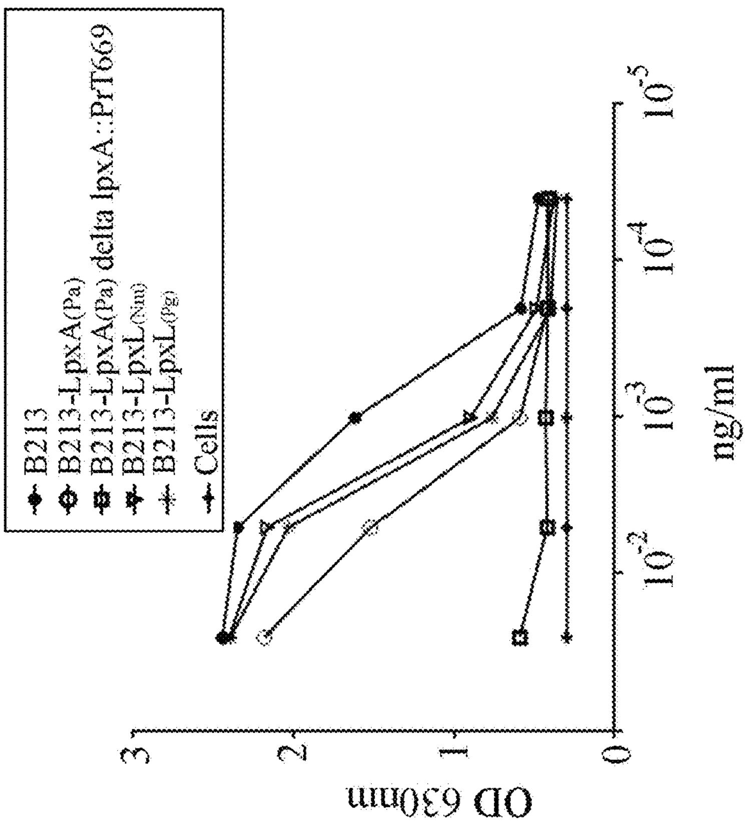
Figure 4C:
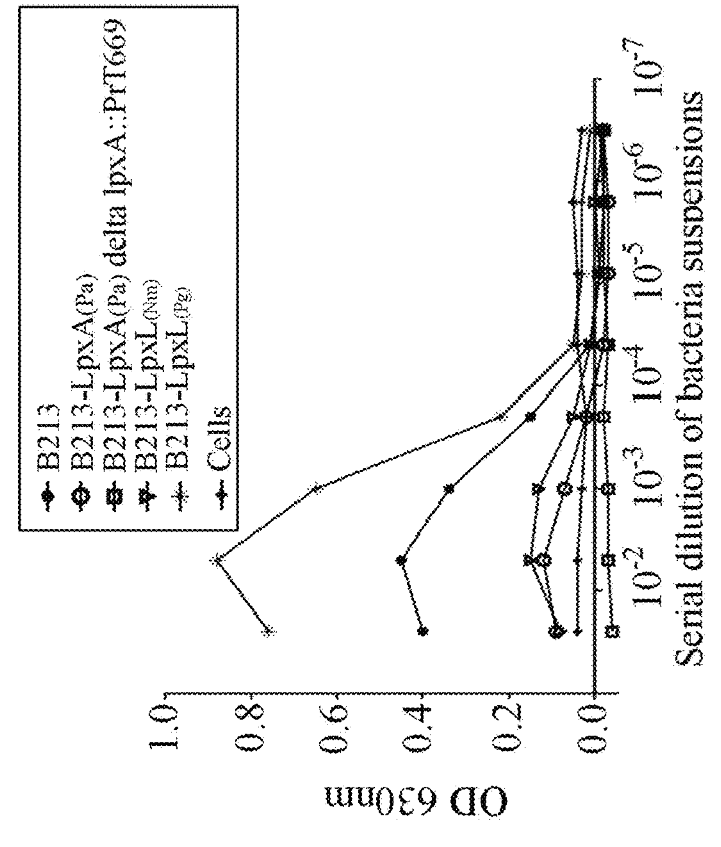
Figure 4D:
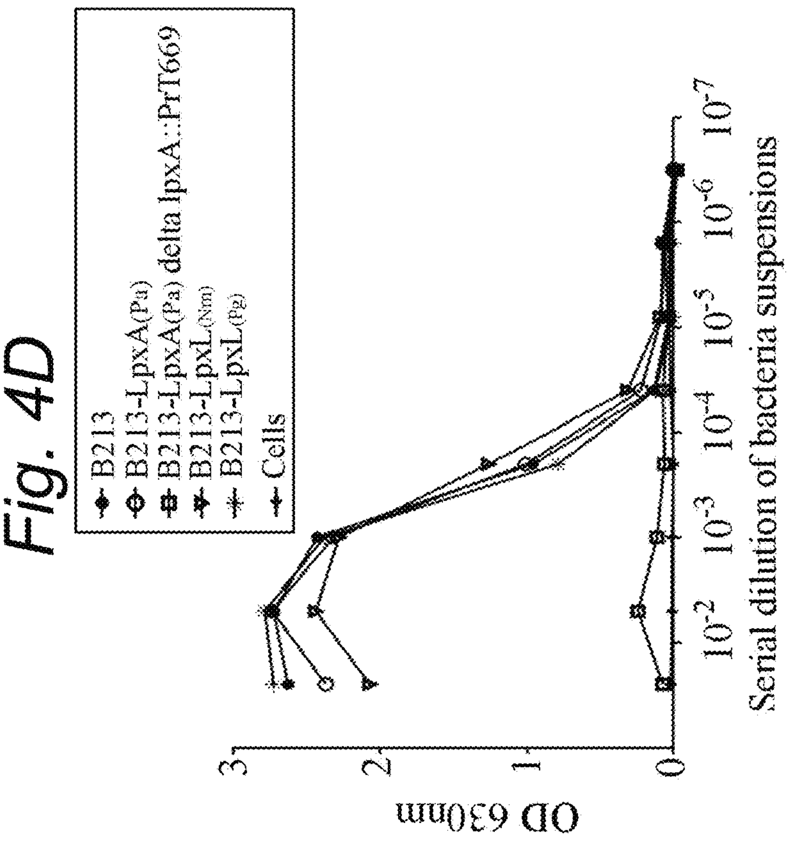

Stimulation of HEK293 cells expressing mTLR4 with LPS preparations from wild-type strain B213 resulted in a stronger response than observed in the cells expressing hTLR4 (compare FIGS. 4A and B). LPS preparations from B213 cells expressing the heterologous enzymes were slightly less effective in stimulating these cells (FIG. 4B). However when the chromosomal lpxA gene was inactivated in B213 expressing $LpxA_{(Pa)}$, the resulting LPS did not activate mTLR4 at all (FIG. 4B). Thus, the human and mouse TLR4 are activated differently by modified pertussis LPS, but the length of the primary acyl chain at the 3' position is critical in both cases. It was reported previously that the decreased toxicity of *B. pertussis* LPS that had lost the primary acyl chain at the 3 position was nullified in whole-cell preparations by its increased release from the membranes [2]. Taking this into account, we wished to determine the biological activity of whole-cell preparations. Expression of heterologous LPS enzymes in strain B213 affected the stimulation of HEK293 cells expressing hTLR4 similarly in whole-cell and purified LPS preparations (compare FIGS. 4A and C). Stimulation of HEK293 cells expressing mTLR4 by whole-cell preparations was barely affected by the expression of the heterologous enzymes in B213 (FIG. 4D). However, whole-cell preparations of the ΔlpxA mutant of B213 expressing $LpxA_{(Pa)}$ failed to activate these cells (FIG. 4D).

DISCUSSION

Their reactogenicity has led to the replacement of whole-cell pertussis vaccines by subunit vaccines, which, however, do not provide satisfactory protection. The development of new, less reactogenic whole-cell vaccines could offer a solution. LPS is, to a considerable extent, responsible for the toxicity of the cellular pertussis vaccines [2]. In the present study, we investigated if modification of acyl chain length in *B. pertussis* lipid A could result in reduced toxicity. We altered the length of primary acyl chain at the 3' position and of the secondary acyl chain at 2' position by expression of heterologous LpxA and LpxL acyltransferases. We found that reduction in the length of both acyl chains resulted in a drastic decrease in LPS toxicity (FIG. 4).

More precisely, substitution of a 3OH—C10 acyl chain for the 3OH—C14 chain present at the 3' position of lipid A abolished endotoxicity. In addition, substitution of the secondary C14 chain attached to the primary acyl chain at the 2' position by a C12 reduced endotoxicity. Consistently, the endotoxicity increased when this chain was substituted by a C16.

It was further observed that the reduction of the length of the acyl chains at the 2 and 2' positions of *B. pertussis* lipid A also has a large impact on the activation of hTLR4. Considering that the effect on toxicity is obtained independent of the position of the shorter acyl chain, the total volume of the hydrophobic moiety of the lipid A molecule is apparently important for the proper binding to and activation of the hTLR4 complex. The novel LPS species generated seem to function as hTLR4 antagonist as they could deplete any hTRL4 response (FIG. 5) even in the presence of considerable amounts of wild-type LPS (FIG. 3). This may not to be the case for LPS with a shorter secondary acyl chain as LPS from B213-$pLpxL_{(Nm)}$ showed residual activity in activating hTLR4 even though it contained lower amounts of the wild-type LPS than the purified LPS preparations from the strains expressing $LpxA_{(Pa)}$ or $LpxD_{(Pa)}$. It should be noted that expression of $LpxD_{(Pa)}$ in *B. pertussis* caused growth defects. Similarly, our previous results showed a growth defect of *B. pertussis* expressing $LpxL_{(Nm)}$.

In summary, our results demonstrate the importance of the acyl-chain length for activation of the immune system and for endotoxicity of *B. pertussis* LPS.

Our results also revealed a different effect of the LPS modifications on activation of mouse and human TLR4, where, in most cases, mTLR4 was less sensitive to the modifications. Previous studies reported species-dependent differences regarding TLR4 activation [24; 25]. These differences are explicable by interspecies variation in MD-2 and TLR4. These differences limit extrapolation of data from experimental animals to humans in vaccine trials [25]. Importantly, however, the LPS of the lpxA knockout mutant of strain B213 expressing $LpxA_{(Pa)}$ failed to activate both mTLR4 and hTLR4 in vitro allowing for extrapolation of results of planned experiments in mice to humans.

It is remarkable that the acyl chains at the 3 and 3' positions of *B. pertussis* lipid A differ in length [4]. LpxA catalyzes the first reaction in the lipid A biosynthetic pathway by transferring an acyl chain of a specific length onto the 3 position of GlcNAc in UDP-GlcNAc. The exact length of this acyl chain is defined by a hydrocarbon ruler in LpxA [26]. Later in the pathway, LpxH removes UMP in a proportion of the population of UDP-diacylglucosamine (UDP-DAG) precursors generating lipid X, after which LpxB links a UDP-DAG and a lipid X molecule generating a mono-phosphorylated, tetra-acylated glucosamine disaccharide in which the acyl chains at positions 3 and 3' are both derived from the original acylation by LpxA and, therefore, usually identical. Only rarely, LPS species with different acyl chain length at the 3 and 3' positions are found in nature. Consistent with the different acyl-chain length, expression studies in *E. coli* showed that *B. pertussis* LpxA has reduced chain-length specificity, but acyl chains of various lengths were incorporated at both the 3 and 3' positions [27]. Thus, the impeccable asymmetry in *B. pertussis* lipid A must be explained by chain-length specificity of an enzyme downstream in the pathway, which, we hypothesize, is LpxH. In our work, the expression of $LpxA_{(Pa)}$ resulted in two 3OH—C10 chains at positions 3 and 3', which was tolerated. However, the expression of $LpxA_{(Nm)}$, which would result in two primary 3OH—C12 chains at these positions (FIG. 1), appeared to be lethal. This can be explained if LpxH of *B. pertussis* can remove UMP only from UDP-DAG molecules containing a short 3OH—C10 chain at the 3 position. Indeed when we expressed $LpxH_{(Nm)}$ in *B. pertussis* the asymmetry disappeared, confirming our LpxH hypothesis (data not shown). Similarly, the heterologous expression of both $LpxA_{(Nm)}$ and $LpxH_{(Nm)}$ resulted in viable cells (data not shown). Hence to obtain a modified *Bordetella* lipid A moiety having an acyl-chain at the 3-position that is longer than 3OH—C10, may (in addition to a modified acyl transferase) require the presence of a modified LpxH, such as $LpxH_{(Nm)}$.

In conclusion, our approaches to reduce the toxicity of whole-cell *B. pertussis* vaccines by lipid A engineering as disclosed herein were effective. Our results show that the endotoxic activity of *B. pertussis* LPS is largely determined by the length of its fatty acyl chains. For the first time, we succeeded to engineer a strain that is totally devoid of endotoxic activity in in vitro assays. Importantly, this LPS did also not activate mTLR4 in vitro allowing for extrapolation of data obtained in planned animal studies to humans. Hence, our findings will allow for the generation of new cellular vaccines for *B. pertussis* and other pathogens.

TABLE 2A

SEQ ID NOs and corresponding protein and organism

| SEQ ID NO | Protein | Organism* |
|---|---|---|
| 1 | LpxA | Pa (PA01) |
| 2 | LpxL | Nm (H44/76) |
| 3 | LpxL | Pg (ATCC33277) |
| 4 | LpxD | Pa (PA01) |
| 5 | LpxH | Nm (H44/76) |
| 6 | LpxA | Nm (H44/76) |

TABLE 2A-continued

SEQ ID NOs and corresponding protein and organism

| SEQ ID NO | Protein | Organism* |
|---|---|---|
| 25 | PagL | Bb and Bp (GenBank WP-003813842.1) |
| 28 | LpxA | Bpe (GenBank: CAE41721.1) |
| 29 | LpxD | Bpe (GenBank: CAE41719.1) |
| 30 | LpxH | Bpe (Genbank: CAE42187.1) |
| 31 | LpxL | Bpe (Genbank: CAE43342.1) |
| 32 | LpxL | Pa (Genbank: AAG06812.1) |

*Pa = *Pseudomonas aeruginosa*, Nm = *Neisseria meningitidis*, Pg = *Porphyromonas gingivalis*, Bb = *B. bronchiseptica*, Bp = *Bordetella parapertussis*, Bpe = *Bordetella pertussis*

TABLE 2B

SEQ ID NOs and primer names

| SEQ ID NO | Primer name | Obtained product |
|---|---|---|
| 7 | $LpxA_{(Nm)}$ Fw | pMMB67EH-$LpxA_{(Nm)}$ |
| 8 | $LpxA_{(Nm)}$ Rev | |
| 9 | $LpxA_{(Pa)}$ Fw | pMMB67EH-$LpxA_{(Pa)}$ |
| 10 | $LpxA_{(Pa)}$ Rev | |
| 11 | $LpxL_{(Nm)}$ Fw | pMMB67EH-$LpxL_{(Nm)}$ |
| 12 | $LpxL_{(Nm)}$ Rev | |
| 13 | $LpxL_{(Pg)}$ Fw | pMMB67EH-$LpxL_{(Pg)}$ |
| 14 | $LpxL_{(Pg)}$ Rev | |
| 15 | $LpxA_{(Nm)}$ Fw RT | $lpxA_{(Nm)}$ |
| 16 | $LpxA_{(Nm)}$ Rev RT | |
| 17 | $LpxA_{(Pa)}$ Fw RT | $lpxL_{(Pa)}$ |
| 18 | $LpxA_{(Pa)}$ Rev RT | |
| 19 | $LpxL_{(Nm)}$ Fw RT | $lpxL_{(Nm)}$ |
| 20 | $LpxL_{(Nm)}$ Rev RT | |
| 21 | $LpxL_{(Pg)}$ Fw RT | $lpxL_{(Pg)}$ |
| 22 | $LpxL_{(Pg)}$ Rev RT | |
| 23 | Amp Fw RT | amp |
| 24 | Amp Rev RT | |
| 26 | $LpxD_{(Pa)}$ FW | pMMB67EH-$LpxD_{(Pa)}$ |
| 27 | $LpxD_{(Pa)}$ Rev-His | |

Example 2

$lpxD_{(Pa)}$ and $lpxA_{(Pa)}$ LPS Mutants Show Reduced Pyrogenicity in Rabbits

*Bordetella pertussis* mutants were constructed with an altered lipid A moiety in their LPS through heterologous expression of lpxA and lpxD genes from *Pseudomonas aeruginosa. Specifically, B. pertussis* B1917 strains were constructed wherein either the chromosomal lpxA gene or the lpxD gene was replaced with the corresponding *P. aeruginosa* versions. In both cases, this resulted in the synthesis of LPS with the expected shortened acyl chains, as shown by mass spectrometry.

In order to test the effect of these alterations in vivo, a rabbit pyrogenicity test was conducted with LPS purified from the lpxA mutant and from the lpxD mutant, and with OMVs extracted from the lpxD mutant, all in comparison to the wildtype. OMV (nOMV) were extracted by detergent-free extraction of the bacterial biomass with EDTA as chelating agent, essentially as described by van de Waterbeemd et al. (2010, Vaccine, 28(30):4810-6).

Figure 6A:
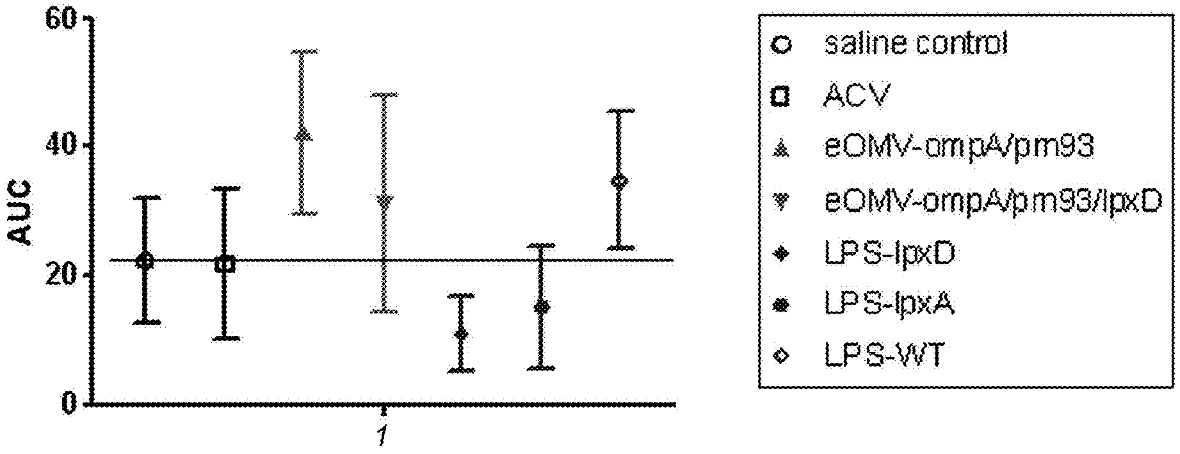
FIG. 6. In vivo pyrogenicity. Pyrogenicity in rabbits induced by mutant *Bordetella pertussis* LPS purified from an lpxA$_{(Pa)}$ mutant and from an lpxD$_{(Pa)}$ mutant, and with OMVs extracted from the lpxD$_{(Pa)}$ mutant, all in comparison to *B. pertussis* wildtype LPS and OMVs. Pyrogenicity is expressed as area under curve for 0-48 h and 0-8 h intervals.
Figure 6B:
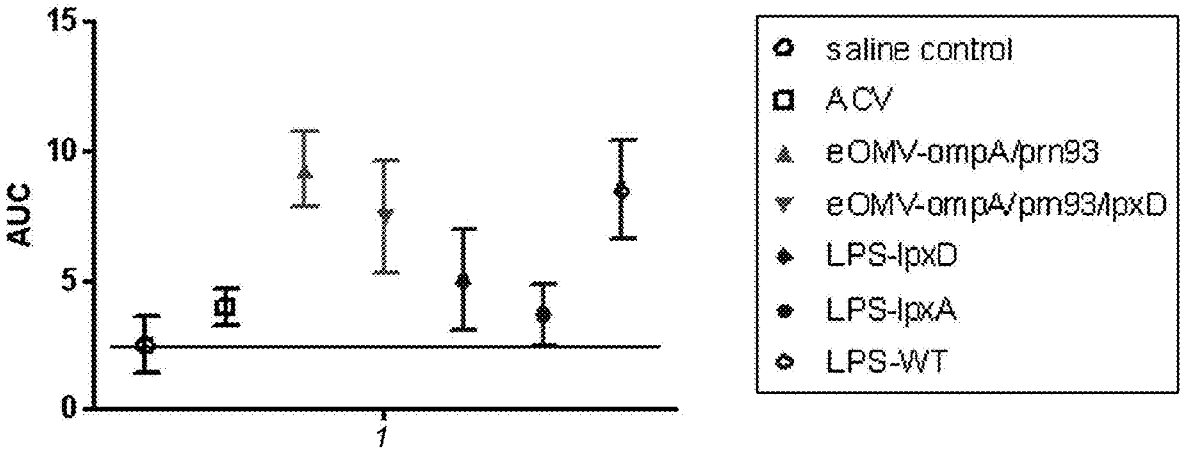

New Zealand White rabbits were injected intramuscularly with 0.5 ml of solution containing nOMVs (50 μg of protein) or purified LPS (10 μg), and acellular pertussis vaccine and saline as controls. The following groups were used (5 animals per group):

1. Vehicle Control (saline)
2. Reference vaccine (acP)
3. Vaccine 1: B1917 nOMV ompA prn
4. Vaccine 2: B1917 nOMV ompA prn lpxD
5. Vaccine 3: B1917 LPS lpxD
6. Vaccine 4: B1917 LPS lpxA
7. Vaccine 5: B1917 LPS wildtype Body temperature was measured using an external scanner from subcutaneously implanted transponders, at 0.5, 1, 2, 4, 6, 24 and 48 hrs after injection. The results are shown in Table 3 and in FIG. 6.

Results

A statistically significant rise in body temperature is seen with vaccine 1 (1, 2 and 4 h after injection) and vaccine 5 (4 h after injection). With purified LPS, there is a clear fever peak induced by the wildtype, but not by the lpxD and lpxA mutants. With OMVs, there is a more prolonged period of fever, both for wildtype and lpxD mutant, but lower for the latter. This is to be expected, as OMVs contain other pyrogenic components in addition to LPS.

CONCLUSIONS

The data demonstrate that mutant *Bordetella* LPS having a lipid A moiety wherein the length of at least one acyl chain is shorter as compared to the lipid A moiety of a wild-type *Bordetella* show a clearly reduced pyrogenicity in rabbits. The above observed in vitro data with HEK cells expressing TLR4 are therefore corroborated by these in vivo data.

TABLE 3

Data of pyrogenicity study in rabbits.

| Sex: Male | | TempFirstInj pretreat (° C.) [G] 0 (PreDos) | Temp (sc) first inj (° C.) [C] 0 (05hPtD) | Temp (sc) first inj (° C.) [C1] 0 (1hPstD) | Temp (sc) first inj (° C.) [C] 0 (2hPstD) | Temp (sc) first inj (° C.) [C1] 0 (4hPstD) | Temp (sc) first inj (° C.) [C] 0 (6hPstD) | Temp (sc) first inj (° C.) [C] 1 (24hPtD) | Temp (sc) first inj (° C.) [C] 2 (48hPtD) |
|---|---|---|---|---|---|---|---|---|---|
| Vehicle | Mean | 38.52 | 38.40 | 39.00 | 38.44 | 38.18 | 38.40 | 38.50 | 38.48 |
| | SD | 0.60 | 0.42 | 0.32 | 0.59 | 0.61 | 0.20 | 0.60 | 0.28 |
| | N | 5 | 5 | 5 | 5 | 5 | 5 | 5 | 5 |
| Reference vaccine | Mean | 38.92 | 38.72 | 37.98* | 38.66 | 38.84 | 38.72 | 38.38 | 38.28 |
| | SD | 0.26 | 0.36 | 0.89 | 0.17 | 0.29 | 0.46 | 0.56 | 0.61 |
| | N | 5 | 5 | 5 | 5 | 5 | 5 | 5 | 5 |
| Vaccine 1 | Mean | 37.90 | 38.34 | 39.78* | 39.64* | 40.18** | 39.00 | 38.98 | 38.28 |
| | SD | 0.69 | 0.38 | 0.38 | 0.40 | 0.70 | 0.95 | 0.48 | 0.44 |
| | N | 5 | 5 | 5 | 5 | 5 | 4 | 5 | 5 |
| Vaccine 2 | Mean | 38.20 | 38.52 | 39.32 | 39.52 | 39.54 | 38.76 | 38.76 | 38.08 |
| | SD | 1.14 | 0.53 | 0.48 | 0.77 | 1.27 | 0.86 | 0.78 | 0.77 |
| | N | 5 | 5 | 5 | 5 | 5 | 5 | 5 | 5 |
| Vaccine 3 | Mean | 38.06 | 37.84 | 39.20 | 38.76 | 39.38 | 38.22 | 37.96 | 38.36 |
| | SD | 0.48 | 0.69 | 0.32 | 0.62 | 1.18 | 0.46 | 0.68 | 0.36 |
| | N | 5 | 5 | 5 | 5 | 5 | 5 | 5 | 5 |
| Vaccine 4 | Mean | 38.06 | 38.46 | 38.68 | 38.90 | 38.54 | 38.48 | 38.12 | 38.38 |
| | SD | 0.86 | 0.31 | 0.24 | 0.59 | 0.51 | 0.54 | 0.45 | 0.41 |
| | N | 5 | 5 | 5 | 5 | 5 | 5 | 5 | 5 |
| Vaccine 5 Pos. cntrl | Mean | 38.50 | 38.16 | 38.64 | 39.40 | 40.46** | 38.76 | 38.74 | 38.34 |
| | SD | 0.70 | 1.04 | 0.81 | 1.11 | 0.76 | 0.63 | 0.35 | 0.59 |
| | N | 5 | 5 | 5 | 5 | 5 | 5 | 5 | 5 |

[G] - Ancova/Anova & Dunnett
[C] - Ancova/Anova & Dunnett {Covariate: Temp (Sc) FirstInj (pretreat)}: *= p < 0.05
[C1] - Ancova/Anova & Dunnett(Rank) {Covariate: Temp (Sc) FirstInj (pretreat)}: *= p < 0.05; **= p < 0.01

REFERENCES

[1] Clark T A. Changing pertussis epidemiology: everything old is new again. J Infect Dis 2014 Apr. 1; 209(7):978-81.
[2] Geurtsen J, Steeghs L, Hamstra H J, et al. Expression of the lipopolysaccharide-modifying enzymes PagP and PagL modulates the endotoxic activity of *Bordetella pertussis*. Infect Immun 2006 October; 74(10):5574-85.
[3] Peppler M S. Two physically and serologically distinct lipopolysaccharide profiles in strains of *Bordetella pertussis* and their phenotype variants. Infect Immun 1984 January; 43(1):224-32.
[4] Raetz C R, Whitfield C. Lipopolysaccharide endotoxins. Annu Rev Biochem 2002; 71:635-700.
[5] Rietschel E T, Schade U, Jensen M, Wollenweber H W, Luderitz O, Greisman S G. Bacterial endotoxins: chemical structure, biological activity and role in septicaemia. Scand J Infect Dis Suppl 1982; 31:8-21.
[6] Palsson-McDermott E M, O'Neill L A. Signal transduction by the lipopolysaccharide receptor, Toll-like receptor-4. Immunology 2004 October; 113(2):153-62.
[7] Alexander C, Rietschel E T. Bacterial lipopolysaccharides and innate immunity. J Endotoxin Res 2001; 7(3): 167-202.
[8] Conti P, Dempsey R A, Reale M, et al. Activation of human natural killer cells by lipopolysaccharide and generation of interleukin-1 alpha, beta, tumour necrosis factor and interleukin-6. Effect of IL-1 receptor antagonist. Immunology 1991 August; 73(4):450-6.
[9] Cinel I, Dellinger R P. Advances in pathogenesis and management of sepsis. Curr Opin Infect Dis 2007 August; 20(4):345-52.
[10] Crowell D N, Anderson M S, Raetz C R. Molecular cloning of the genes for lipid A disaccharide synthase and UDP-N-acetylglucosamine acyltransferase in *Escherichia coli*. J Bacteriol 1986 October; 168(1):152-9.
[11] Coleman J, Raetz C R. First committed step of lipid A biosynthesis in *Escherichia coli*: sequence of the lpxA gene. J Bacteriol 1988 March; 170(3):1268-74.
[12] Loppnow H, Brade H, Durrbaum I, et al. IL-1 induction-capacity of defined lipopolysaccharide partial structures. Expression of foreign LpxA acyltransferases in *Neisseria meningitidis* results in modified lipid A with reduced toxicity and retained adjuvant activity. Cell Microbiol 2002 September; 4(9):599-611.

[14] Wyckoff T J, Lin S, Cotter R J, Dotson G D, Raetz C R. Hydrocarbon rulers in UDP-N-acetylglucosamine acyltransferases. J Biol Chem 1998 Dec. 4; 273(49): 32369-72.

[15] Raetz C R, Reynolds C M, Trent M S, Bishop R E. Lipid A modification systems in gram-negative bacteria. Annu Rev Biochem 2007; 76:295-329.

[16] Verwey W F, Thiele E H, Sage D N, Schuchardt L F. A SIMPLIFIED LIQUID CULTURE MEDIUM FOR THE GROWTH OF HEMOPHILUS PERTUSSIS. J Bacteriol 1949 August; 58(2):127-34.

[17] Westphal O, K. Jann. Bacterial lipopolysaccharides extraction with phenol-water and further applications of the procedure. Methods carbohydrates chemistry 1965; 5:83-91.

[18] Pupo E, Hamstra H J, Meiring H, van der Ley P. Lipopolysaccharide engineering in *Neisseria meningitidis*: structural analysis of different pentaacyl lipid A mutants and comparison of their modified agonist properties. J Biol Chem 2014 Mar. 21; 289(12):8668-80.

[19] Brummelman J, Veerman R E, Hamstra H J, et al. *Bordetella pertussis* naturally occurring isolates with altered lipooligosaccharide structure fail to fully mature human dendritic cells. Infect Immun 2015 January; 83(1): 227-38.

[20] Geurtsen J, Angevaare E, Janssen M, et al. A novel secondary acyl chain in the lipopolysaccharide of *Bordetella pertussis* required for efficient infection of human macrophages. J Biol Chem 2007 Dec. 28; 282(52):37875-84.

[21] Park B S, Song D H, Kim H M, Choi B S, Lee H, Lee J O. The structural basis of lipopolysaccharide recognition by the TLR4-MD-2 complex. Nature 2009 Apr. 30; 458(7242):1191-5.

[22] DeMarco M L, Woods R J. From agonist to antagonist: structure and dynamics of innate immune glycoprotein MD-2 upon recognition of variably acylated bacterial endotoxins. Mol Immunol 2011 October; 49(1-2):124-33.

[23] Cunningham M D, Seachord C, Ratcliffe K, Bainbridge B, Aruffo A, Darveau R P. *Helicobacter pylori* and *Porphyromonas gingivalis* lipopolysaccharides are poorly transferred to recombinant soluble CD14. Infect Immun 1996 September; 64(9):3601-8.

[24] Akashi S, Nagai Y, Ogata H, et al. Human MD-2 confers on mouse Toll-like receptor 4 species-specific lipopolysaccharide recognition. Int Immunol 2001 December; 13(12):1595-9.

[25] Steeghs L, Keestra A M, van Mourik A., et al. Differential activation of human and mouse Toll-like receptor 4 by the adjuvant candidate LpxL1 of *Neisseria meningitidis*. Infect Immun 2008 August; 76(8):3801-7.

[26] Smith E W, Zhang X, Behzadi C, Andrews L D, Cohen F, Chen Y. Structures of *Pseudomonas aeruginosa* LpxA Reveal the Basis for Its Substrate Selectivity. Biochemistry 2015 Sep. 29; 54(38):5937-48.

[27] Sweet C R, Preston A, Toland E, et al. Relaxed acyl chain specificity of *Bordetella* UDP-N-acetylglucosamine acyltransferases. J Biol Chem 2002 May 24; 277(21): 18281-90.

The invention claimed is:

1. A genetically modified *Bordetella pertussis, Bordetella parapertussis* or *Bordetella bronchiseptica* bacterium, wherein the bacterium is modified compared to the wild-type *Bordetella pertussis, Bordetella parapertussis* or *Bordetella bronchiseptica* bacterium in that it has a genetic modification that introduces a heterologous acyl transferase activity, wherein the genetic modification that introduces heterologous acyl transferase activity confers to the cell at least one of a heterologous LpxA, LpxL and LpxD acyl transferase activity and wherein the genetic modification introduces the expression of at least one of a heterologous LpxA, a LpxL, and a LpxD acyl transferase, wherein i) the LpxA acyl transferase has SEQ ID NO: 1, or a variant thereof having at least 95% amino acid sequence identity with SEQ ID NO. 1;

ii) the LpxL acyl transferase has SEQ ID NO: 2, or a variant thereof having at least 95% amino acid sequence identity with SEQ ID NO. 2; and/or iii) the LpxD acyl transferase has SEQ ID NO: 4, or a variant thereof having at least 95% amino acid sequence identity with SEQ ID NO. 4, wherein expression of the heterologous acyl transferase results in a *B. pertussis, B. parapertussis* or *B. bronchiseptica* LPS having a lipid A moiety that is modified as compared to the lipid A moiety of a wild-type *B. pertussis, B. parapertussis* or *B. bronchiseptica* LPS in that the length of at least one acyl chain is shorter and wherein the length of the acyl chain at the 3 position of the modified lipid A moiety does not have a greater length than the acyl chain of the wild-type *B. pertussis, B. parapertussis* or *B. bronchiseptica* lipid A moiety at the same 3 position.

2. The genetically modified bacterium according to claim 1, wherein the bacterium is modified compared to the wild-type *B. pertussis, B. parapertussis* or *B. bronchiseptica* bacterium in that it has a genetic modification that introduces a heterologous UDP-2,3-diacylglucosamine pyrophosphatase activity.

3. The genetically modified bacterium according to claim 2, wherein the genetic modification introduces the expression of a heterologous lpxH UDP-2,3-diacylglucosamine pyrophosphatase, and wherein the LpxH UDP-2,3-diacylglucosamine pyrophosphatase has at least 95% sequence identity with SEQ ID NO: 5.

4. The genetically modified bacterium according to claim 3, wherein the lpxH UDP-2,3-diacylglucosamine pyrophosphatase has SEQ ID NO: 5.

5. *Bordetella* LPS, wherein the LPS is obtainable from a genetically modified *B. pertussis, B. parapertussis* or *B. bronchiseptica* bacterium according to claim 1.

6. The *Bordetella* LPS according to claim 5, wherein at least 70% of the LPS has a modified lipid A moiety, wherein the lipid A moiety is modified as compared to the lipid A moiety of a wild-type *Bordetella pertussis, Bordetella parapertussis* or *Bordetella bronchiseptica* LPS in that the length of at least one acyl chain is shorter, and wherein the shorter acyl chain selected from the group consisting of:

i) the acyl chain at the 3' position of the lipid A moiety is C10;

ii) the primary acyl chain at the 2' position of the lipid A moiety is C12;

iii) the secondary acyl chain at the 2' position of the lipid A moiety is C12; and iv) the acyl chain at the 2 position of the Lipid A moiety is C12, and wherein the length of the acyl chain at the 3 position of the modified lipid A moiety does not have a greater length than the acyl chain of the wild-type *Bordetella* lipid A moiety at the same 3 position.

7. The *Bordetella* LPS according to claim 6, wherein the length of the acyl chain at the 3 position of the modified lipid A moiety is not greater than C10.

8. The *Bordetella* LPS according to claim 7, wherein the length of the acyl chain at the 3 position of the modified lipid A moiety has the same length as the acyl chain of the wild-type *Bordetella* lipid A moiety at the same 3 position.

9. The *Bordetella* LPS according to claim 8, wherein the length of the acyl chain at the 3 position is C10.

10. An OMV obtainable from the genetically modified bacterium as defined in claim 1.

11. A composition comprising at least one of:

*Bordetella* LPS obtainable from a genetically modified bacterium according to claim 1;

a genetically modified bacterium of claim 1; and an OMV obtainable from the genetically modified bacterium of claim 1, wherein optionally the composition is a pharmaceutical composition further comprising a pharmaceutically accepted excipient.

12. The composition according to claim 11, wherein the genetically modified bacterium is inactivated.

13. The composition according to claim 11, wherein the composition further comprises at least one non-*Bordetella* antigen.

14. The genetically modified bacterium according to claim 1, wherein the bacterium is a genetically modified *Bordetella pertussis.*

15. The genetically modified bacterium according to claim 14, wherein the bacterium is a genetically modified *Bordetella pertussis* B213 strain.

16. The genetically modified bacterium according to claim 1, wherein the bacterium has a genetic modification that increases the expression of a lipid A 3-O-deacylase, and wherein the lipid A 3-O-deacylase has at least 95% sequence identity with SEQ ID NO: 25.

17. The genetically modified bacterium according to claim 1, wherein the modified bacterium further comprises a genetic mutation that reduces or eliminates the activity and/or expression of an endogenous LpxA acyl transferase and/or an endogenous LpxD acyl transferase, wherein the endogenous LpxA acyl transferase has at least 95% sequence identity with SEQ ID NO: 28 and wherein the endogenous LpxD acyl transferase has at least 95% sequence identity with SEQ ID NO: 29.

18. The genetically modified bacterium according to claim 1, wherein i) the variant of the LpxA acyl transferase has at least 98% amino acid sequence identity with SEQ ID NO: 1;

ii) the variant of the LpxL acyl transferase has at least 98% amino acid sequence identity with SEQ ID NO: 2; and/or iii) the variant of the LpxD acyl transferase has at least amino acid sequence identity with SEQ ID NO: 4.

19. The genetically modified bacterium according to claim 1, wherein i) the LpxA acyl transferase is SEQ ID NO: 1;

ii) the LpxL acyl transferase is SEQ ID NO: 2; and/or iii) the LpxD acyl transferase is SEQ ID NO: 4.

20. The genetically modified bacterium according to claim 1, wherein i) the variant of the LpxA acyl transferase is a heterologous LpxA acyl transferase obtained from a Gram negative bacterium;

ii) the variant of the LpxL acyl transferase is a heterologous LpxL acyl transferase obtained from a Gram negative bacterium; and iii) the variant of the LpxD acyl transferase is a heterologous LpxD acyl transferase obtained from a Gram negative bacterium.

21. A method for inducing or stimulating an immune response in a subject in need thereof, comprising administering to the subject the composition of claim 11, wherein the immune response is stimulated or induced against a *Bordetella* infection.

22. The method of claim 21, wherein the subject in need thereof suffers from whooping cough.

23. The method of claim 21, wherein the *Bordetella* infection is a *Bordetella pertussis* infection.

* * * * *